US006291247B1

(12) United States Patent
Riopelle et al.

(10) Patent No.: US 6,291,247 B1
(45) Date of Patent: *Sep. 18, 2001

(54) METHODS OF SCREENING FOR FACTORS THAT DISRUPT NEUROTROPHIN CONFORMATION AND REDUCE NEUROTROPHIN BIOLOGICAL ACTIVITY

(75) Inventors: Richard J. Riopelle; Gregory M. Ross, both of Kingston (CA); Magdalena I. Dory, Rhisnes (BE); Donald F. Weaver; Igor L. Shamovsky, both of Kingston (CA)

(73) Assignee: Queen's University at Kingston, Kingston (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/853,910

(22) Filed: May 9, 1997

Related U.S. Application Data

(63) Continuation-in-part of application No. 08/241,462, filed on May 11, 1994, now abandoned, and a continuation-in-part of application No. 08/745,608, filed on Nov. 8, 1996, now abandoned.
(60) Provisional application No. 60/010,328, filed on Nov. 9, 1995.

(30) Foreign Application Priority Data

Nov. 12, 1996 (CA) .................................... 2190296

(51) Int. Cl.$^7$ .......................... G01N 30/00; G01N 24/00; G01N 33/00; G01N 21/00
(52) U.S. Cl. ................................ 436/2; 435/7.2; 436/173; 436/164; 436/161; 436/183; 530/402; 530/412
(58) Field of Search ................................ 436/501, 164, 436/173, 183, 161, 2; 530/412, 402; 435/7.2

(56) References Cited

U.S. PATENT DOCUMENTS 5,134,121    7/1992   Mobley et al. .

FOREIGN PATENT DOCUMENTS

| 335637 | 10/1989 | (EP) . |
| 414151 | 2/1991 | (EP) . |
| WO 9208483 | 5/1992 | (WO) . |
| WO 9521193 | 8/1995 | (WO) . |
| WO 97/15593 | 5/1997 | (WO) . |

OTHER PUBLICATIONS

Kolbeck et al., *Eur. J. Biochem.*, vol. 225, pp. 995–1003, 1994.*
Jungbluth et al., *Eur. J. Biochem.*, 221, pp. 677–685, Apr., 1994.*
Rao et al., *JBC*, vol. 259, pp. 73–79, 1984.*
Pattison et al., *Biochemistry*, vol. 14, pp. 2733–2739, 1975.*
Young et al., *Biochemistry*, vol. 27, pp. 6675–6681, 1988.*
Radziejewski et al., *Biochemistry*, vol. 32, pp. 13,350–13,356, 1993.*
$ZN^{2+}$: an Endogenous Modulator of Ligand– and Voltage––gated Ion Channels, N.L., Harrison et al. Neuropharmacol. vol. 33, No. 8 pp. 935–952 (1994).
New Protein Fold Revealed by a 2.3–A Resolution Crystal Structure of Nerve Growth Factor, Neill McDonald et al., Nature vol. 354 pp. 411–414, Dec. 5, 1991.
Nerve Growth Factor in Different Crystal Forms Structural Flexibility and Reveals Zinc Binding Sites, Debra R. Holland et al., J. Mol Bio. vol. 239 pp. 385–400 (1994).
Ben–Ari, et al., "Brief seizure episodes induce long–term potentiation and mossy fibre sprouting in the hippocampus", *TINS* 13(8): 312–318 (1990).
Dory, et al., "Theoretical studies on a conformationally constrained peptide(R–11) antagonist of NGF; molecular dynamics simulations". Abstract, *Neurotrophic Factors: Receptors and Cellular Mechanisms I*, Society for Neuroscience Abstracts, vol. 21 (1995).
Drinkwater, et al., "The carboxyl terminus of nerve growth factor is required for biological activity", *J. Biol. Chem.* 268(31): 23202–23207 (1993).

(List continued on next page.)

*Primary Examiner*—Gary L. Kunz
*Assistant Examiner*—Stephen Gucker
(74) *Attorney, Agent, or Firm*—Carol Miernicki Steeg; Lynn C. Schumacher; Dowell & Dowell, P.C.

(57) ABSTRACT

Factors and methods for disrupting or inhibiting the association of protomers of a multimeric protein are described. Such inhibition reduces the biological disorders. Particularly, novel neurotrophin antagonists are described. Generally, the antagonist comprises amino acids from positions 68–58 and 108–110 of a neurotrophin, in which the amino acid from position 68 is covalently bound to the amino acid from position 108 and the amino acid from position 58 is covalently bound to the amino acid at position 110 to form a bicyclic structure, in another aspect of the invention transition metal ions are provided for selectively altering the geometry of the receptor binding domains of neurotrophins which allows functionality and activity of the neurotrophins to be selectively reduced. For example $Zn^{2+}$ alters the conformation of NGF rendering it unable to bind to $p75^{NTR}$ or TrkA receptors or to activate signal transduction and biological outcomes normally induced by this protein. Molecular modelling studies predict that $Zn^{2+}$ binding to NGF will induce structural changes within domains of this neurotrophin which participate in the recognition of TrkA and $p75^{NTR}$. $Ni^{2+}$ on the other hand selectively alters the conformation of NGF rendering it unable to bind to TrkA but does not affect binding to $p75^{NTR}$. Similar actions of $Zn^{2+}$ are also observed with other members of the NGF family, suggesting a modulatory role for the metal ions in neurotrophin function.

18 Claims, 26 Drawing Sheets

OTHER PUBLICATIONS

Hruby, et al., "Emerging approaches in the molecular design for receptor–selective peptide ligands: conformational, topographical and dynamic considerations", *Biochem. J.* 268:249–262 (1990).

Ibáñez, et al., "Disruption of the low affinity receptor–binding site in NGF allows neuronal survival and differentiation by binding to the trk gene product", *Cell* 69: 329–341 (1992).

Ibáñez, et al., "An extended surface of binding to Trk tyrosine kinase receptors in NGF and BNDF allows the engineering of a multifunctional pan–neurotrophin", *EMBO J.* 12: 2281–2293 (1993).

Jaen, et al., "Kynurenic acid derivatives inhibit the binding of nerve growth factor (NGF) to the low–affinity p75 NGF receptor", *J. Med. Chem.* 38: 4439–4445 (1995).

Kahle, et al., "The amino terminus of nerve growth factor is involved in the interaction with the receptor tyrosine kinase p140", *J. Biol. Chem.* 267(32): 22707–22710 (1992).

Longo, et al., "The in vitro biological effect of nerve growth factor is inhibited by synthetic peptides", *Cell Regulation* 1: 189–195 (1990).

Rashid, et al., "A nerve growth factor peptide retards seizure development and inhibits neuronal sprouting in a rat model epilepsy", *Proc. Natl. Acad. Sci. USA* 92: 9495–9499 (1995).

Rashid et al., "Peptide mimics of an NGF domain inhibit kindling and neuronal sprouting in rats", Abstract, *Neurotrophic Factors: Biological Effects VI*, Society for Neuroscience Abstracts, vol. 20 (1994).

Riopelle, et al., "Some aspects of porphyrin neurotoxicity in vitro", *Can. J. Phys. Pharm.* 60(5): 707 (1982).

Ross, et al., "A conformationally constrained peptide antagonist modelled from two non–contiguous domains of nerve growth factor", Abstract, *Neurotrophic Factors: Receptors and Cellular Mechanisms I*, Society for Neuroscience Abstracts, vol. 21 (1995).

Spiegel, et al., "PD 90780, a non peptide inhibitor of nerve growth factor's binding to the p75 NGF receptor", *Biochem. Biophys. Res. Comm.* 217:488–494 (1995).

\* cited by examiner

FIG 2

LINEAR NGF PEPTIDE:

$C^{68}$-G-S-E-V-P-N-S-A-R-$C^{58}$-$C^{108}$-V-$C^{110}$ (SEQ ID NO:1)

CYCLIC NGF PEPTIDE:

$C^{68}$-G-S-E-V-P-N-S-A-R-$C^{58}$-$C^{108}$-V-$C^{110}$ (SEQ ID NO:1)

BICYCLIC NGF PEPTIDE:

$C^{68}$-G-S-E-V-P-N-S-A-R-$C^{58}$-$C^{108}$-V-$C^{110}$ (SEQ ID NO:1)

Conc'n Bicyclic Peptide
($\mu$M)

FIG 5D

| | | |
|---|---|---|
| NH₂ | COOH | Analog Code |

```
          Acm  Acm
           |    |
C G S E V P N S A R C C V C            R11(l)
```

```
              Acm  Acm
               |    |
C G E S V P N S A R C C V C            R11(m)
|_____|
```

```
                       ┌─┐
                       | |
C G E S V P N S A R C C V C            R11
|_____|
```

```
                       ┌─┐
                       | |
C R A S N P V E S G C C V C            SR11
|_____|
```

```
      ┌─┐
      | |
C V C C R A S N P V E S G C            BR11
|_____|
```

C-(A)6-CCVC

FIG 10

CCVC-(A)6-C

METHODS OF SCREENING FOR FACTORS THAT DISRUPT NEUROTROPHIN CONFORMATION AND REDUCE NEUROTROPHIN BIOLOGICAL ACTIVITY

CROSS REFERENCE TO RELATED U.S. PATENT APPLICATIONS

This patent application is a continuation-in-part of U.S. patent application Ser. No. 08/241,462 filed on May 11, 1994 entitled NEUROTROPHIN ANTAGONISTS, now abandoned, and U.S. patent application Ser. No. 08/745,608 filed on Nov. 8, 1996 entitled METHOD OF REDUCING BIOLOGICAL ACTIVITY OF A MULTIMERIC PROTEIN AND METHODS OF SCREENING FOR A FACTOR THAT REDUCES BIOLOGICAL ACTIVITY OF A MULTIMERIC PROTEIN, now abandoned, and which claims priority from U.S. patent application Ser. No. 60/010,328 filed on Nov. 9, 1995. These applications are hereby incorporated herein in their entirety by reference.

FIELD OF THE INVENTION

The present invention relates generally to the field of protein structure-function relationships. More specifically, the invention relates to perturbation of the native structure of a protein so as to reduce its biological activity. Still more specifically, the invention relates to methods of disrupting the interaction of promoters of a multimeric protein so as to reduce its biological activity. In particular, the invention relates to compounds and methods of disrupting association of the promoters of a neurotrophin, so as to reduce its biological activity. More particularly, the present invention relates to neurotrophin-derived peptides and analogues thereof and to metal ions, which disrupt the interaction of neurotrophin promoters, thereby inhibiting or reducing neurotrophin activity that may be undesirable in certain situations.

BACKGROUND OF THE INVENTION

Multimeric proteins are those composed of two or more polypeptide subunits, or promoters. A dimeric protein has two promoters, a tetramer has four promoters, and so on. In a particular multimeric protein, the component promoters associate in a specific way to produce the protein's native quaternary structure. For a dimer, such assembly or association is called dimerization. The promoters of a given multimeric protein may be identical to ("homo-") or different from ("hetero-") each other. For example, the homodimeric protein nerve growth factor (NGF) has two identical promoters. Promoters may differ in function within the multimeric protein. For example, the heterodimeric protein cholera toxin has a first subunit that permits penetration of the plasma membrane by the toxin and a second, non-identical subunit fit catalyzes the covalent modification of a cytosolic G-protein.

It is well known in biochemistry that the activity of a multimeric protein often depends on association of its component subunits. For example, the individual promoters of a particular enzyme may display no catalytic activity in isolation, but are only able to function when in a multimeric state. Similarly, various signal transduction pathways require ligand-induced self-association of cell surface receptors such as EGF-R, PDGF-R and the neurotrophin receptors for signalling to occur. Various ligands involved in signal transduction are themselves known to exist in multimeric form, e.g., NGF. There are several compelling reasons, from a neurological perspective, to be able to disrupt promoters involved in certain neurological processes.

The neurotrophins are a family of structurally and functionally related neurotrophic factors. The family includes prototypic member NGF, as well as brain-derived neurotrophic factor (BDNF), neurotrophin-3 (NT-3), neurotrophin-4/5 (NT-4/5) (Heumann, *Curr. Opin. Neurobiol.* 4: 668–679 (1994)) and neurotrophin-6 (NT-6) (Gotz et at., *Nature* 372: 226–269 (1994)). The neurotrophins have similar structural conformations, including three surface β-hairpin loops, a β-strand, an internal reverse turn region, and N-and C-termini, and exhibit approximately 50% amino acid sequence identity.

Neurotrophins function to promote growth and survival of certain classes of peripheral and central neurons both during development and following neuronal damage. For example, NGF is involved in the development of neurons in the peripheral nervous system, supports neuronal survival, and enhances and maintains the differentiated state of neurons. Neurotrophins can promote neurite differentiation such as sprouting or process formation, and process growth. Neurotrophins can also modulate cell motility (Anton et al., *Proc. Nat. Aced. Sci. USA* 91: 2795–2799 (1994)), for example, both accelerate nerve process growth and decrease general cell motility. Another neurotrophin-mediated activity is induction of particular enzymes.

Furthermore, with respect to functional similarity, each of the neurotrophins can bind to a membrane bound receptor protein (MW~75 kDa) called the common neurotrophin receptor, or "$p75^{NTR}$". Each neurotrophin also binds with higher affinity to a second membrane-bound receptor protein of the tyrosine kinase receptor (Trk) family. In particular, NGF binds selectively to the TrkA receptor, and BDNF and NT-4/5 bind selectively to the TrkB receptor. NT-3 is less selective and, though it binds primarily to the TrkC receptor, NT3 also exhibits some binding to the TrkA and TrkB receptors (Ibanez et al., *EMBO J.* 12: 2281–2293 (1993)).

A variety of cell types express either $p75^{NTR}$ and/or a member of the Trk family of receptor tyrosine kinases. These include neurons, mast cells, glial cells such as astrocytes, oligodendrocytes and Schwann cells, and dysplasic or malignant cells such as neuroblastoma or melanoma cells. Cells of neuronal lineage that differentiate by extension of neurites in the presence of a neurotrophin in express both a member of the Trk receptor family and lower molecular weight receptor protein $p75^{NTR}$.

NGF, a 118 amino acid protein, is an extremely important neurotrophin, being implicated in the pathogenesis of Alzheimer's disease, epilepsy and pain. The binding of NGF to its receptors is determined by distinct sequences within its primary amino acid structure The hairpin loop at residues 29–35 is responsible for recognition by $p75^{NTR}$, while the amino and carboxy termini are important binding determinants for recognition by the TrkA receptor NGF exerts its biological activity as a non-covalent dimer. Two 118 residue NGF monomers are dimerized by hydrophobic and van der Waals interacts between their three anti-parallel pairs of β-strands. Consequently, the amino terminus of a first NGF protomer and the carboxyl terminus of a second NGF protomer are spatially juxtaposed, and the amino terminus of the second NGF protomer and the carboxyl terminus of the first NGF protomer are spatially juxtaposed. Furthermore, although the NGF dimer thus has 2 pairs of termini, only one pair of termini is required for TrkA receptor recognition.

Variable domains within the NGF family of neurotrophins include the NGF NH2- and COOH-terminal residues (1–9 and 111–118, respectively) and certain internal residues that are revealed by the crystal structure of NGF (McDonald et al., *Nature* 354: 411–414 (1991)) to form four loop structures. These loops are three β sheet structures, residues 25–35 (Loop 1, L1), 40–50 (Loop 2, L2) and 90–100 (Loop 4, L4); and a twisted loop (Loop 3, L3) residues 62–68.

It has been suggested previously that the variable regions mediate the biological effects of the neurotrophins, via specific Trk family receptors and the common neurotrophin receptor p75. This suggestion led to the employment of site-directed mutagenesis and recombinant chimeric protein techniques to demonstrate that specific residues within L2, 14 and the $NH_2$ and COOH termini are required for Trk activation (Kahle et al., *J. Biol Chem.* 267: 22707–22710 (1992); Kullander et al., *J. Neurosci. Res.* 39: 195–210 (1994); Drinkwater et al., *J. Biol. Chem.* 268: 23202–23207 (1993)), and that domains of L1 and L4 are involved in p75 binding (Ibanez et al., *EMBO J.* 12: 2281–2293 (1993)). Monoclonal antibodies against antigenic determinants encompassing the $NH_2$ and COOH termini and the L3 region of NGF implicate these domains in trkA receptor signalling (Nanduri et al., *J. Neurosci. Res.* 37: 433–444 (1994)).

Residues 58, 67, 68, 108, 109 and 110 are included in those residues that are conserved among the neurotrophins. The specific requirements of these residues with respect to NGF binding to receptors have not been examined using recombinant protein techniques, as they are required for protein structural integrity. The participation of NGF residues 60–67 in mediating interaction of NGF with either p75 or TrkA has been excluded by deletion mutagenesis studies (Drinkwater et al., *J. Biol. Chem.* 268: 23202–23207 (1993)).

Neurite growth is the best characterized differentiation response to NGF, and evidence is beginning to emerge that $p75^{NTR}$ can modulate this activity. Gene targeting studies resulting in nonfunctional $p75^{NRT}$ demonstrate reduced density of sensory and sympathetic innervation in vivo (Lee et al., *Development* 120: 1027–1033 (1994); Lee et al., *Science* 263: 1447–1449 (1994)), possibly related to a shift to the right of dose response curves for NGF (Davies et al., *Neuron* 11: 565–574 (1993)). Furthermore, evidence is beginning to emerge that p7em can activate apoptosis (Frade et al., *Nature* 166–168 (1996); Casaccia-Bonnefil et al. *Nature* 383: 716–719 (1996); Van der Zee et al., *Science* 274: 1729–1732 (1996)). Inhibiting $p75^{NTR}$ function may thus contribute to preventing of cell death.

The neurotrophins function primarily to promote survival of certain classes of peripheral and central neurons both during development and following neuronal damage. NGF, in particular, is involved with the development of neurons in the peripheral nervous system and supports neuronal survival, as well as enhancing and maintaining the differentiated state of neurons. Several lines of evidence also suggest that NGF may mediate inflammation (Levi-Montalcini, *Science* 237: 1154–1162 (1987)). However, in some neurological disease states, the neurotrophins may also support inappropriate neurite outgrowth thereby facilitating the progression of a disease condition. For example, neurotrophins promote the undesirable sprouting of hippocampal "mossy fibres". Such inappropriate sprouting of mossy fibers is a common accompaniment of epilepsy in humans. In other pathological states, such as Alzheimer's disease, as mentioned above, aberrant process growth, known as dystrophic neurite formation, is a strong correlate of disease severity.

Thus, although the neurotrophins are essential for the normal development and growth of neurons, they may be detrimental under certain circumstances. In such instances, factors capable of inhibiting or reducing selected neurotrophin-mediated activities, such as receptor binding and consequent signal transduction, would be desirable therapeutically to treat neurodegenerative disease and to repair nervous system injury.

SUMMARY OF THE INVENTION

It is an object of the present invention to provide factors capable of disrupting, inhibiting or reducing interaction of promoters of a multimeric is protein.

It is a further object of the present invention to provide factors capable of disrupting, inhibiting or reducing undesirable neurotrophin-mediated activity.

More specifically, it is an object of the present invention to provide small peptides, functional equivalents thereof, and a method of using such factors for disrupting, inhibiting or reducing association of the promoters of a multimeric protein, preferably a neurotrophin.

It is also an object of the present invention to provide metal ions capable of altering the geometry or conformation of a receptor binding domain of a neurotrophin to reduce neurotrophin-mediated activity.

In the case of some physiological disorders, it may be desirable to disrupt the multimeric association of a particular protein, such as, for example, a neurotrophin, so as to reduce or even eliminate its biological activity and hereby produce a therapeutic effect. The present invention provides a method of reducing the biological activity of a multimeric protein having at least two promoters by perturbing the association of the promoters, i.e., disrupting multimer integrity. The method includes the step of providing a factor that mimics a portion of an interface between the promoters. In this context, mimicking should be understood in a functional sense, wherein the factor is characterized by being able to perturb association of the promoters. A subsequent step of the method is mixing the factor with the protein. The factor may be a peptide, peptide derivative or peptidomimetic. The mixing step may include administering the factor to a human or an animal so that the factor interacts with the multimeric protein in situ, providing a therapeutic effect. The multimeric protein may be an enzyme. It may be involved in signal transduction; for example, the multimer may be a ligand or a receptor in a signal transduction pathway. In a preferred embodiment, the multimeric protein is a member of the cysteine knot family of growth factors, which family includes NGF, $TGF\beta_2$ and PDGF. In a preferred embodiment, the multimeric protein is a neurotrophin.

The invention further provides a sensitive, rapid and convenient method of screening for and identifying factors that can disrupt the association of promoters of a multimeric protein. In a preferred embodiment, the multimeric protein is a member of the cysteine knot family of grow factors or a neurotrophin. The method includes the steps of providing a candidate factor that mimics a portion of an interface between the promoters, mixing the factor with the protein, and determining whether the conformation of the protein is perturbed in the presence of the factor. A factor that reduces the amount of a multimeric species of the protein in favor of species having fewer promoters can be identified. Such a factor may be useful in reducing the biological activity of the multimeric protein, i.e., be an antagonist.

The step of determining whether the conformation is perturbed may include separating different species of the protein, wherein the species are distinguished from each other by having different numbers of promoters. The method may include, prior to the separation step, the step of subjecting the mixture to a cross-linking agent hat covalently joins promoters within a multimeric species. The separation step may include any technique for separating different protein species that would be known to a person skilled in the art These techniques include gel filtration, HPLC, isoelectric focussing and gel electrophoresis. Electrophoresis may be non-denaturing, or in the case where a chemical cross-linking step has taken place, denaturing.

In another embodiment, the step of determining whether the conformation is perturbed may include circular dichroism (CD), nuclear magnetic resonance (NMR) spectroscopy, fluorescence spectroscopy, x-ray crystallography or another technique based on similar principles.

The invention further provides a factor that can disrupt the association of promoters of a multimeric protein, as described above.

The invention additionally provides use of a factor according to the invention to treat a human being or an animal. A kit for a screening system according to the invention could be assembled. The screening a system of the invention could also be automated.

Factors and methods according to the invention can thus provide a solution to problems presented in certain physiological conditions, where the reduction or inhibition of the activity of a multimeric protein would be advantageous and desired.

Accordingly, in one of its aspects the present invention provides bicyclic neurotrophin-derived peptides, or functional equivalents thereof, which inhibit a neurotrophin-mediated activity.

In one aspect, the present invention provides a peptide comprising amino acids identical to residues 58 to 68 of NGF but in the reverse order, and amino acids from palindromic residues 108–110 of NGF, or a functional equivalent of said peptide. Where the peptide, reading according to convention from N-terminus to C-terminus, is represented as residues 68 to 58 covalently bound to residues 108 to 110, furthermore the amino add from position 58 has a second covalently bond to the amino acid from position 108, and the amino acid from position 68 is covalently bound to the amino acid at position 110 to form a bicyclic structure.

In another aspect of the present invention, a composition is provided comprising said peptide comprising amino acids from positions 58–68 and 108–110 of a neurotrophin, or a functional equivalent thereof, and a carrier therefor.

In a further aspect of the present invention, there is provided a method for inhibiting a neurotrophin-mediated activity comprising the step of exposing neurons to a composition as described above including a bicyclic neurotrophin-derived peptide or functional equivalent thereof in combination with a suitable carrier.

A further aspect of the present invention provides a method for inhibiting neurtophin-mediated activity in a mammal comprising the step of administering to said mammal a therapeutically effective amount of a composition which includes a bicyclic neurotrophin-derived peptide or functional equivalent thereof in combination with a pharmaceutical carrier.

The invention further provides a method of inhibiting undesirable neurotrophin-mediated activity. In a preferred embodiment, the method includes the step of mixing a metal ion with a neurotrophin, wherein the metal ion is capable of binding to the neurotrophins so that geometry or conformation of a receptor binding domain of the neurotrophin is altered. Furthermore, the binding of the metal ion perturbs association of the promoters of the neurotrophin. Preferably, the neurotrophin is NGF and the metal ion is a transition metal ion.

The present invention also provides a method of using transition metal ions to alter the quaternary structure of a neurotrophin, lowering its binding affinity for to its receptor (s) and reducing its ability to activate signal transduction and biological outcomes normally induced by this protein. In a preferred embodiment, the transition metal is $Zn^{2+}$. In another preferred embodiment, the neurotrophin receptor is $p75^{NTR}$ or a Trk receptor. In a further preferred embodiment, the neurotrophin receptor is TrkA and the neurotrophin is NGF. Similar actions of $Zn^{2+}$ are also observed with other members of the NGF family, for example, BDNF and NT3, and the use of $Zn^{2+}$ to modulate biological activity of a neurotrophin falls within the scope of this invention. In an alternative embodiment the metal ion is $Ni^{2+}$, herein $Ni^{2+}$ perturbs association of neurotrophin promoters and reduces affinity of the neurotrophin for a Trk receptor. In his embodiment, preferably, affinity of the neurotrophin for $p75^{NTR}$ is not significantly altered. The use of $Ni^{2+}$ to modulate biological activity of a neurotrophin in falls within the scope of this invention.

The present invention provides a method of reducing biological activity of a multimeric protein having at least two promoters, comprising the steps of providing a factor that interacts with at least one portion of at least one of the promoters that, in the absence of the factor, associates with a portion of said other protomer, and mixing the factor with the multimeric protein, wherein the factor interacting with the at least one portion disrupts association of at least a portion of the at least two promoters.

In another aspect of the invention there is provided a method of reducing biological activity of a neurotrophin having at least two promoters, comprising the steps of providing a physiologically acceptable metal cation that perturbs association of the promoters in the neurotrophin; and mixing the metal cation with the neurotrophin, wherein the metal cation interacts with the neurotrophin so that biological activity of the neurotrophin is reduced.

In a further aspect of the invention there is provided a method of reducing biological activity of a neurotrophin having at least two promoters, comprising the steps of providing a physiologically acceptable metal cation that alters conformation of at least one receptor binding domain of the neurotrophin and perturbs association of the promoters in the neurotrophin; and mixing the metal cation with the neurotrophin.

In another aspect of the invention there is provided a method of screening for a factor that disrupts the association of promoters of a multimeric protein, comprising the steps of providing a candidate factor that interacts with at least one portion of at least one of said promoters that, in the absence of the factor, associates with a portion of the other protomer, providing a multimeric protein having at least two promoters and determining a conformation of the multimeric protein in the absence of the candidate factor, mixing the candidate factor with the multimeric protein; determining if the conformation of the multimeric protein has been perturbed in the presence of the candidate factor, and identifying a factor that perturbs the conformation.

BRIEF DESCRIPTION OF THE DRAWINGS

These and other aspects of the present invention will be described in detail by reference to the following figures in which:

FIG. 2 illustrates linear, cyclic and bicyclic peptides (Sequence ID No. 1) prepared from the 68–58/108–110 region of NGF (see also first portion of FIG. 5D).

FIG. 5D shows linear, monocyclic and bicyclic R11 peptides as described in FIG. 2 (SEQ ID NO: 1), aligned with analogues SR11 (SEQ ID NO: 7) and BR11 (SEQ ID NO: 8).

FIG. 10 shows the calculated most stable conformation of molecule XV (CVCCAAAAAAC), (Sequence ID No. 10).

DETAILED DESCRIPTION OF THE INVENTION

Figure 1:
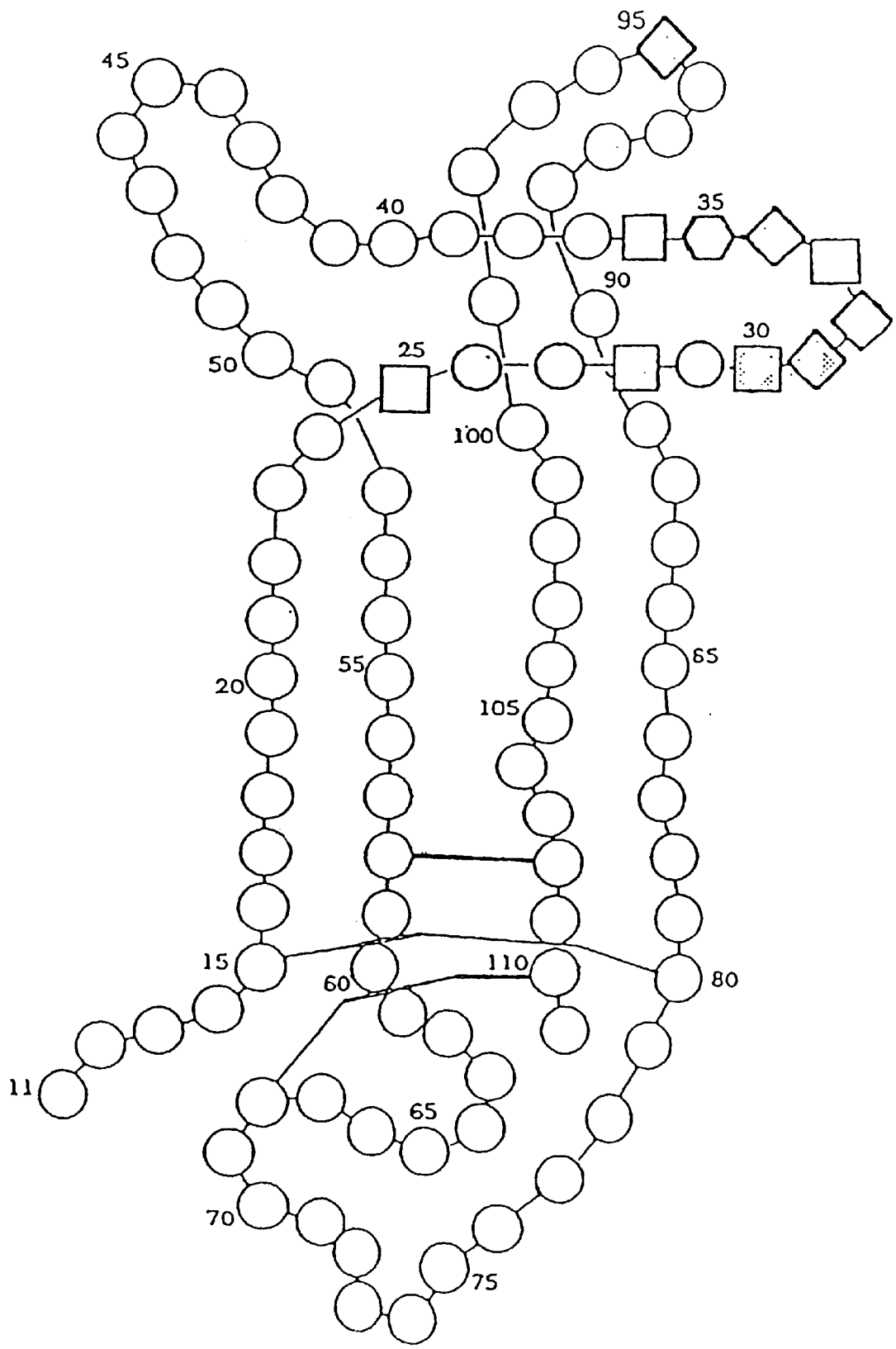
FIG. 1 illustrates generally the structure of a neurotrophin.
Figure 3:
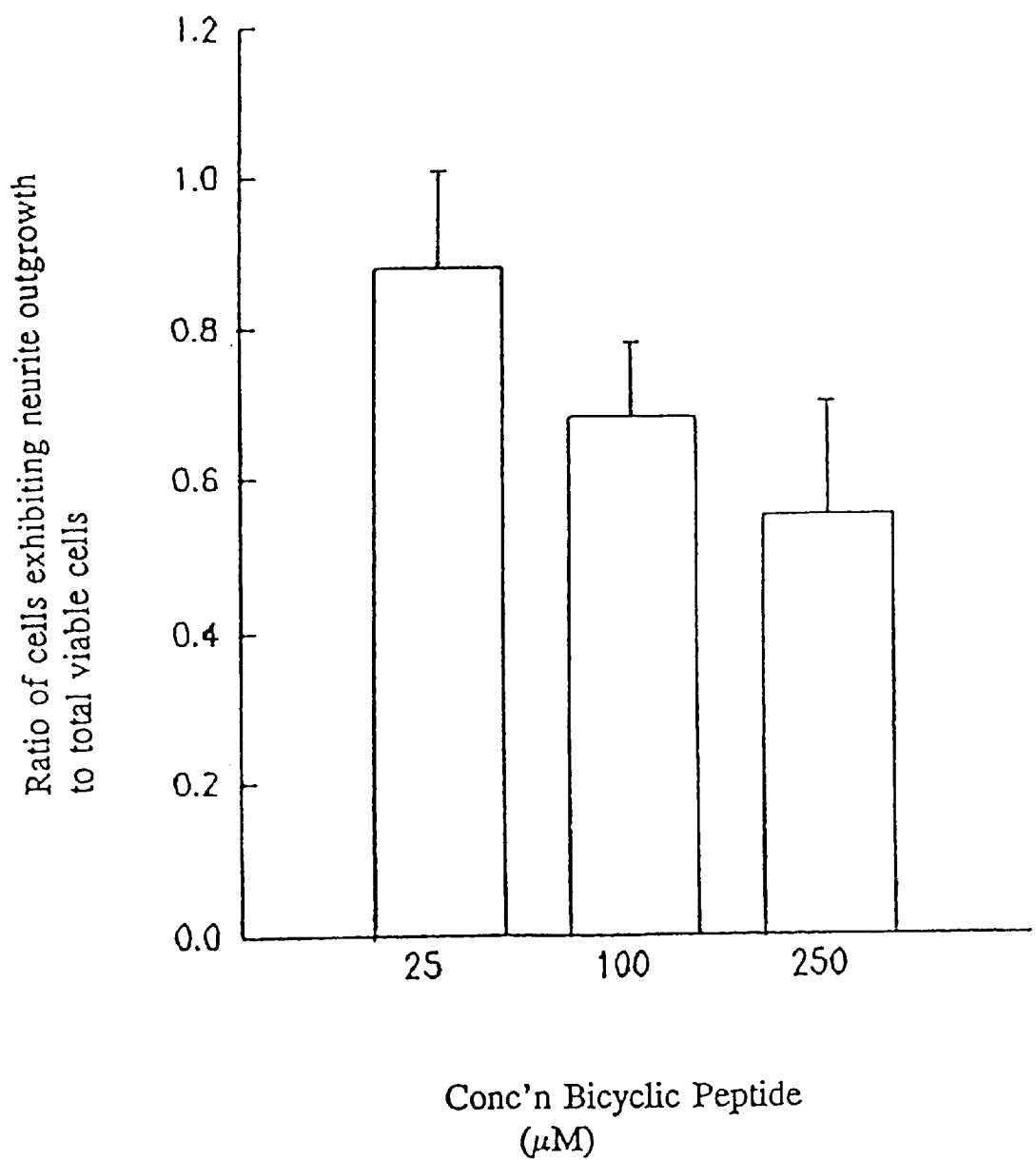
FIG. 3 graphically illustrates the effect of the bicyclic NGF peptide of FIG. 3 on neurite outgrowth.

As it is used herein, the term "neurotrophin-derived" refers to factors having functional characteristics of an amino acid sequence native to a given mammalian neurotrophin. In a preferred embodiment, such factor is a peptide or peptidomimetic.

"Neurotrophin-mediated" activity is a biological activity that is normally promoted, either directly or indirectly, in the presence of a neurotrophin. Neurotrophin-mediated activities include, for example, neurotrophin binding to the common neurotrophin receptor $p75^{NTR}$, or neurotrophin binding to one of the Trk receptors, neuron survival, neuron differentiation including neuron process formation and neurite outgrowth, and biochemical changes such as enzyme induction. A biological activity that is mediated by a particular neurotrophin, e.g., NGF, is referred to herein by reference to that neurotrophin, e.g., NGF-mediated activity. To determine the ability of a factor, such as, for example, a bicyclic peptide or a functional equivalent thereof, to inhibit a neurotrophin-mediated activity, conventional in vitro and in vivo assays can be used For example, a receptor affinity cross linking assay, such as the assay described herein in Example 2, can be used to assess the extent to which the factor inhibits neurotrophin/receptor binding. Peptide inhibition of neurite survival and outgrowth can be determined using the in vitro assay described by Riopelle et al. (*Can. J. Phys. Pharm.* 60:707 (1982)), exemplified herein in Example 3, or using the in vivo kindling experiment described in Example 5.

The present invention provides factors having the functions of peptide R11 as described below, and methods of inhibiting the effect of a neurotrophin using such a factor. "Functional equivalents" of R11 encompassed by the invention may be peptide or non-peptide compounds. As described in detail below, substitutions may be made to particular residues of R11, resulting in functional differences. Analogues of R11 that have qualitatively the same functions are encompassed by the invention, though there may be minor quantitative differences in efficacy. Such qualitative functions include ability to inhibit or eliminate the effect of a neurotrophin, and particularly ability to reduce the affinity of a neurotrophin for a receptor, such as, for example, a receptor tyrosine kinase, preferably TrkA Such qualitative functions also include ability to disrupt the interaction of neurotrophin promoters, i.e., the factor disrupts the native multimeric conformation of the neurotrophin. Preferably, the factor disrupts the conformation (or native geometry) of a receptor binding domain of the neurotrophin.

"Functional equivalents" of neurotrophin-derived peptides in accordance with the present invention include peptides which differ from a neurotrophin-derived peptide by deletion, replacement or modification of one or more of its amino acids, but which retain the activity of the neurotrophin-derived peptide, i.e., are capable of inhibiting a neurotrophin-mediated activity. For peptide analogues of a neurotrophin-derived peptide in accordance with the present invention, conservative amino acid replacements of native amino acids may be made so that charged or polar residues are substituted for other charged or polar residues, and uncharged or non-polar residues are substituted for other uncharged or non-polar residues. For example, an an arginine residue of the neurotrophin-derived peptide may be replaced with a lysine residue. Deviations from this scheme are encompassed by the invention only so far as qualitative function is retained. Alternatively, a neurotrophin-derived peptide according to the invention may include derivative internal or terminal amino acids, as discussed in more detail herein, to yield a peptide which retains the biological activity of the neurotrophin-derived peptide. Peptide analogues of R11 may be longer or shorter than R11 so long as qualitative function as defined above is retained. Similarly, peptide analogues of R11 according to the invention are not limited to having only the twenty commonly occurring amino acids, and amino acid residues may be modified, so long as R11-like function is maintained.

Moreover, the invention is not limited to peptide analogues of R11. Rather, the invention encompasses any compound having the functional properties described herein. In some embodiments of the invention, the compound is a small molecule. In some embodiments, the compound comprises a polymer portion; any convenient polymer backbone may be employed. In some embodiments, a compound of the invention may be linked to a carrier that later dissociates from or is cleaved (preferably by the cell) from the portion of the compound having R11-like properties.

Morgan and co-workers (Morgan et al., "Approaches to the discovery of non-peptide ligands for peptide receptors and peptidases," In *Annual Reports in Medicinal Chemistry* (Vinick, F. J., ed.) pp. 243–252, Academic Press, San Diego, Calif. (1989), incorporated herein by reference) define peptide mimetics as "structures which serve as appropriate substitutes for peptides in interactions with receptors and enzymes. The mimetic must possess not only affinity, but also efficacy and substrate function." For purposes of this disclosure, the terms "peptidomimetic" and "peptide mimetic" are used interchangeably according to the above-excerpted definition. That is, a peptidomimetic exhibits function(s) of a peptide, without restriction of structure. Peptidomimetics of the present invention, i.e., analogues of R11, may include amino acid residues or other moieties which provide the functional characteristics described herein.

The term "bicyclic" is used herein to refer to a peptide in which there exits two ring closures. The ring closures are formed by covalent linkages between amino acids in the peptide. A covalent linkage between two nonadjacent amino acids constitutes a ring closure, as does a second covalent linkage between a pair of adjacent amino acids which are already linked by a covalent peptide linkage. The covalent linkages forming the ring closures may be amide linkages, i.e., the linkage formed between a free amino on one amino acid and a free carboxyl of a second amino acid, or linkages formed between the side chains or "R" groups of amino acids in the peptides. Thus, bicyclic peptides in accordance with the present invention may be "true" bicyclic peptides, i.e., peptides cyclized by the formation of a peptide bond between the N-terminus and the C-terminus of the peptide, or they may be "depsi-bicyclic" peptides, i.e., peptides in which the terminal amino acids are covalently linked through their side chain moieties.

Practice of the invention will be described in detail below with reference to a particular example, namely disruption of the dimerization of a neurotrophin, nerve growth factor (NGF). However, a person skilled in the art would be able to employ the principles of the invention in regard to other growth factors having a cysteine knot, to other neurotrophins and to multimeric proteins of various sizes, subunit compositions and functions, some examples of which were given above. Although the invention is described in detail below with reference to certain preferred embodiments thereof, these embodiments are offered to illustrate but not to limit the invention. It is possible to make other embodiments that employ the principles of the invention and fall within its spirit and scope.

Part A) R11 and Analogues

FIG. 1 illustrates generally the structure of a neurotrophin. Two reports regarding the crystal structure of NGF (McDonald et al., *Nature* 354: 411–414 (1991); Holland et al., *J. Mol. Biol.* 239: 385–400 (1994)) implicate specific residues shin the conserved regions of the molecule that participate in interprotomeric interactions responsible for dimer integrity of this neurotrophin at physiological concentrations. The present inventors have noted that these include certain residues within the sequences from residue Cys58 to residue Cys68 and from residue Cys108 to residue Cys110; this information was exploited as described below. Intramolecular interactions within the NGF monomer have been demonstrated for two conserved amino acids (67 and 109) and three variable residues (59, 61 and 64). Residues Val109 and Cys110 of NGF have been demonstrated to have interprotomeric interactions at the dimer interface (McDonald et al., *Nature* 354: 411–414 (1991); Holland et al., *J. Mol. Biol.* 239: 385–400 (1994)).

Using the atomic coordinates of the 2.3 Å crystal structure of NGF (McDonald et al., *Nature* 354:411–414 (1991)), the inventors have designed and synthesized a conformationally constrained peptide, designated R11, that incorporates amino acid residues from two domains that appear to be local with respect to each other in native NGF. Linear peptide R11 is a 14-mer having the following primary sequence: $NH_2$-Cys-Gly-Ser-Glu-Val-Pro-Asn-Ser-Ala-Arg-Cys-Cys-Val-Cys-OH (Sequence ID No. 1) The first eleven residues are identical to residues 58 to 68 of NGF, but in the reverse order. (That is, residue 68 of NGF is Cys, residue 67 Gly, residue 66 Ser, and so on.) The COOH-terminal three residues of R11 correspond to residues Cys108-Val109-Cys110 of NGF (Hone desired to mimic the unusual sequence inversion described above, since this C-terminal portion is a palindrome, it may also be described as N-Cys110-Val109-Cys108-C.)

Referring to FIGS. 2 and 5D, linear peptide R11 is designated R11(linear) or R11(l). A single disulfide bond occurs in R11(monocyclic) (R11(m)), as depicted, and two disulfide bonds constrain the bicyclic peptide R11. The structures of SR11 (Sequence ID No. 7) and BR11 (Sequence ID No. 8) used in some assay Systems are also indicated. SR11 has an identical amino acid composition to R11 except that the eleven N-terminal residues have been inverted to the naturally occurring NGF sequence 58–68, versus 6858. BR11 also has the same amino acid composition as R11, except that the CVC domain has been moved to appear at the N-terminus, rather than the C-terminus. In both SR11 and BR11, cyciczation of the Cys residue side chains has been incorporated in a fashion analogous to R11, i.e., the terminal two Cys residues form a disulphide bond and the internal two Cys residues form a disulphide bond.

Figure 5A:
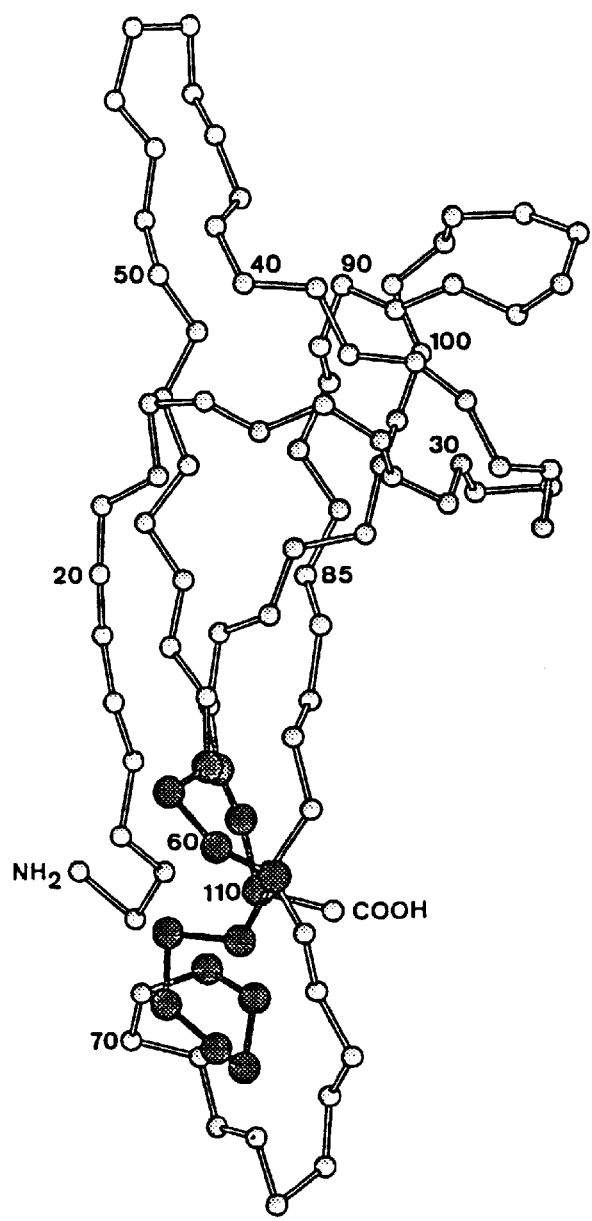
FIG. 5A is a ball and stick diagram of a single NGF protomer viewed from a face-on orientation and FIG. 5B is a 90° rotation, where the right edge of the protomer in B represents the dimer interface (McDonald et al., *Nature* 354: 411–414 (1991)). Amino acid residues 13–111 are illustrated as hollow spheres (location of α-carbon) with residues 58–68 and 108–110 highlighted as larger filled balls.
Figure 5B:
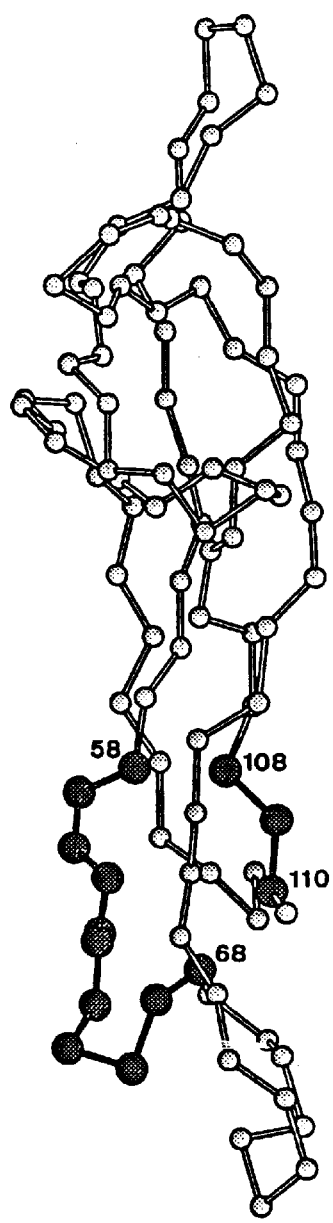
Figure 5C:
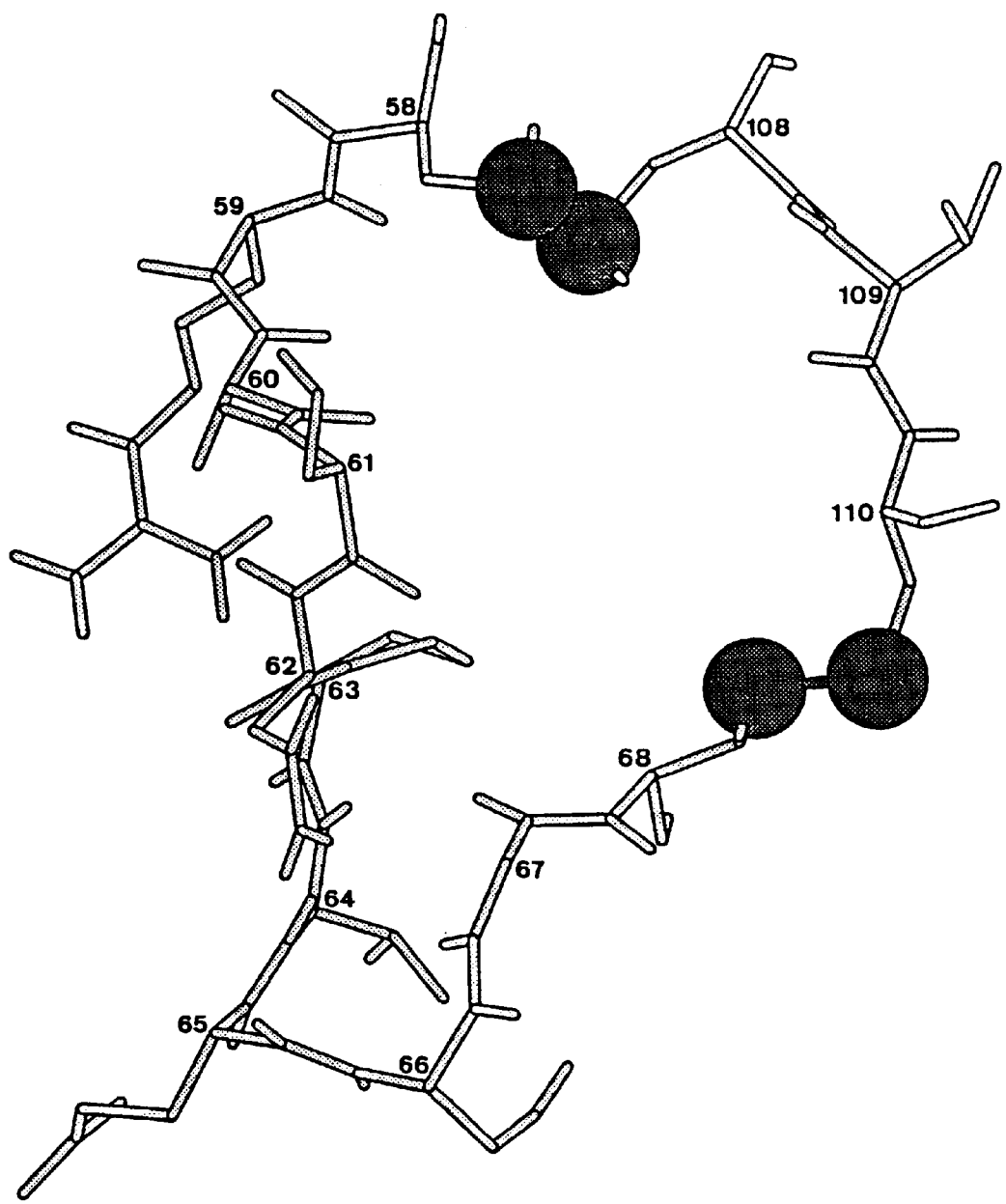
FIG. 5C is a stick diagram of residues 58–68 and 108–110 in isolation from the crystal structure, showing the location of non-hydrogen atoms and the four sulfur atoms (large spheres) participating in two of three disulfide bonds in NGF (formed from Cys58–Cys108 and Cys68–Cys110).

In native NGF, residues 58–68 and 108–110 include residues that are a portion of the dimer interface. The conformation of amino acid residues 58–68 (L3) of native NGF was recognized by the inventors as a target peptide that could be synthesized in a configuration mimicking the conformation of this domain in NGF. In the NGF monomer, Cys58 and Cys68 take part in a cysteine knot motif by forming covalent (disulfide) bonds with Cys108 and Cys110, respectively. This occurs both within the NGF monomer, as shown in FIG. 5A and 5B, and as an isolated structure, as shown in FIG. 5C. As shown in FIG. 5C, the α-amine of Cys58 and the α-amine of Cys108 are in fairly close proximity to each other (4.6 Å).

As illustrated in FIG. 5D, peptide R11 was cyclized by disulfide bond formation between the side chain sulfhydryls of its NH-terminal and COOH-terminal Cys residues, and between the sulfhydryls of the two adjacent internal Cys residues at positions eleven and twelve. These two disulfide bonds mimic the two disulfide bonds of the NGF cysteine knot described above. In addition, R11 is constrained by the additional peptide bond between residues eleven and twelve, which has no counterpart in NGF.

A molecular dynamics study of R11 indicates that the bridge formed by COOH-terminal residues Cys-Val-Cys would yield a conformation in which the interatomic distances between the R11 $NH_2$- and COOH-terminal Cys residues are very similar to the distances observed between residues Cys68 and Cys110 of the NGF crystal structure. The study also indicates that the first eleven residues of R11 would have considerable mobility in solution, consistent with the predicted mobility of residues Cys58–Cys68 in NGF (McDonald at al., Nature 354: 411–414 (1991); Holland et al., J. Mol. Biol. 239: 385–400 (1994)). The four Cys residues of R11 that participate in the two disulfide linkages are much more constrained, however, and molecular dynamics suggest that they would likely exist in a conformation with limited mobility similar to that of the cysteine knot motif in NGF.

The inventors have investigated the ability of two analogues of R11 (SR11 and BR11: FIG. 5D) with differing orientation of the two peptide domains in the NGF dimer disruption assay The analogues SR11, where the Cys58 to Cys68 domain is inverted with respect to the same domain of R11, was equally etude in reducing crosslinking of NGF promoters as R11. The analogues BR11, where the Cys-Val-Cys residues are located at the NH end of the peptide, was not effective in influencing the crosslinking of NGF promoters and did not inhibit NGF-mediated neurite growth at concentrations of 500 μk. Taken together, this data would suggest specific requirements for the orientation of the one Val and four Cys residues in R11 with respect to the interaction with NGF.

Figure 6:
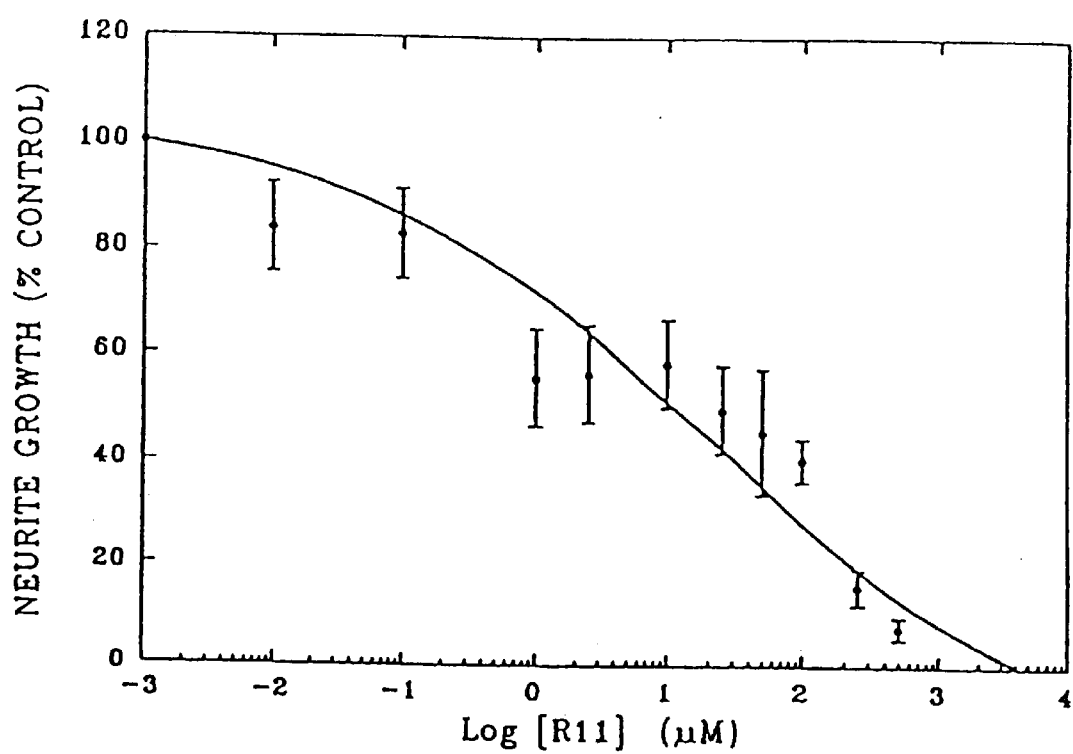
FIG. 6 is a graph showing the ability of R11 to inhibit the activity of NGF in vitro using a biological assay system. R11 inhibited neurite extension with an apparent $IC_{50}$ of 10 µM, displaying a shallow inhibition curve over a wide concentration range. Neither of the less constrained intermediates R11(l) or R11 (m) were effective in blocking NGF-dependent growth when tested in concentrations up to 200 µM. Dissociated cells enriched for sensory neurons were prepared from embryonic day 8 (ED8) chick dorsal root ganglion (DRG) as described (Sutter et al., *J. Biol. Chem.* 254: 5972–5982 (1979)). Neurons were seed into wells of Terasaki plates treated sequentially with poly-D-lysine and laminin at a density of 800–1000 cells/well in "synthetic" Dulbecco's modified Eagle medium (Bottenstein et al., *Proc. Natl. Acad. Sci. USA* 76: 514–517 (1979)) containing 1% fetal calf serum and NGF at 10 µM. The cells were incubated with the additives indicated at 37° C. in a 5% $CO_2$ atmosphere At 18–20 hours, the cells were fixed in 4% formaldehyde in phosphate-buffered saline and scored for neurite growth. The cells on the entire lower horizontal surface of the well were counted using an inverted microscope fitted with phase contrast optics. A neurite was scored if its caliber from origin to terminal was constant and its length was equal to or greater than 1.5 cell body diameters. Neurite growth was corrected for background (no NGF) growth in the presence and absence of peptide. Survival of neurons at 24 hours was not influenced in the presence of 500 µM R11.

Peptide R11 effectively inhibited the neurite growth of embryonic day 8 (ED8) chick dorsal root ganglion (DRG) neurons in vitro (Sutter et al., J. Biol. Chem. 254: 5972–5982 (1979)) with an $IC_{50}$ of 10 μM, as shown in FIG. 6. The dose response profile for the peptide displayed a shallow inhibition curve over a wide concentration range. Such a profile is not typical of a competitive inhibitor. That is, a different dose response profile would be expected if R11 were simply competing with NGF for binding to a receptor. Neither of the less constrained synthetic Intermediates of R11, i.e., R11 (linear) or R11 (monocyclic), was as effective in blocking NGF-dependent neurite growth concentrations up to 200 μM. This indicates that the R11 peptide with its two disulfide bridges has differences in its conformation that lead to differences in its unction. R11 was also shown to inhibit both seizure and mossy fiber sprouting in an animal model of epilepsy whereby repeated subconvulsive electrical stimulation of the forebrain leads to a progressive and permanent amplification of seizure activity (kindling) (Rashid et al., Proc. Natl. Acad. Sci. USA 92: 9495–9499 (199). Indeed we have demonstrated that R11 is an effective antagonist of BDNF and NT-3 in vitro (Rashid et al., Proc. Natl. Acad. Sci. USA 92: 9495–9499 (1995)).

Figure 7A:
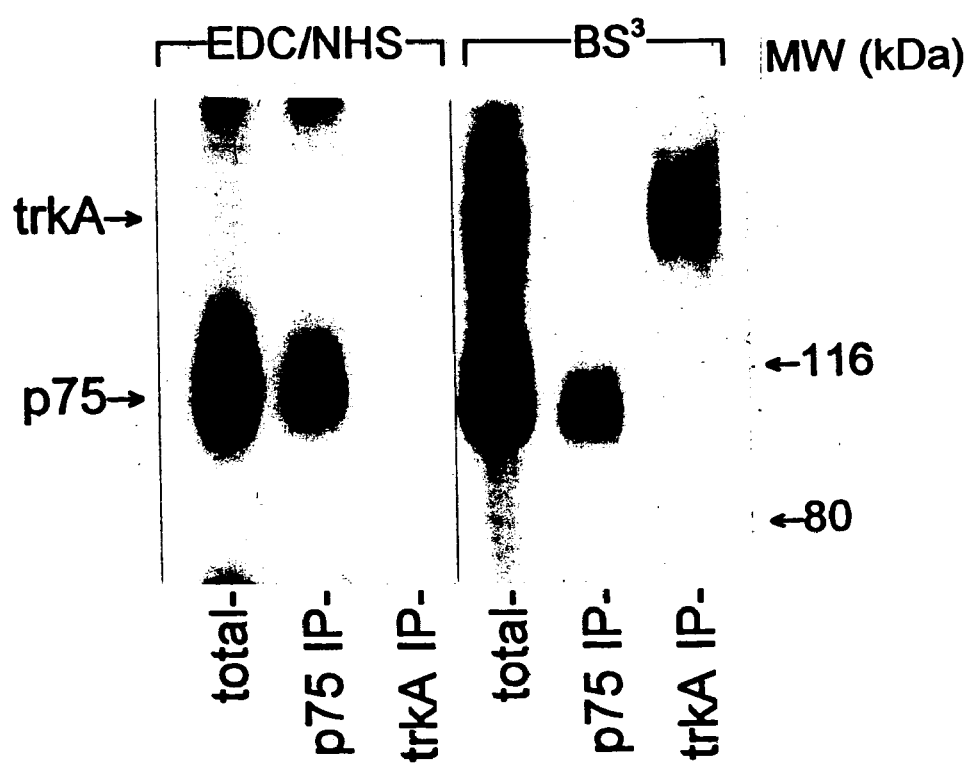
FIG. 7 illustrates autoradiograms (7A and B) and film exposed by chemiluminescence (7C) corresponding to SDS polyacrylamide gels as described in Example 2. The ability of R11 (linear), R11 (monocyclic) and R11 to influence binding of NGF to TrkA and p75 was determined by examining the effects of thes peptides on chemical crosslinking of $^{125}$I-NGF. The TrkA and p75 receptors were crosslinked and identified by immunoprecipitation (A). At peptide concentrations of 200 µM, R11 was most effective at preventing the covalent incorporation of $^{125}$I-NGF into either receptor, followed by R11 (monocyclic) and R11 (linear) (B). The same concentration of R11 was also effective in preventing NGF-dependent phosphorylation of TrkA (C).

The ability of the peptides under study to interfere with binding of NGF to NGF receptors was evaluated by analysis of inhibition of the chemical cross-linking of $^{251}$I-NGF to the common neurotrophin receptor p75 (Chao, J. Neurobiol. 25:1373–1385 (1994)) and the specific NGF receptor TrkA (Barbacid, J. Neurobiol. 25: 1386–1403 (1994)). Immunoprecipitation and polyacrylamide gel electrphoresis of cross linked receptors allowed identification of both receptors, as shown in FIG. 7A. At a concentration of 200 μM, R11 effectively prevented the covalent attachment of $^{125}$I-NGF to each receptor (FIG. 7B); this concentration is similar to that required to block virtually all NGF-mediated neurite growth. At concentrations of 200 μM, neither R11(l) nor R11(m) were able to inhibit greater than 50% of the observed $^{125}$I-labelling.

Rapid NGF-dependent phosphorylation of the TrkA receptor (Kaplan et al., Nature 350: 158–160 (1991)) is mediated by receptor homodimerization-induced autophosphorylation (Jing et al., Neuron 9: 1067–1079 (1992)). Phosphorylation of the TrkA receptor could be detected in NGF-treated PC12 cells within 15 minutes (FIG. 7C) in the absence of R11, but was blocked in the presence of 200 μM R11. A possible explanation is that ligand-induced receptor clustering did not occur. In view of the $^{125}$I-labelling results discussed above, a reduction in or absence of receptor clustering appears to result directly from a reduction in NGF (ligand) binding to its receptor.

Previously, L3 of NGF (residues 62–88) and the NGF $NH_2$- and COOH-terminal domains were implicated in TrkA binding and signalling (Nanduri et al., J. Neurosci. Res. 37: 433–444 (1994)). Whereas R11 could in principle compete directly with L3 for binding to TrkA, thereby producing the results shown in FIG. 7B, in contrast L3 and the $NH_2$- and COOH-terminal domains of NGF have not been implicated in p75 binding (Ibanez, J. Neurobiol. 25: 1349–1361 (1994)), and such a mechanism cannot therefore explain the inhibition by R11 of the interaction of NGF with p75, also shown in FIG. 7B. It should be noted that the same results for p75 were achieved with two different cross-linking reagents, bis(sulfosuccinimidy)suberate ($BS^3$) and a combination of 1-ethyl-3(3-diethylaminopropyl)carbodiimide (EDC) and N-hydroxysulfosuccinimide (S-NHS).

The experimentally observed structure-activity relationships of R11 analogues suggested to the inventors that: i) the Cys-Val-Cys domain may be responsible for biological activity of R11; and ii) the COOH-terminal attachment of the Cys-Val-Cys domain may cause it to adopt bioactive conformation. Accordingly, the inventors analysed low-energy conformations of R11 analogues with both NH2- and COOH-terminal attachment of the Cys-Val-Cys domain, with the aim to determine the geometric features inherent in active molecules.

The low-energy conformations of the following 18 R11 analogues were obtained by Variable Basis Monte Carlo simulated annealing computations combined with a ring closure algorithm.

| I–IX: | $C(A)_nCCVC$ | n = 1 – 9 |
|---|---|---|
| X–XVIII: | $CVCC(A)_nC$ | n = 1 – 9 |

The potential energy function of the molecules included terms for angle bending, torsional distortion, hydrogen bonding, van der Waals interactions and electrostatic interactions as defined in the united atom CHARMM force field.

Figure 9:
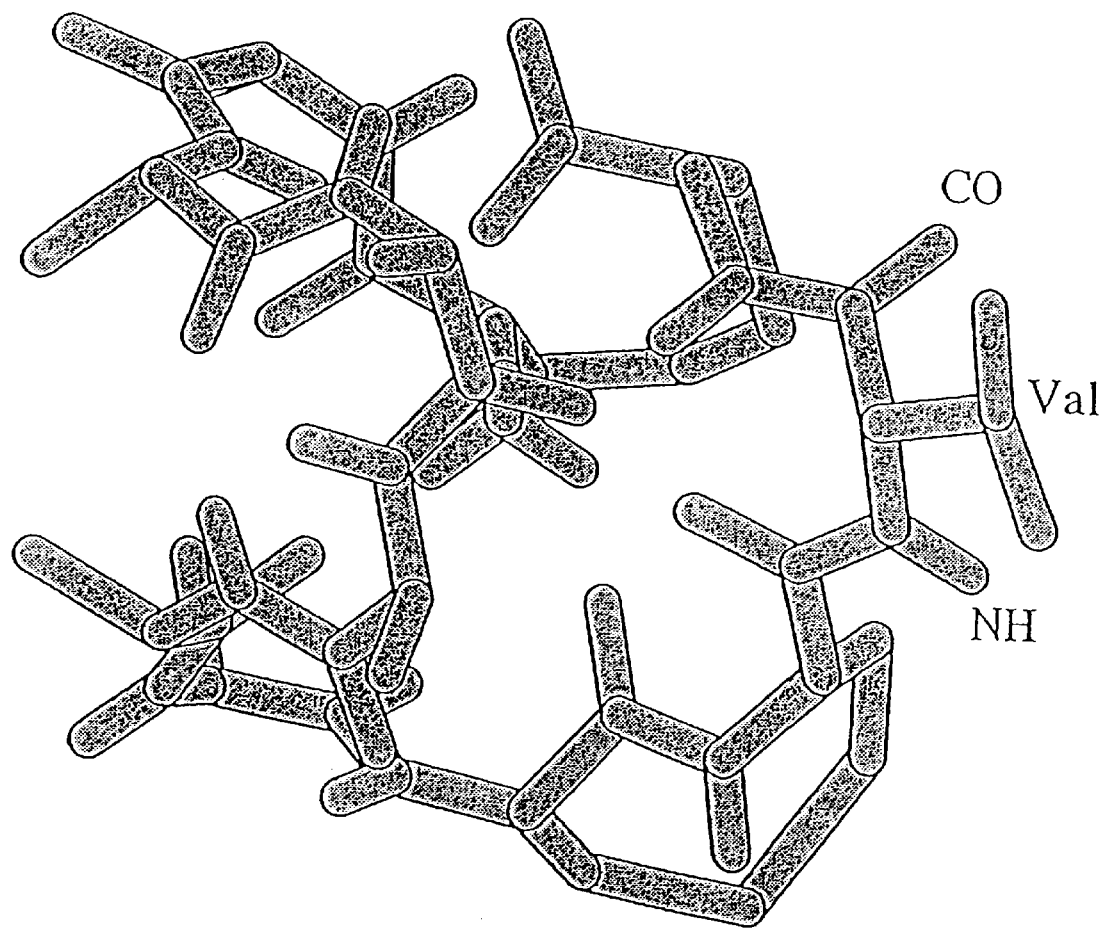
FIG. 9 shows the calculated most stable conformation of molecule VI (CAAAAAACCVC), (Sequence ID No. 9).
Figure 10:
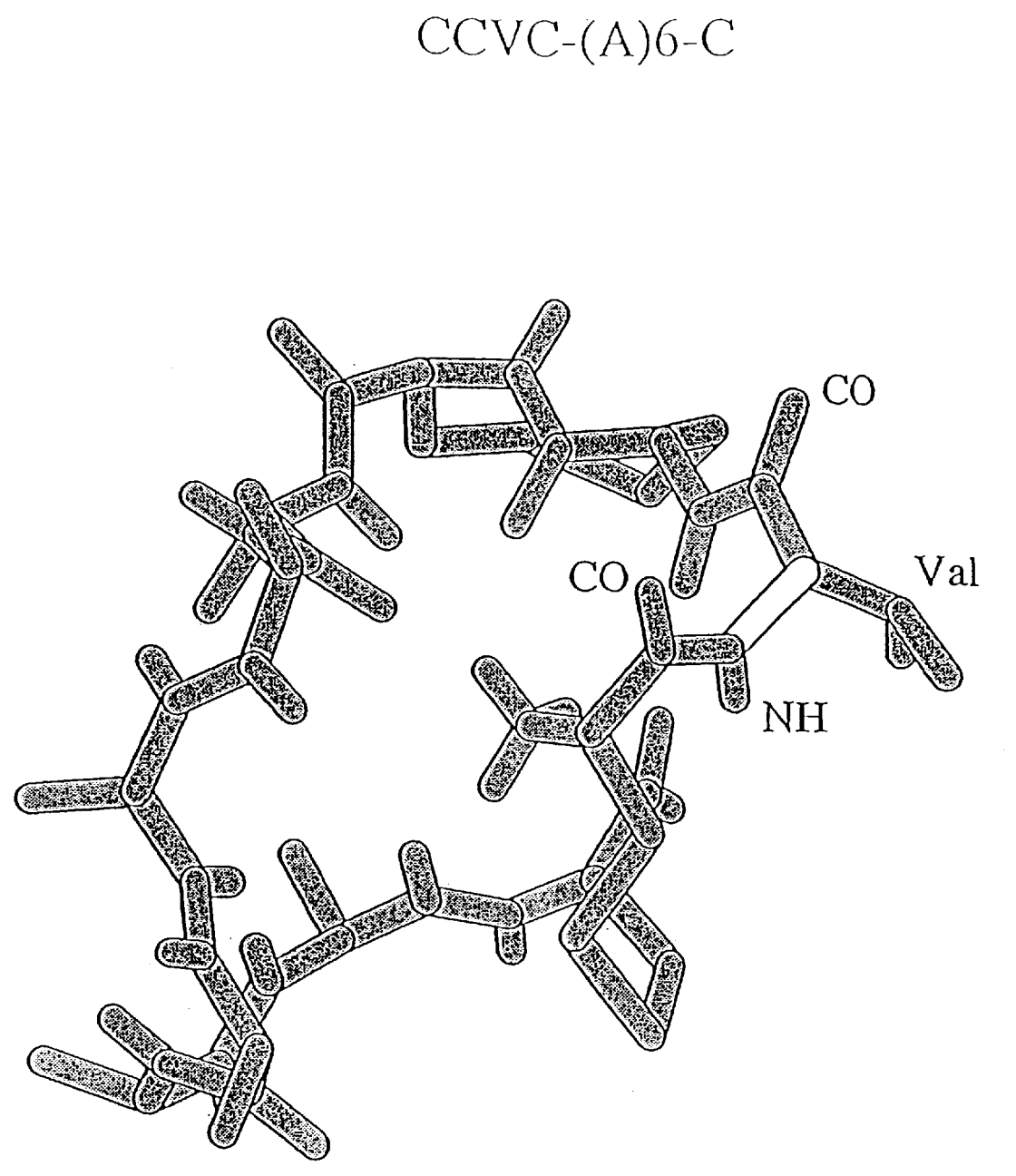

The main result of the molecular modelling is that, beginning with n=5 in the molecules having the Cys-Val- Cys domain at the COOH terminus (i.e., in molecules V–IX), the Cys-Val-Cys domain adopts the same conformation, namely a β-strand conformation. None of molecules X–XVII with the $NH_2$-terminal attachment of the Cys-Val-Cys domain can adopt this particular conformation. The reasons behind the geometric features demonstrated by the molecules in this molecular simulation are apparent in FIGS. 5 and 6. In the molecules having the Cys-Val-Cys domain at the COOH terminus, two disulfide bonds result in formation of a cavity inside the molecule, immediately adjacent to the Cys-Val-Cys domain, and the terminal charged amino group occupies this cavity if the molecule is sufficiently flexible (i.e., if n is sufficiently large). This particular location of the amino group is stabilized by its hydrogen bonding with 4 backbone carbonyl groups which turn inside the cavity. This orientation of the carbonyl groups surrounding the cavity results in both NH and CO groups of the Val residue being exposed in the same direction, which makes the conformation of the Cys-Val-Cys domain consistent with that of a β-strand (FIG. 9). On the other hand, the $NH_2$-terminal attachment of the Cys-Val-Cys domain results in a different H-bond pattern producing a different conformation of this domain (FIG. 10).

Figure 11:
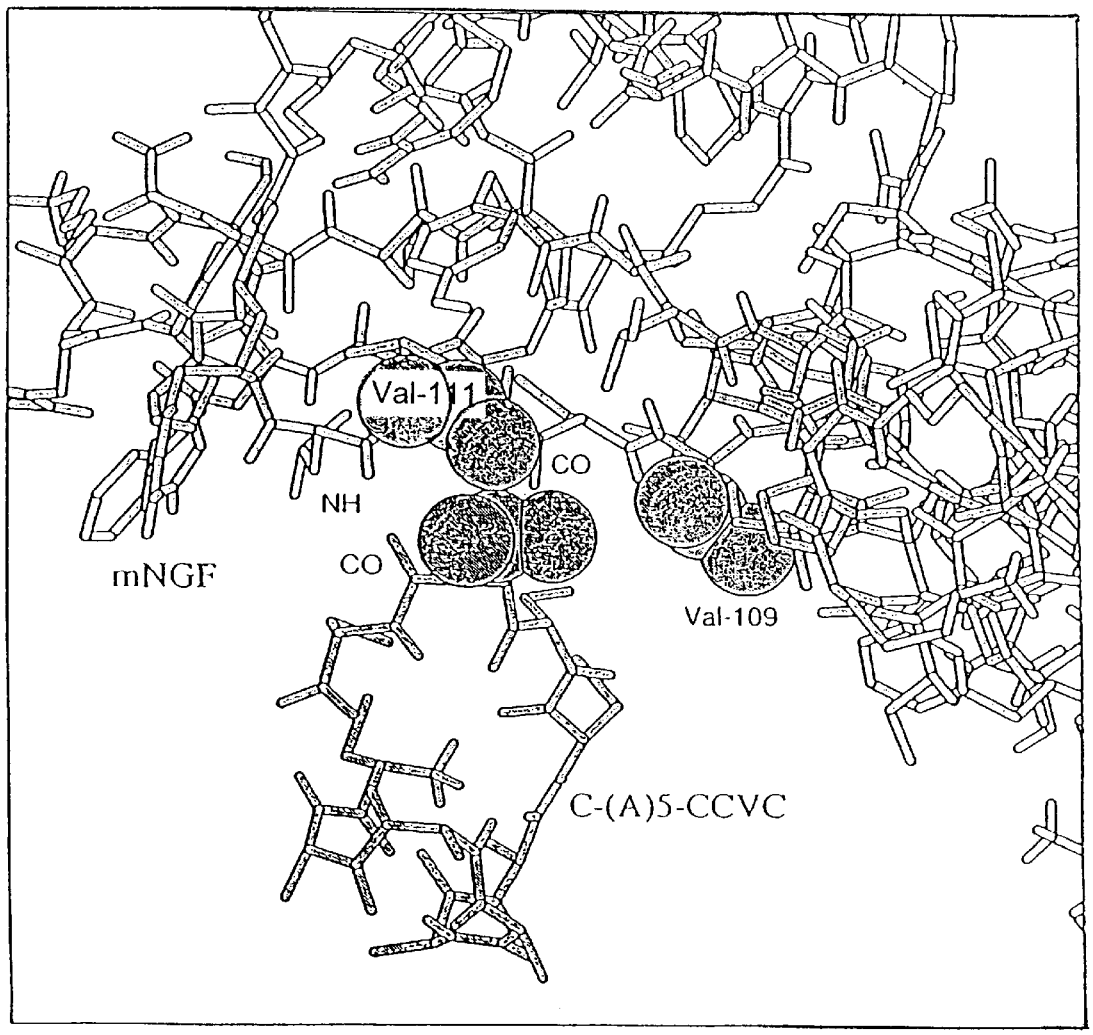
FIG. 11 shows a likely binding interaction of molecule V (CAAAAACCVC) with mouse NGF monomer, (Sequence ID No. 11).

FIG. 11 represents a likely explanation for how the geometric features of molecules V–IX could account for biological activity. According to this model, the β-strand motif of such an R11 analogues forms a hydrogen bond to a parallel β-strand of NGF at Val111. In addition to two H-bonds, there are two hydrophobic interactions of the Val residue of the R11 analogues with Val111 and Val109 of NGF, which stabilizes the R11-NGF complex. This complex alters the dimer interaction of NGF monomers, which decreases biological activity of NGF.

To summarize the conclusions resulting from practice of the invention with respect to NGF, perturbation of NGF dimer structure by R11 is sufficient explanation for lack of chemical cross-linking of $^{125}$I-NGF to either p75 or TrkA receptors, inhibition of NGF-induced stimulation of neurite growth and absence of NGF-mediated TrkA phosphorylation. The inventors believe that the Cy-Val-Cys sequence resembling NGF residues 108–110 at the dimer play a key role in such perturbation.

The identification of a peptide antagonist of NGF that perturbs the dimeric structure of this neurotrophin has important implications for therapeutic strategies involving antagonists of other members of the dimeric neurotrophin family, as well as other multimeric proteins where biological activity depends on association of promoters. The crystal structure atomic coordinates of the promoters in the native protein can be used as reference in the design of an antagonist species that interferes with protomer association. Rather than the antagonist competing directly with the multimeric protein for binding to a substrate, a receptor or the like, the antagonist would perturb protomer association and multimer assembly, presumably in a competitive fashion. Since a functional multimer would be unable to assemble, its biological activity would be reduced or even eliminated. Such approaches can be used to develop antagonists of other members of the cysteine knot family of growth factors notwithstanding the fact that, unlike NGF, both $TGFβ_2$ and PDGF contain interprotomeric disulfide bonds (McDonald et al., *Cell* 73: 421–424 (1993)).

The present invention also relates to bicyclic neurotrophin-derived peptides, or functional equivalents thereof, which inhibit a neurotrophin-mediated activity.

In one aspect, the bicyclic peptide is derived from the internal reverse turn region of the selected neurotrophin. The reverse turn region of a neurotrophin roughly extends from the amino acid at position 58 to the amino acid at position 68, and includes also the region extending from the amino acid at position 108 to the amino acid at position 110, as illustrated in FIG. 1. The "reverse turn" results from the dual linkage occurring in this region. The dual linkage includes a first covalent linkage between the amino acid at position 58 and the amino add at position 108, and a second covalent linkage between the amino ad at position 68 and the amino acid at position 110.

Depsi-bicyclic peptides in accordance with the present invention result from the formation of covalent linkages between the side chains of the amino acids from positions 58, 68, 108 and 10. Preferably, the amino acid residues from these positions have side chains that will readily react to form such covalent linkages. For example, cysteine residues are particularly suitable amino adds for this purpose since the free thiol R groups of cysteine residues readily oxidize to form covalent disulfide bridges. Alternatively, the R groups of the amino acids in these positions can be derivative to yield groups, such as free thiol groups, which will readily react to form the desired covalent linkages. In another alternative, amino adds from positions 58 and 108, and positions 68 and 110, can be selected to have R groups, or derivative to yield R groups, which will form amide linkages. Thus, for example, an amide linkage can be formed between the amino acids from positions 58 and 108 if the amino add at one of these positions yields a free amino group, while the amino acid at the other position yields a free carboxyl group. Examples of amino acids which yield a free amino group suitable for the formation of an amide bond are lysine, asparagine and glutamine. Examples of amino acids which yield a free carboxyl group suitable for the formation of an amide bond are glutamic acid and aspartic acid.

In the case of depsi-bicyclic peptides it will be appreciated that the N- and C-termini remain as free amino and free carboxyl residues, respectively, since it is the side chains of the terminal amino acids which are involved in the covalent cyclizing linkage The free terminal amino and carboxyl groups may also be derivative or altered without affecting the activity of the peptide as an inhibitor of a neurotrophin-mediated activity. For example, the termini may be derivative to include a non-peptidic blocking group Fat will prevent potential degradation at the N- and C-terminal ends from occurring. Such non-peptidic groups include protecting groups such as those conventionally used in the art of peptide synthesis which will not adversely affect the in vitro and in vivo uses of the bicyclic peptide. For example, suitable non-peptidic N-terminal blocking groups can be introduced by alkylation or acylation of the N-terminus. Examples of suitable N-terminal blocking groups include $C_1$–$C_5$ branched or unbranched alkyl groups, acyl groups such as formyl and acetyl groups, as well as substituted forms thereof. Amino acid analogues lacking the amino functionality are also useful to block the N-terminus. Suitable non-peptidic C-terminal blocking groups, in which the carboxyl group of the C-terminus may be either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono and di-alkylamino groups such as methylamino, ethylamino, dimethylamino, diethylamino, methylbutylamino and the like are examples of C-terminal blocking groups. Amino acid analogues lacking the carboxyl functionality are also useful C-terminal blocking groups such as agmatine. Further, it will be appreciated that the free amino and carboxyl groups at the termini can be removed altogether from the bicyclic peptide to yield desamino and descarboxylated forms thereof without e on peptide activity.

True bicyclic peptides are also peptides in accordance with the present invention. Such peptides result from the formation of a peptide linkage between the N-terminal amino group of the amino acid from position 68 and the C-terminal carboxy group of the amino acid from position 110.

Bicyclic peptides in accordance with the present invention may be derived from any mammalian neurotrophin due to the highly homologous nature of neurotrophins among different species with regard to both conformation and amino acid sequence. Thus, the bicyclic peptides may be derived from the 58–68/108–110 amino acid region of, for example, human, mouse or rat NGF. Likewise, the bicyclic peptide may be derived from the 58–68/108–110 region of any mammalian BDNF. In a specific embodiment of the present invention, a bicyclic peptide derived from the 58–68/108–110 region of mouse NGF, as illustrated in FIG. 2, was prepared and found to inhibit rat NGF-mediated activity. In particular, and as set out in detail in the specific examples herein, the bicyclic peptide inhibited cross-linking of NGF to both the $p75^{NTR}$ receptor and the TrkA receptor, and inhibited NGF-mediated neurite outgrowth as determined both in vitro and in vivo.

Thus, specific peptide sequences in accordance with the present invention derived from mouse and human neurotrophins include:

| | | |
|---|---|---|
| $NGF_m$ | $C^{68}$-G-S-E-V-P-N-S-A-R-$C^{58}$-$C^{108}$-V-$C^{110}$ | (SEQ ID NO: 1) |
| $NGF_{hum}$ | $C^{68}$-G-S-D-V-P-N-P-D-R-$C^{58}$-$C^{108}$-V-$C^{110}$ | (SEQ ID NO: 2) |
| $BDNF_m$ | $C^{68}$-G-E-K-T-Y-C-M-P-N-$C^{58}$-$C^{108}$-V-$C^{110}$ | (SEQ ID NO: 3) |
| $BDNF_{hum}$ | $C^{68}$-G-E-K-T-Y-G-M-P-N-$C^{58}$-$C^{108}$-V-$C^{110}$ | (SEQ ID NO: 4) |
| NT-$3_m$ | $C^{68}$-G-N-K-V-P-R-A-E-K-$C^{58}$-$C^{108}$-V-$C^{110}$ | (SEQ ID NO: 5) |
| NT-$3_{hum}$ | $C^{68}$-G-N-K-V-P-R-A-E-K-$C^{58}$-$C^{108}$-V-$C^{110}$ | (SEQ ID NO: 5) |

In one aspect the bicyclic peptide has an amino acid sequence represented generally by formula (I):

$$AA^{68}\text{-G-S-}X_1\text{-V-P-N-}X_2\text{-}X_3\text{-R-}C^{58}\text{-}C^{108}\text{-V-}AA^{110} \text{ (SEQ ID NO: 6)} \quad (I)$$

wherein $AA^{68}$ is selected from cysteine, the descarboxylated form thereof, and a C-terminally blocked cysteine;

$AA^{110}$ is selected from cysteine, desamino cysteine, and an N-terminally blocked cysteine;

$X_1$ is selected from glutamic acid and aspartic acid;

$X_2$ is selected from proline and serine; and $X_3$ is selected from aspartic acid and alanine.

The bicyclic peptides of the present invention may be readily prepared by standard, well-established solid-phase peptide synthesis (SPPS) as described by Stewart et al. in *Solid Phase Peptide Synthesis*, 2nd Edition, Pierce Chemical Company, Rockford, Ill. (1984); and as described by Bodanszky and Bodanszky in *The Practice of Peptide Synthesis*, Springer-Verlag, New York (1984). At the outset a suitably protected amino acid residue is attached through its carboxyl group to a derivative, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis o the oligopeptide is carried out by the removal of the N-protecting group from the initial amino acid, and coupling thereto of the carboxyl end of is the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method which utilizes tert-butyloxycarbonyl as the α-amino protecting group, and the FMOC method which utilizes 9-fluorenylmethyloxycarbonyl to protect the α-amino of the amino acid residues, both methods of which are well known by those of skill in the art.

Recombinant techniques, well-established in the art, can also be used to prepare peptides in accordance with the present invention. DNA encoding the desired peptide is prepared and inserted into an appropriate expression vector. The vector is used to transfect a suitable host organism for production of the peptide. Conventional techniques are then used to culture the host and to isolate the peptide product from the cell culture media.

To ensure that the peptide obtained from either chemical or biological synthetic techniques is the desired peptide, analysis of the peptide composition should be carried out Such amino acid composition analysis may be conducted using high resolution mass spectrometry to determine the molecular weight of the peptide. Alternatively, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Having confirmed the identity of the peptide in linear form, it is then cyclized to form an active bicyclic peptide in accordance with the present invention. Many techniques are available for appropriately cyclizing the peptide, and the protocol used will depend on the type of linkages used to form the bicyclic product. As outlined above, there are numerous covalent linkages which are suitable to cyclize the peptide including, for example, side chain linkages such as disulfide linkages and peptide or amide linkages In one embodiment of the present invention, disulfide linkages were used to form a bicyclic peptide as illustrated in FIG. 2. The internal cysteine residues of the linear peptide were first protected in order to conduct the cyclization reactions in a stepwise fashion. The protected peptide was then air oxidized to allow a disulfide linkage to form between the terminal cysteine residues. Following this cyclization reactions the protecting groups were removed from the internal cysteine residues, and the peptide was again subjected to oxidizing conditions to allow a disulfide linkage to form between the internal cysteine residues thereby resulting in the bicyclic peptide.

Prior to its use to inhibit neurotrophin-mediated activity, the bicyclic peptide is purified to remove contaminants which may adversely affect its activity. In this regard, it will be appreciated that strict standards of purity, such as those required for a pharmaceutical compounds, may not be required for use of the present compounds in vitro. On the other hand, if a compound according to the present invention is to be used in a pharmaceutical sense, it must be purified so as to meet the standards set out by the appropriate regulatory agencies. Any one of a number of conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptides based on their charge.

Bicyclic peptides of the present invention are useful to inhibit or reduce undesirable neurotrophin activity both in vitro and in vivo. Thus, in another aspect of the invention, a composition comprising an effective amount of a neurotrophin-derived bicyclic peptide and a suitable carrier is provided. By "suitable carrier" is meant a carrier which admixes with the selected bicyclic peptide to yield a composition suitable for the application for which it is to be used. By "effective amount" is meant an amount of bicyclic peptide sufficient to inhibit an undesired neurotrophin-mediated activity by about 50% as determined using assays of conventional design such as those described herein in the specific examples.

The present bicyclic peptides have use as media supplements to prevent undesirable neutrophin-mediated activity of neuron cells in vitro. For example, primary sensory neurons require NGF for survival in cell culture; however, NGF also influences neuron differentiation, notably process formation and outgrowth, which are undesirable for the use of primary sensory neurons in cell culture. Thus, to preserve neuron survival in vitro while inhibiting cell differentiation, NGF is added to the cell culture media along with a bicyclic peptide. For addition to the cell culture, the bicyclic peptide is first combined with a carrier which will not adversely affect the growth of the cells in culture. Such carriers will include, for example, physiologically acceptable fluids such as water or any other fluid suitable for addition to the cell culture. Alternatively, the peptide can be combined with media suitable for culturing neuronal cells prior to being added to the cell culture. To be effective to prevent neuron differentiation, the concentration of the peptide in the cell culture will be in the range of from about 100–500 $\mu$M, and preferably from about 200–300 $\mu$M. The optimal concentration of bicyclic peptide for use in preventing neuron differential in cell culture will, of course, vary in each independent case, and will depend on the extent of inhibition desired as well as the type of neuronal cells involved.

Compositions for in vivo administration, e.g., for treating neurological conditions such as epilepsy or Alzheimer's disease, are also contemplated. Such compositions comprise a therapeutically effective amount of a bicyclic peptide together with a pharmaceutically acceptable carrier. In this context, the term "pharmaceutically acceptable" means acceptable for use in the pharmaceutical and veterinary arts, i.e., non-toxic and not adversely affecting the activity of the bicyclic peptide. The term "therapeutically effective amount" means an amount of the compound sufficient to reduce undesirable neurotrophin-mediated activity, as determined using assays of conventional design such as the assays described herein in the specific examples, in an afflicted individual without causing adverse effects.

Pharmaceutically acceptable carriers useful to prepare compositions for in vivo administration include conventional carriers generally selected for combination with peptide-based drugs such as diluents, excipients and the like. Reference may be made to *Remington's Pharmaceutical Sciences*, 17the Ed., Mack Publishing Company, Easton, Pa. (1985), for guidance on drug formulations generally. As will be appreciated, the pharmaceutical carriers used to prepare compositions in accordance with the present invention will depend on the administrable form to be used to treat the afflicted individual.

According to one embodiment of the invention, the compounds are formulated for administration by injection intraventricularly, and are accordingly provided as aqueous solutions in sterile and pyrogen-free form and optionally buffered or made isotonic Thus, the compounds may be administered in distilled water or, more desirably, in saline or 5% dextrose solution. Water solubility of these and other compounds of the invention may be enhanced, if desired, by incorporating into the composition a solubility enhancer, such as cetyltrimethylammonium bromide or chloride. Lyoprotectants, such as mannitol, sucrose or lactose, and buffer systems, such as acetate, citrate and phosphate, may also be included in the formulation, as may bulking agents such as senrm albumin.

Alternatively, the compounds of the present invention may be formulated for administration by routes other than injection. For example, oral dosage forms, such as tablets, capsules and the like, formulated in accordance with standard pharmaceutical practice, may be employed.

For use in treating individuals with a neurological condition, precise dosage sizes of a pharmaceutical composition appropriate for treatment can readily be established in appropriately controlled trials, and will correspond to an amount of bicyclic peptide that reduces undesirable neurotrophin-mediated activity without causing any harmful or deleterious side effects to the individual being treated. It is anticipated that an effective treatment regimen for patients will involve the intraventricular administration of dosages which achieve a level of peptide in the spinal fluid of the individual being treated of about 1–500 $\mu$M. It will be appreciated, of course, that the dosage sizes required to attain this in vivo concentration will vary according to the route of administration, the frequency of administration, on the individual being treated and on the neurological condition being treated.

Specific embodiments of the present invention are described in more detail in the following examples which are not to be construed as limiting.

EXAMPLE 1

Synthesis of Neurotrophin-Derived Bicyclic Peptide

All linear peptides and peptide intermediates in this study were synthesized with an automated peptide synthesizer, e.g., Applied Biosystems model 420 or 430A, and a Wang resin (available from NovaBiochem) using standard 9-fluorenylmethoxxarbonyl chemistry and solid state peptide synthesis methods (Atherton et al., *Solid Phase Peptide Synthesis*, IRL Press, Oxford (1989)). All amino acid side chains were protected with Mtr (4-methoxy-2,3,6-trimethyl benzene-sulfonyl) groups, with the exception of the cysteines from positions 58 and 108 which were introduced as either trityl- or acetamidomethyl-protected (ACM) species. A TFA-cleavage (1–2 h) from the resin yielded the linear peptide retaining only the ACM protecting groups.

The first intrachain disulfide bond formed between deprotected Cys residues at positions 68 and 110 was accomplished by dissolving the peptide in 0.1 M ammonium bicarbonate at a concentration of 0.1 mg/mL and stirring the solution at room temperature while exposed to air. At various times, the progression of the reaction was monitored by sampling the solution and analyzing the reaction products by HPLC separation (Lee et al., *High Performance Liquid Chromatography of Peptides and Proteins*, CRC Press, pp 389–398 (1991)). The HPLC separation was performed on a $C_{18}$ reverse phase column (5μ particle, 300 Å pore; Vydac) using a 1%/min linear gradient of 0.1% trifluoroacetic acid in $H_2O$ to 0.1% trifluoroacetic acid in acetonitrile. The oxidized product containing the disulfide (which eluted at a lower retention time than did the reduced starting material) was purified by HPLC.

The second disulfide bond was formed between the two ACM-protected Cys residues by slowly introducing 0.1 mmol of the peptide R11 (monocyclic) dissolved in 1.5 mL of methanol dropwise into 2.5 mL of 1.0 M $I_2$ in methanol. This was done over 30 min with stirring at room temperature. The stirring was continued (approx 3 h) while the progression of the reaction was determined using HPLC. Upon completion of the cyclization, the reaction was quenched by the addition of solid zinc powder (1–2 mg). The mixture was diluted with 10 mL of water, filtered and lyophilized The bicyclic product of the $I_2$-oxidized acetamidomethyl-protected peptide also eluted earlier in the HPLC gradient and was purified using the method described above. The structure of all peptides was confirmed by amino acid analysis and mass spectroscopy.

EXAMPLE 2

Affinity Cross-linking Experiments

The ability of the peptides derived from the 68–58/108–110 region of NGF to antagonize NGF interaction with the p75 and TrkA receptors was determined The peptides tested were bicyclic (BC) 68–58/108–110, cyclic (C) 68–58/108–110, and linear (L) 68–58/108–110, each of which are illustrated in FIGS. 2 and 5D Receptor cross-linking studies were performed on PC12 rat pheochromocytoma cells (ATCC CRL 1721; Greene et al., *Proc. Natl. Acad. Sci. USA* 73: 2424–2432 (1976)) which were maintained in RPMI1640 (Gibco) supplemented with 10% fetal calf serum (Gibco). Cells were harvested by incubation and trituration in $Ca^{2+}$ and $Mg^{2+}$ free Gey's balanced salt solution, washed and suspended in 10 mM HEPES buffer (pH 7.35) containing 125 mM NaCl, 4.8 mM KCl, 1.3 mM $CaCl_2$, 12 mM $MgSO_4$, 1.2 mM $KH_2PO_4$, 1 g/L sucrose and 1 g/L bovine serum albumin (HEPES Krebs Ringer buffer, HKR buffer) at $10^6$ cells/mL. Subsequent procedures were carried out at 4° C. unless otherwise noted.

For receptor crosslinking, $^{125}$I-NGF was prepared by the method of Sutter et al. (*J. Biol. Chem.* 254: 5972–5982 (1979)) from NGF isolated from mouse submaxillary gland (as described in Mobley et al., *Biochemistry* 15:1543 (1976)) obtained from Cedarlane. The radioiodinated NGF obtained had a specific activity of 60–100 cpm/pg, was stored at 4° C. and used within one week of preparation.

PC12 cells in HKR buffer were incubated with 0.1 nM $^{125}$I-NGF and 200 μM of indicated NGF peptide (one mL total volume) for 2 h at 4° C. Control PC12 cells were incubated in in HKR buffer in the presence of $^{125}$I-NGF only (no NGF peptide).

Figure 7B:
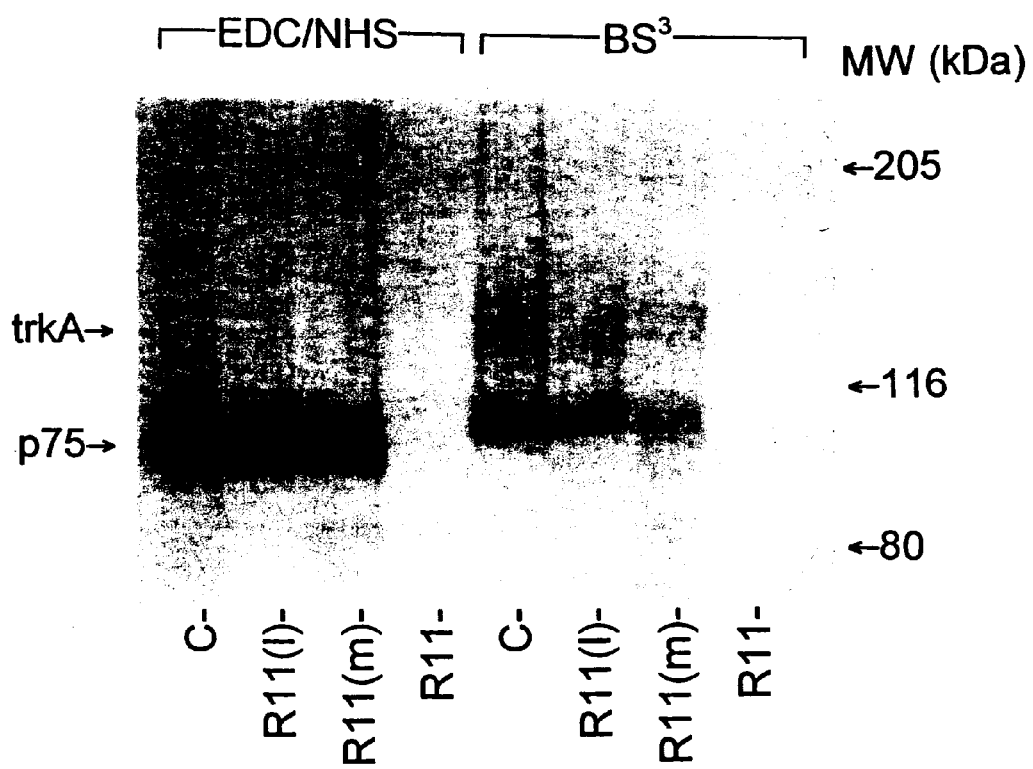

Receptor proteins were cross-linked with either 0.4 mM bis(sulfosuccinimidyl)suberate ($BS^3$, Pierce) for TrkA, or a combination of 2 mM 1-ethyl-3(3-diethylaminopropyl) carbodiimide (EDC) and 2 mM N-hydroxysulfosuccinimide (S-NHS) for p75$^{NTR}$ as indicated. All cross-linking agents (from Pierce) were dissolved in water and added in 20 μL aliquots and the reaction allowed to proceed for 30 min at 25° C. On completion of the cross-linking reaction, the cells were washed three times in HKR buffer with BSA at 4° C. to remove excess free radiolabelled ligand and reagents. The cells were solubilized in 100 μL SDS sample buffer Samples were separated on a modified Laemmli discontinues acrylamide gel system (Laemmli, *Nature* 227:680 (1970)) using 4% SDS-PAGE stacking gel and a gradient urea polyacrylamide separating gel ranging from 4.5% acrylamide/18% urea to 7.5% acrylamide/48% urea. The gels were fixed and processed for autoradiography using −70° C. exposure with Kodak XAR film and manual processing (FIG. 7B).

For positive receptor identification, immunoprecipitation studies were performed. Samples of $10^7$ cells in 1 mL HKR buffer were cross-linked under the conditions described above, washed in HKR buffer and solubilized in non-denaturing lysis buffer (1% NP40, 10% glycerol, 1 mM phenylmethylsulfonylfluoride, 10 μg/mL leupeptin and 0.5 mM o-vanadate in Tris-buffered saline) (Kaplan et al., *Nature* 350:1 158–160 (1991)). The solutions were clarified by centrifugation and immunoprecipitated with either mAb 192 (monoclonal antibody for p75; Cedarlane) or rabbit anti-TrkA, which had been raised against a COOH-terminal peptide of TrkA. The $^{125}$I-NGF cross-linked receptor-antibody complexes were isolated using 50 μL of a 50% solution of rabbit anti-mouse agarose (Sigma; for mAb 192) or protein A-Sepharose (Pharmcia; for anti-Trk) equilibrated in lysis buffer. Immunoprecipitates were washed three times in lysis buffer and the pellets denatured in SDS reducing sample buffer. Rediolabelled receptor preparations were electrophoresed using a discontinues gradient gel where the separating gel gradient varied from 4.0% acrylamidel/8% urea to 10% acrylamide/50% urea. Gels were subsequently fixed, dried and exposed to X-Omat XAR film (Kodak) for autoradiography (FIG. 7A).

The following results were obtained by observing the density of bands (the less the density, the greater the antagonism) appearing on the autoradiograms:

| PEPTIDE | Inhibition of p75 Interaction | | Inhibition Of TrkA Interaction | |
|---|---|---|---|---|
| 1. BC 20 μM | 1. | +[1] | 1. | ++ |
| 2. BC 200 μM | 2. | ++[2] | 2. | ++ |
| C 200 μM | | no inhibition | | no inhibition |
| L 200 μM | | no inhibition | | no inhibition |

[1]+ indicates less than 50% inhibition
[2]++ indicates greater than 50% inhibition Thus, as can be seen from the tabulated results, only the bicyclic peptide was capable of inhibiting NGF interaction at the p75 and TrkA receptors.

EXAMPLE 3

Inhibition of TrkA Phosphorylation by R11

Figure 7C:
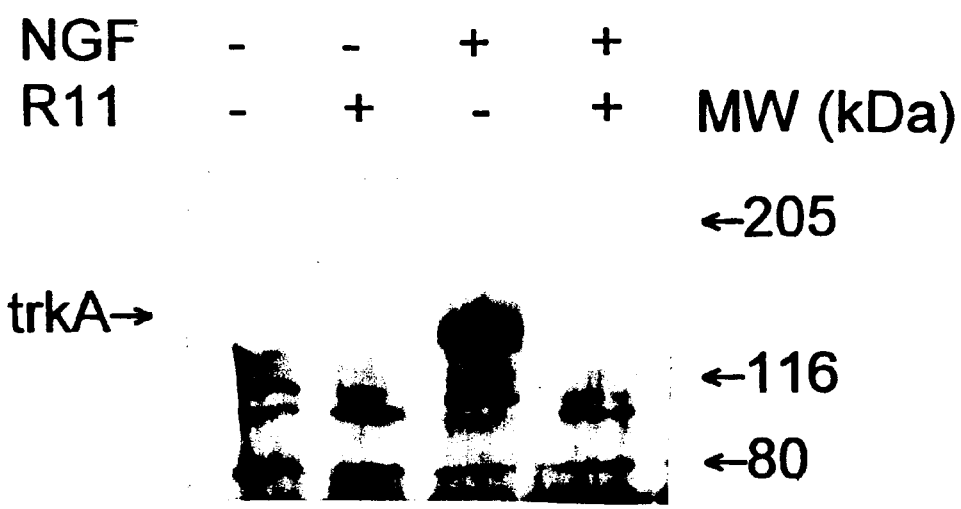

Referring to FIG. 7C, the ability of R11 to influence TrkA phosphorylation was determined by incubating $10^7$ PC12 cells (prepared as described above) in one mL HKR buffer with 50 ng NGF and the indicated concentrations of peptides for 15 min at 37° C. The cells were isolated by centrifugation, solubilized in lysis buffer and the TrkA receptor isolated as described above. The TrkA immunoprecipitated was dissociated in SDS reducing sample buffer and electrophoresed using a 6% polyacrylamide gel. The gel was then transferred to PVDF membrane (BioRad), probed with horseradish peroxidase-conjugated anti phosphotyrosine (RC20; Transduction) and developed using ECL (Amersham). All procedures were carried out according to the manufacturers' instructions.

No basal phosphorylation of the TrkA receptor was observed (lane 1) and R11 had no influence on the basal phosphorylation level (lane 2). NGF induced a dramatic increase in TrkA phosphorylation in the absence of R11 (lane 3). However, in the presence of R11, NGF-induced TrkA phosphorylation was abolished.

EXAMPLE 4

Inhibition of Neurite Outgrowth

Eight-day chick embryo dorsal root ganglia (DRG) were freed of meninges and removed aseptically. The DRG were kept at 4° C. at all times. Ganglia from six embryos (40–50 per embryo) were washed in $Ca^{2+}$ and $Mg^{2+}$ free Gey's balanced salt solution (Gibco) and exposed to 0.01% trypsin (Worthington) in the same solution for 10 min at 37° C. A half-volume of phosphate-buffered Gey's balanced salt solution was added for a further 5 min at 37° C. and the reaction was then stopped with one-third volume of Ham's F12 medium (Gibco) containing 5% fetal calf serum (Gibco). The ganglia were then triturated using a 5 mL narrow-tip pipette to a single cell suspension. Following filtration through 37-μm nylon mesh (Small Parts Inc., Miami, Fla.) in a millipore chamber to remove clumps, the cell suspension was washed through a 500-μl FCS undercut (700×g for 5 min at 4° C.) and resuspended in 4 mL of Ham's F12 medium plus 5% FCS. The cell suspension was then pre-plated on a 100 mm Falcon culture dish and incubated for 45–60 min at 37° C. in a 5% $CO_2$ humidified atmosphere. Cells enriched in neurons were decanted for the bioassay, since non-neuronal cells of DRG preferentially stick to the culture substrate.

The inside wells of 96well Falcon microculture plates were coated with polylysine (0.1 mg/mL) (Sigma) for 4 h at 37° C. (the outside wells were filled with distilled water to provide humidity) and, following a rinse with tissue culture media, 100 μL of neuron-rich cell suspension was added to each well at $10^5$ cells/mL. Ninety (90) μL of NGF solution (prepared in tissue culture media) was then added to each well to a final concentration of 0.25 ng/mL NGF per well. Ten (10) μL of bicyclic 68–58/108–110 peptide solution, i.e., tissue culture media admixed with bicyclic peptide prepared as described in Example 1, was then added to test wells in duplicate to yield wells containing 0 μM, 25 μM, 100 μM and 200 μM peptide. For control assays, 10 μL of Ham's F12 medium was added to duplicate NGF-containing wells. The plates were covered and Incubated in the dark for 24–30 h at 37° C. in a 5% $CO_2$ humidified atmosphere.

The bioassay were read using a Leitz Diavert microscope with phase optics. To afford adequate optics, the meniscus effect of each well was removed by filling the well with a balanced salt solution until a flat, air-filled interface was achieved at the top of the well. At least 100 neurons per well were counted, and the assay was scored as the ratio of cells bearing neurites greater than one cell diameter to total viable (phase-bright) cells.

The results of this assay are illustrated in FIG. 6. In this experiment the $IC_{50}$, i.e., the concentration of bicyclic peptide required to inhibit neurite growth on 50% of the cells, was calculated to be 250 μM.

EXAMPLE 5

Effect of Neurotrophin-Derived Peptide on Kindling

Kindling is a phenomenon in which repeated low-intensity (subconvulsive) electrical stimulation of forebrain areas leads to a progressive and permanent amplification of seizure activity, and is, thus, widely accepted as a model for human temporal lobe epilepsy. The effect of the present neurotrophin-derived peptides on kindling was determined as follows.

Male Long-Evans hooded rats (300–400 g) were used. The animals were housed individually, maintained on an ad lib feeding schedule and kept on a 12 h on/12 h off light cycle. The rats were anaestetised with 0.1 mL per 100 g body weight of 100 mg/mL ketamine hydrochloride (Roger/STB Inc., London, Canada) and 0.05 mL per 100 g body weight of 20 mg/mL xylocaine 2% hydrochloride (Astra, Mississauga, Canada), and then placed in a stereotaxic holder. The rats were implanted unilaterally with a bipolar twisted, teflon coated, stainless steel electrode with an exposed tip (wire diameter 190 μm) in the right amygdala at stereotaxic coordinates of 3.3 mm caudal and 8.0 mm lateral to bregma and 8.5 mm ventral to the brain surface (selected from Paxinos and Watson, *The Rat Brain in Stereotaxic Coordinates*, Academic Press, Sydney (1982)). Following implantation of the electrode, a cannula (Alzet brain infusion kit, Alza Corp.) was implanted in the lateral ventricle, 5 mm below the skull surface, at 0.6 mm caudal to bregma and 1.3 mm lateral to the midline. It was firmly attached to the skull with dental cement and anchored with tee stainless steel screws. An osmotic pump (Alzet model 2002, flow speed 0.5 μL/h, effective maximally for 14 days) was connected to the cannula via polyethylene tubing and placed subcutaneously in the neck area. Histological examination of lateral ventricle sections was done to confirm that the cannula was correctly placed. Forty-five (45) μM of peptide, in a physiologically acceptable buffer, was delivered throughout the duration of the experiment to each test animal. There were five groups of test animals, 5 animals per peptide test group, 10 animals in the negative control group and 12 animals in the positive control group. Each test group was administered one peptide selected from the linear, cyclic and bicyclic 68–58/108–110 peptides. The negative control group was infused with control serum IgGs, and the positive control group was infused with 100 μg/day of anti-NGF antibody. The ant-NGF antibody was obtained from sheep immunized with 0.5 mg of 2.5S NGF (prepared from male mouse salivary glands according to the method of Mobley et al., *Biochemistry* 15:1543 (1976)) intradermally in complete Freund's adjuvant initially, and in incomplete adjuvant every 4 weeks eater. Blood was collected 10 days after each booster injection. Serum was prepared by clotting the blood at room temperature followed by centrifugation at 1,500×g for 30 min, heat inactivation at 56= C. for 30 min. and sterilization using 0.22 μm filters (Nalgene). IgG was purified from serum by differential precipitation using caprilic acid followed by ammonium sulfate (McKinney and Parkinson, *J. Immunol. Methods*, 96–271 (1987)). NGF-specific antibody was further purified using affinity chromatography on 2.5S NGF coupled to CNBr-Sepharose 4B (Pharmacia).

Following a three-day recovery, the kindling stimulations were started. The animals received a one-second train of one-millisecond pulses at a frequency of 60 Hz and a pulse intensity of 200–400 μA. These pulses were sufficient to trigger an epileptiform afterdischarge (AD) following each stimulation. Each animal was stimulated in this fashion twice a day over a period of 11 days. Progression of kindling was monitored behaviorally and electrophysiologically by recording the behavioral seizure stages and the duration and magnitude of afterdischarges. Fully kindled animals exhibited three consecutive stage-5 seizures (Racine, *Electroencephalogr. Clin. Neurophysiol.*, 32:281 (1972)).

Figure 4:
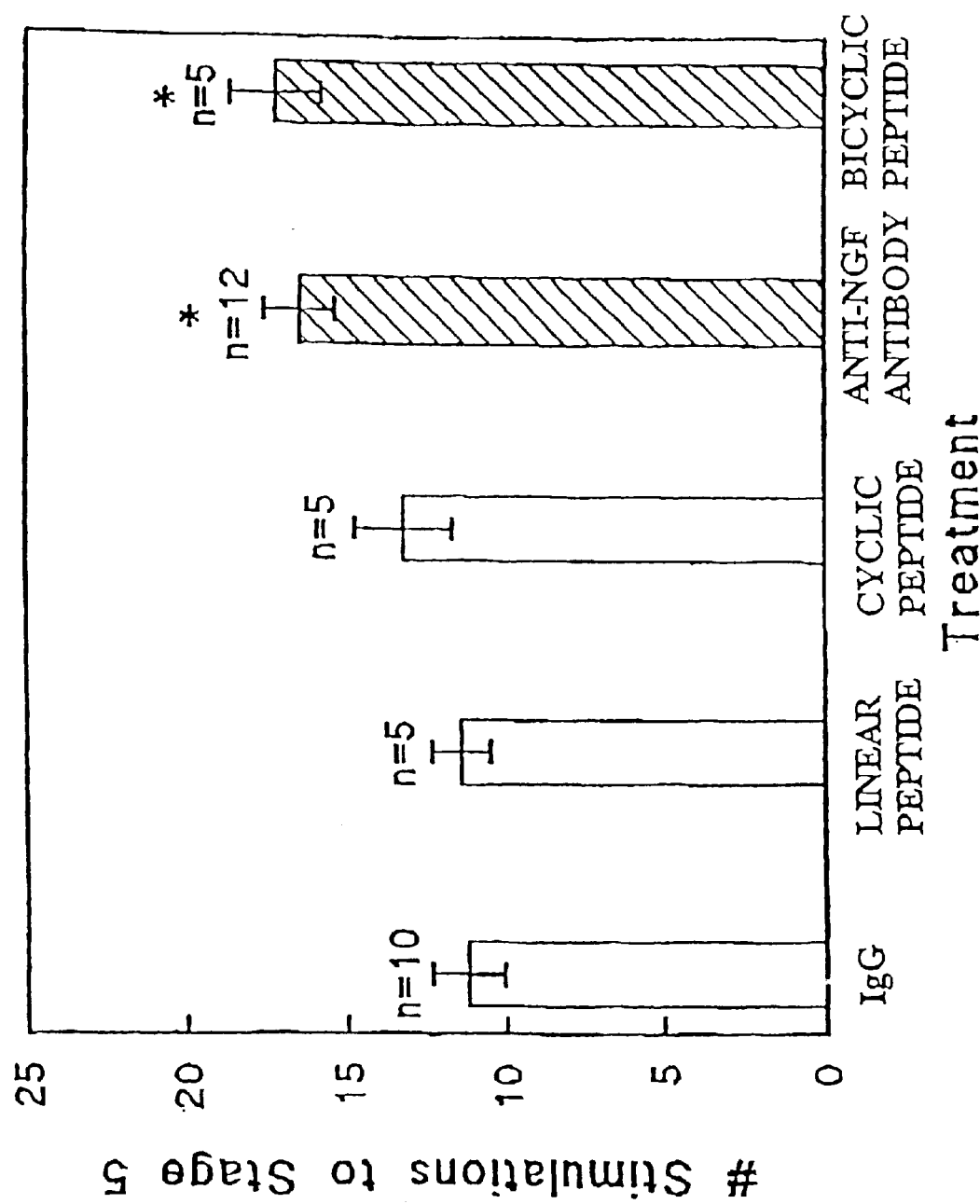
FIG. 4 illustrates the effects of the peptides of FIG. 3 on kindling-induced seizures.

The number of stimulations to reach stage-5 seizures for control rats and rats receiving the linear, cyclic and bicyclic peptides is illustrated graphically in FIG. 4. The results illustrate that the bicyclic peptide has a potency which is approximately equal to that of the anti-NGF IgG in delaying the onset of kindling in comparison to the control serum IgG, linear peptide and cyclic peptide.

EXAMPLE 6

Cross-linking NGF Protomer in a Cell-Free System

Figure 8:
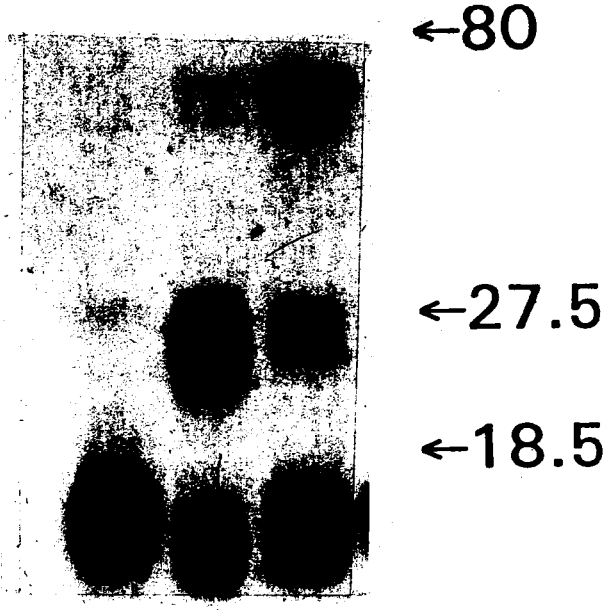
FIG. 8 shows an autoradiogram of SDS polyacrylamide gel as described in Example 5. R11 inhibited the covalent crosslinking of NGF promoters in a cell-free system. Radiolabelled $^{125}$I-NGF (0.5 nM) was incubated in the presence (R11+) or absence (R11−) of 100 µM R11 in HKR buffer at 0° C. for 2 hr in the absence of cells. Cross-linking was performed as described in Example 2 using $BS^3$ ($BS^3$+). Proteins were electrophoresed using SDS-polyacrylamide gel electrophoresis (12% linear gel) and autoradiographed as described. R11 inhibited the cross-linking of NGF promoters as evident by the loss of NGF dimer (at 26 kDa). In presence of R11, NGF protomer cross-linking to BSA (66 kDa) increased dramatically.

The ability of the R11 peptide to influence protomer interactions of NGF was examined, and results are shown in FIG. 8. In the absence of R11, NGF incubated with the protein-protein cross-linking reagent $BS^3$ and subsequently electrophoresed on a polyacrylamide gel under denaturing conditions exhibited a novel band corresponding to two NGF monomers. That is, under denaturing conditions, NGF normally dissociates and electrophoreses as a monomer (FIG. 8, lane 1). In contrast, native NGF dimers that had been covalently cross-linked by $BS^3$ were unable to dissociate and were resolved from free monomer as a more slowly migrating band on the gel (FIG. 8, lane 2). Such cross-linking of NGF promoters was reduced almost to the point of elimination when NGF was incubated in the presence of 100 μM R11 (a concentration that blocked 70% of NGF-mediated neurite growth) and then subjected to $BS^3$, as shown in FIG. 8, lane 3. This result can be explained by a mechanism in which R11 perturbs or disrupts the association of NGF promoters to form the native, functional NGF multimer. This mechanism also explains the biochemical and biological effects of R11 discussed above.

The above-described reactions were performed in buffer containing 1 mg/mL bovine serum albumin (BSA), which should sponge up nonspecific (and presumably low affinity) protein-protein interactions. It can be noted that lane 3 of FIG. 8 shows yet another, still more slowly migrating $^{125}$I-labelled band, whose size is compatible with the sum of the molecular weights of an NGF protomer and BSA This supports the proposed mechanism wherein R11 disrupts NGF dimers, thereby resulting in failure of $BS^3$ to chemically cross-link NGF promoters, and excludes a nonspecific effect of R11 on the efficiency of the $BS^3$ cross-linking reaction. The observations are consistent with an R11-induced conformational alteration in NGF promoters that would be inappropriate for receptor recognition (FIG. 7) but appropriate for chemically-mediated cross-linking to other proteins (e.g., BSA, FIG. 8, lane 3). In the absence of R11, NGF protomer confirmation would favor interprotomer cross-linking (FIG. 8, lane 2).

B) Metals For Multimer Disruption

Translation Metal Ions For Altering Conformation And Inhibiting Biological Activities of Nerve Growth Factor and Related Neurotrophins According to another embodiment of the present invention, the direct actions of the transition metal ion on neurotrophin function have been explored. The inventors demonstrate here that transition metal ions, for example, $Zn^{2+}$ alters the conformation of NGF rendering it unable to bind to $p75^{NTR}$ or TrkA receptors or to activate signal transduction and biological outcomes normally induced by this protein. Similar actions of $Zn^{2+}$ are also observed with other members of the NGF family, suggesting a modulatory role for this metal ion in neurotrophin function.

Although $Zn^{2+}$ and neurotrophins have been implicated in the pathogenesis of neurological disease states, such as stroke (Koh, J.-Y. et al. The role of zinc in selective neuronal death after global cerebral ischemia. *Science* 272, 1013–1016 (1996))., Alzheimer's disease (Rylett, R. J. & Williams, L. R. Role of neurotrophins in cholinergic-neurone function in the adult and aged CNS. *Trends Neurosci.* 17, 490 (1994)), epilepsy (Ben-Ari, Y. & Represa, A. Brief seizure episodes induce long-term potentiation and mossy fiber sprouting in the hippocampus. *Trends Neurosci.* 13, 312–318 (1990); Rashid, K. et al. A nerve growth factor peptide retards seizure development and inhibits neuronal sprouting in a rat model of epilepsy. *Proc. Natl. Acad. Sci. USA* 92, 9495–9499 (1995)), $Zn^{2+}$ inactivation of neurotrophins may mitigate neural cell death via a $p75^{NTR}$ mediated signal (Frade, J. M., Rodriguez-Tébar, A. & Barde, Y.-A. Induction of cell death by endogenous nerve growth factor through its p75 receptor. *Nature* 383, 166–168 (1996), Casaccia-Bonnefil, P., Carter, B. D., Dobrowsky, R. T. & Chao, M. V. Death of oligodendrocytes mediated by the interation of nerve growth factor with its receptor p75. *Nature* 383, 716–719 (1996), and Van der Zee, C. E. E. M., Ross, G. M., Riopelle, R. J. & Hagg, T. Survival of cholinergic forebrain neurons in developing $p75^{NGFR}$ deficient mice. *Science* 274, 1729– 1732 (1996)) under specfic conditions. Further, in cases where activity appears to have detrimental effects (pain, inflammation (Lewin, G. R. & Mendell, L. M. Nerve growth factor and nociception. *Trends Neurosci.* 16, 353–359 (1993); Woolf, C. J. & Doubell, T. A. The pathophysiology of chronic pain—increased sensitivity to low threshold Aβ-fiber inputs. *Curr. Opin. Neurbiol.* 4, 525–534 (1994); McMahon, S. B., Bennett, D. L. H., Priestley, J. V. & Shelton, D. L. The biological effects of endogenous nerve growth factor on adult sensory neurons revealed by a trkA-lgG fusion molecule. *Nature Med.* 1, 774–780 (1994)), cell deaths, inhibition of neurotrophin activity using similar approaches are contemplated to have therapeutic utility.

1) $Zn^{2+}$ $Zn^{2+}$ is a critical component of many proteins and plays a key role in a host of biological processes. In particular, $Zn^{2+}$ serves both catalytic and structural roles in many proteins. Within the central nervous system, certain regions contain relatively high concentrations of $Zn^{2+}$ packaged in presynaptic vesicles (Smart T. G., Xie, X & Krishek, B. J. Modulation of inhibitory and excitatory amino acid receptor ion channels by zinc. *Prog. Neurobiol.* 42, 393–441 (1994)). The release and translocation of $Zn^{2+}$ upon chemical or electrical stimulation has been demonstrated, and concentrations of 100–300 μM at synapses have been reported (Xie, X. & Smart, T. G. A physiological role for endogenous zinc in rat hippocampal synaptic neurotransmission. *Nature* 349, 521–524 (1991)). The ability of $Zn^{2+}$ to interact with a variety of target proteins and peptides has led to the development of several models of disease states where neuronal dysfunction or degeneration may be induced by a $Zn^{2+}$ regulation. Such systems include the interactions of $Zn^{2+}$ with amyloid β protein in the pathogenesis of Alzheimer's disease (Bush, A. I. et al. Rapid induction of Alzheimer Aβ amyloid formation by zinc. *Science* 265, 1461–1487 (1993), modulation of ligand- and voltage-gated ion channels as implicated in epilepsy (Harrison, N. L. & Gibbons, S. J. $Zn^{2+}$: An endogenous modulator of ligand- and voltage-gated ion channels. *Neurophrmacol.* 33, 935–952 (1994)), and a possible role in the neuronal death observed after cerebral ischemia (Koh, J.-Y. et al. The role of zinc in selective neuronal death after global cerebral ischemia. *Science* 272, 1013–1016(1996)).

There is significant overlap between brain regions whose neuronal populations are susceptible to modulation by $Zn^{2+}$ (Harrison et al.) and those regions where nerve growth factor (NGF) levels are increased following insult (Lindvall, O., Kokaia, Z, Bengzon, J., Elmér, E. & Kokaia, M. Neurotrophins and brain insults. *Trends Neurosci.* 17, 490–499 (1994)). As described above, NGF is one member of a family of neurotrophins (including BDNF, NT3, NT4/5) and participates in the differentiation, growth, survival (Levi-Montalcini, R. The nerve growth factor 35 years later. *Science* 237, 1154–1162 (1987)), and regulation of apoptosis (Frade, J. M., Rodriguez-Tébar, A & Barde, Y.-A. Induction of cell death by endogenous nerve growth factor through its p75 receptor. *Nature* 383, 166–168 (1996), Casaccia-Bonnefil, P., Carter, B. D., Dobrowsky, R. T. & Chao, M. V. Death of oligodendrocytes mediated by the interaction of nerve growth factor with its receptor p75. *Nature* 383, 716–719 (1996), and Van der Zee, C. E. E. M., Ross, G. M., Riopelle, R. J. & Hagg, T. Survival of cholinergic forebrain neurons in developing $p75^{NGFR}$-deficient mice. *Science* 274, 1729–1732 (1996)), in a variety of cell systems. It signals responsive cells by interacting with the common neurotrophin receptor $p75^{NTR}$ or the NGF specific receptor TrkA (Chao, M. V. & Hempstead, B. L p75 and Trk: A two-receptor system. *Trends Neurosci.* 18, 321–326 (1995)). Mature NGF is a 118 amino acid protein which exists as a dimer, the structure of which (with the exception of the flexible amino and carboxyl termini) has been determined by X-ray crystallographic studies (McDonald, N. Q. et al. A new protein fold revealed by the 2.3 Å resolution crystal structure of nerve growth factor. *Nature* 345, 411–414 (1991)). Additional structures of a truncated form of NGF missing the eight amino terminal residues, including complexes bound to $Zn^{2+}$, have also been solved (Holland, D. R, Cousens, L. S, Meng, W. & Mathews, B. W. Nerve growth factor in different crystal forms displays structural flexibility and reveals zinc binding sites. *J. Mol. Biol.* 238, 385–400 (1994)). The participation of the NGF amino and carbon terminal residues in TrkA receptor recognition has been established (Bradshaw, R. A. et al. Nerve growth factor: Structure/function relationships. *Protein Science* 3, 1901–1913 (1994), Ibáñez, C. F. Neurotrophic factors: From structure/function studies to designing elective therapeutics. *Trends Biotech.* 13, 217–227(1995), and Shih, A, Laramee, G. R., Schmeizer, C. H., Burton, L. E. & Winslow, J. W. Mutagenesis identifies amino-terminal residues of nerve growth factor necessary for trk receptor binding and biological activity. *J. Biol. Chem.* 269, 27679–27686 (1994)), and a model of the bioactive conformation of the flexible domains of NGF has been described (Shamovsky, I. L., Ross, G. M., Riopelle, R. J. & Weaver, D. F. Theoretical studies on the bioactive conformation of nerve growth factor using VBMC-A novel variable basis Monte Carlo simulated annealing algorithm for peptides. *J. Am. Chem. Soc..* 118, 9743–9749 (1996)). The specific interactions of domains which participate in TrkA recognition have also been proposed by the inventors. While the potential interaction of $Zn^{2+}$ with NGF has been suggested (Holland, D. R, Cousens, L. S., Meng, W. & Mathews, B. W. Nerve growth factor in different crystal forms displays structural flexibility and reveals zinc binding sites. *J. Mol. Biol.* 238, 38954 (1994)), the effects of binding on the conformation of flexible domains of NGF, particularly with respect to receptor recognition, have not been explored.

In the present study a model of a $Zn^{2+}$-induced conformational transition in the NGF amino terminus is developed. The changes in NGF conformation affect receptor binding domains (Shamovsky, I. L., Ross, G. M., Riopelle, R. J. & Weaver, D. F. Theoretical studies on the bioactive conformation of nerve growth factor using VBMC-A novel variable basis Monte Carlo simulated annealing algorithm for peptides. *J. Am. Chem. Soc.* 118, 9743–9749 (1996), and Ibáñez, C. F., et al. Disruption of the low affinity receptor-binding site in NGF allows neuronal survival and differentiation by binding to the trk gene product. *Cell* 69, 329–341 (1992)) and are predicted to inactivate NGF. These considerations have led us to an examination of the effects of $Zn^{2+}$ on the conformation of full length (1–118) mouse NGF and on its biological activities as measured by the binding of $^{125}$I-NGF to $p75^{NTR}$ and TrkA, NGF mediated signalling, survival and toxicity in PC12 cells, and effects on NGF mediated neurite growth of cultured dorsal root ganglion neurons. The studies revel conformational changes and a pronounced inhibition of NGF function by $Zn^{2+}$ at concentrations detected in vivo, consistent with theoretical alterations in NGF structure upon $Zn^{2+}$ binding. As some features of the NGF-$Zn^{2+}$ binding domain are found within other members of the neurotrophin family, the ability of $Zn^{2+}$ to modulate BDNF and NT-3 was also examined. Similar effects of $Zn^{2+}$ on the conformation, receptor binding and biological activity of other neurotrophins were also detected using representative assay systems.

Methods

Molecular Modelling $Zn^{2+}$ cations in natural proteins typically form tetrahedral or pentagonal coordination states with ligands such as cysteine, histidine, aspartate, glutamate and water. In the X-ray structure of des(1–8)octa NGF deletion mutant $Zn^{2+}$ is bound to His-84 and Asp-105, which indicates that the $Zn^{2+}$ coordination is not complete. Missing residues His-4 and His-8 of the flexible amino terminus are the only candidates within the (1–118) NGF structure to accommodate full coordination. To verify this hypothesis, a structure of the $Zn^{2+}$-NGF complex was obtained using the QUANTA V4.1 molecular modelling program (Molecular Simulations Inc.) by multiple molecular dynamics runs of 200–300 ps at moderate constant temperatures of 280–350° K. Followed by local energy refinements. As the "inherent" affinity of transition metals to nitrogen and sulfur atoms (Hancock, R. D. & Martell, A. E. Ligand design for selective complexation of metal ions in aqueous solutions. *Chem. Rev.* 89, 1875–1914 (1989); Gregory, D. S., Martin, A. C. R., Cheetham, J. C. & Rees, A. R. The prediction and characterization of metal binding sites in proteins. *Protein Eng.* 6, 29–35 (1993)) is not accommodated within the CHARMM force field (Brooks, B. P. et al. CHARMM: A program for macromolecular energy, minimization, and dynamics calculations. *J. Comput. Chem.* 4, 187–217), this selectivity has been explicitly "added" to the molecular mechanical potential energy functions. In addition to the united-atom CHARMM potential energy terms, the characteristic distances from imidazole nitrogen atoms of $His4_{[1]}$, $His-8_{[1]}$ and $His-84_{2[2]}$ to $Zn^{2+}$ (about 2 Å (Dent, A. J., Beyersmann, D., Block, C. & Hasnain, S. S. Environment of zinc sites in 5-aminoaevulinate dehydratase. *Physica B* 158, 95–96 (1989)) have been controlled by distance constraints expressed as steep harmonic functions upon any of these values being greater than 2.2 Å. The distance constraints have been used at the molecular dynamics runs only and removed for subsequent energy refinements. Since each of the three His residues has two imidazole nitrogen atoms (Nδ and Nε) able to chelate $Zn^{2+}$, all eight possibilities have been considered. All His residues have been maintained electrostatically neutral.

Since NGF and other neurotrophins fold in a rigid conformation (Robinson, R. C., Radziejewski, C., Stuart D. I. & Jones, E. Y. Structure of the brain-derived neurotrophic factor/neurotrophin-3 heterodimer. *Biochemistry* 34, 4139–4146 (1995)), in addition to the distance constraints, the following atom constraints have been imposed. As the amino and carboxyl termini of NGF are the only significantly flexible domains within the NGF structure (Holland, D. R., Cousens, L. S., Meng, W. & Mathews, B. W. Nerve growth factor in different crystal forms displays structural flexibility and reveals zinc binding sites. *J. Mol. Biol.* 238, 385–400 (1994)), full molecular motions were allowed only for the terminal regions Ser-$1_{[1]}$ to Ser-$13_{[1]}$ and Leu-$112_{[2]}$ to Arg-$118_{[2]}$. Additionally, amino acid side-chain motions were allowed for residues located in the vicinity of His-$84_{[2]}$, namely Glu-$35_{[2]}$, His-$84_{[2]}$, Phe-$86_{[2]}$, Arg-$103_{[2]}$ and Asp-$105_{[2]}$. All other atoms of NGF were fixed at the X-ray crystallographic coordinates (McDonald, N. Q. et al. A new protein fold revealed by the 2.3 Å resolution crystal structure of nerve growth factor. *Nature* 364, 411–414 (1991)).

For conformation and dimer integrity studies, 0.1 nM $^{125}$I-NGF was incubated in the presence or absence of $Zn^{2+}$ in HKR buffer for 2 hours at 4° C. in a total volume of 0.1 ml. For crosslinking NGF promoters, 0.4 mM $BS^3$ was added to the mixture and incubated for 30 minutes at 25° C. The reaction was quenched with reducing SDS PAGE sample buffer, electrophoresed using a linear 15% acrylamide gel and autoradiographed. To assess the dimeric nature of NGF in the presence of $Zn^{2+}$, $^{125}$I-NGF was electrophoresed in a non-reducing SDS PAGE system as described, autoradiographed, and the labelled proteins excised from the gels and counted. For CD studies, NGF (50 μg/ml) was dissolved in 50 mM Tris-HCl buffer and spectra recorded using a computer controlled Jasco J-600 spectropolarimeter. Samples were acquired in the absence or presence of $Zn^{2+}$ (100 μM) at 22° C. in a 2 mm quartz cell averaged over eight scans. Modification of His residues by DEPC was carried out as previously described, where the molar excess of DEPC added and the extent of reaction was determined by evaluating the loss of binding activity of the modified product.

Binding of $^{125}$I-NGF to PC12 cells

Full length (1–118) mouse NGF purified by HPLC from 2.5S NGF (purity greater than 95%) was obtained from Cedarlane Laboratories (Toronto, Ont). The iodination of NGF was performed as previously described (Sutter, A, Riopelle, R. J., Harris-Warrick, R. M. & Shooter, E. M. Nerve growth factor receptors. *J. Biol. Chem.* 254, 5972–5982 (1979)). The $^{125}$I-NGF obtained (typically 80–120 cpm/pg) was purified by size exclusion chromatography on a PD10 column (Pharmacia) pre-equilibrated with HKR buffer (10 mM Hepes [pH 7.35] containing 125 mM NaCl, 4.8 mM KCl, 1.3 mM $CaCl_2$, 1.2 mM $MgSO_4$, 1.2 mM $KH_2PO_4$, 1 g/l, glucose, 1 g/l BSA). PC12 cells were grown in RPMI with 10% heat inactivated donor horse serum and 5% fetal calf serum. Each data point was set up in a single tube containing $^{125}$I-NGF (at the required concentration), 400,000 cells (for a final call concentration of $10^6$/ml), BDNF (at 40 nM for TrkA binding) and NGF (at 10 nM for non-specific binding) as required. The tubes were incubated for 2 hr at 4° C. and 100 μl aliquots (providing triplicate data points for each sample) were transferred to 400 μl microcentrifuges containing 200 μl of 10% glycerol in HKR. Tubes were centrifuged for 2 minutes at 5,000 rpm, the tip containing the cell pellet cut off and radioactivity bound to the cells was determined.

Neurite Outgrowth

Dissosiated cells enriched for sensory neurons were prepared from ED8 chick DRG as described (Dostaler, S. M. et al. Characterization of a distinctive motif of the low molecular weight neurotrophin receptor that modulates NGF-mediated neurite growth. *Eur. J. Neurosci.* 8, 870–879 (1996)). Neurons were seeded at a density of 800–1000 cells/well in Ham's F-12 containing 5% FCS and NGF at 10 pM into wells of Terasaki plates treated with polyysine. The cells were incubated with the indicated additives at 37° C. in a 5% $CO_2$ atmosphere. The cells on the entire lower horizontal surface of the well were scored for neurite growth at 18–20 hours using an inverted microscope fitted with phase contrast optics. A neurite was scored if its caliber from the origin to terminal was constant and its length was equal to or greater than 1.5 cell body diameters. Neurite growth was corrected for background (no NGF).

Survival/Toxicity

Effects of divalent ions on NGF mediated survival and toxicity was evaluated using a colorimetric assay for the lysosomal enzyme acid phosphatase to determine cell number (Connolly, D. T., Knight, M. B., Harakas, N. K, Wittwer, A. J. & Feder, J. Determination of the number of endothelial cells in culture using an acid phosphatase assay. *Anal. Biochem.* 152, 136–140 (1986); Ueda, Y., Walsh, E., Nakanishi H. & Yoshida, K. A. colorometric assay method for the evaluation of neurotrophic activity in vitro. *Neurosci. Lett.* 165, 203–207 (1994)). PC12 cells maintained in serum containing medium do not require NGF for their survival (Mesner, P. W., Winters, T. R. & Green, S. H. Nerve growth factor withdrawal-induced cell death in neuronal PC12 cells resembles that in sympathetic neurons. *J. Cell Biol.* 119, 1669–1680 (1992); Batistatou, A & Greene, L. A. Aurintricarbonic acid rescues PC12 cells and sympathetic neurons from cell death caused by nerve growth factor deprivation: Correlation with suppression of endonuclease activity. *J. Cell Biol.* 115, 461–471 (1991)). To evaluate toxicity, the cells were seeded and maintained without NGF in RPMI with 10% heat inactivated donor horse serum and 5% fetal calf serum in the presence of additives. Loss in viable cell number was determined and expressed as a percent of control. NGF rescues PC12 cells from cell death in serum-free medium(Greene, L. A. Nerve growth factor prevents the death and stimulates neuronal differentiation of clonal PC12 pheochromocytoma cells in serum-free medium. *J. Cell Biol.* 78, 747–755 (1978)). NGF-dependent survival was assessed by harvesting PC12 cells in balanced salt solution followed with washing by 4 cycles of suspension and centrifugation in serum-free RPMI prior to seeding in 96 well plates. After incubation with additives, medium was removed from the wells and cells washed once with 200 μl PBS. Buffer containing 0.1M sodium acetate pH 5.5, 0.1% Triton X-100 and 10 mM p-nitrophenyl phosphate (Sigma 104 phosphatase substrate) was added to each well (100 μl). Plates were incubated at 37° C. for 3 hours. The reaction was stopped by the addition of 10 μl/well of 1N sodium hydroxide and the color development measured at 405 nm using a microplate reader. The relationship between cell number and enzyme activity was linear over the range 1000 to 15,000 cells.

trkA Phosphorylation

The extent of NGF dependent TrkA phosphorylation was determined by a modification of the method described (Kaplan, D. R., Matin-Zanca, D. & Parada, L. F. Tyrosine phosphorylation and tyrosine kinase activity of the trk proto-oncogene product induced by NGF. *Nature* 350, 158–160 (1991), and Kaplan, D. R, Hempstead, B. L, Martin-Zanca, D., Chao, M. V. & Parada, L. F. The trk proto oncogene product: a signal transducing receptor for nerve growth factor. *Science* 252, 554–558 (1991)). $Zn^{2+}$ and/or other additives were allowed to equilibrate with NGF for 2 hours at 4° C. prior to addition of cells. PC12 cells were used at $10^6$ cells/ml and incubated with 40 pM NGF for 15 minutes at 37° C. At the conclusion of the reaction, cells were washed, lysed in TBS containing 10% glycerol, 1% Triton X-100, 1 mM PMSF, 10 $\mu$g/ml aprotinin, 1 $\mu$g/ml leupeptin and 500 $\mu$M orthovanadate (lysis buffer, $10^8$ cells/ml). The cellular debris was removed by centrifugation and the soluble proteins incubated with an anti-TrkA cytoplasmic domain antibody. Antibody complexes were isolated by incubating with immobilized protein G (Pierce Ultralink; 70 $\mu$l of a 50% slurry) for 2 hours at 4° C. The solid phase was washed extensively with lysis buffer and the pellet dissolved in SDS sample buffer. Proteins were resolved using 6% SDS PAGE and Western analysis performed with anti-phosphotyrosine 4G10 (UBI) visualized with ECL (Amersham).

BDNF and NT-3 Studs

Human recombinant BDNF and human recombinant NT-3 were obtained from Alomone Laboratories (Israel). The iodination, crosslinking, and binding experiments using BDNF and NT-3 were performed using the methods described above for NGF. Neurite outgrowth assays were performed as described in the presence of 4.0 nM NT-3 or 8.0 nM BDNF.

Results

Figure 12A:
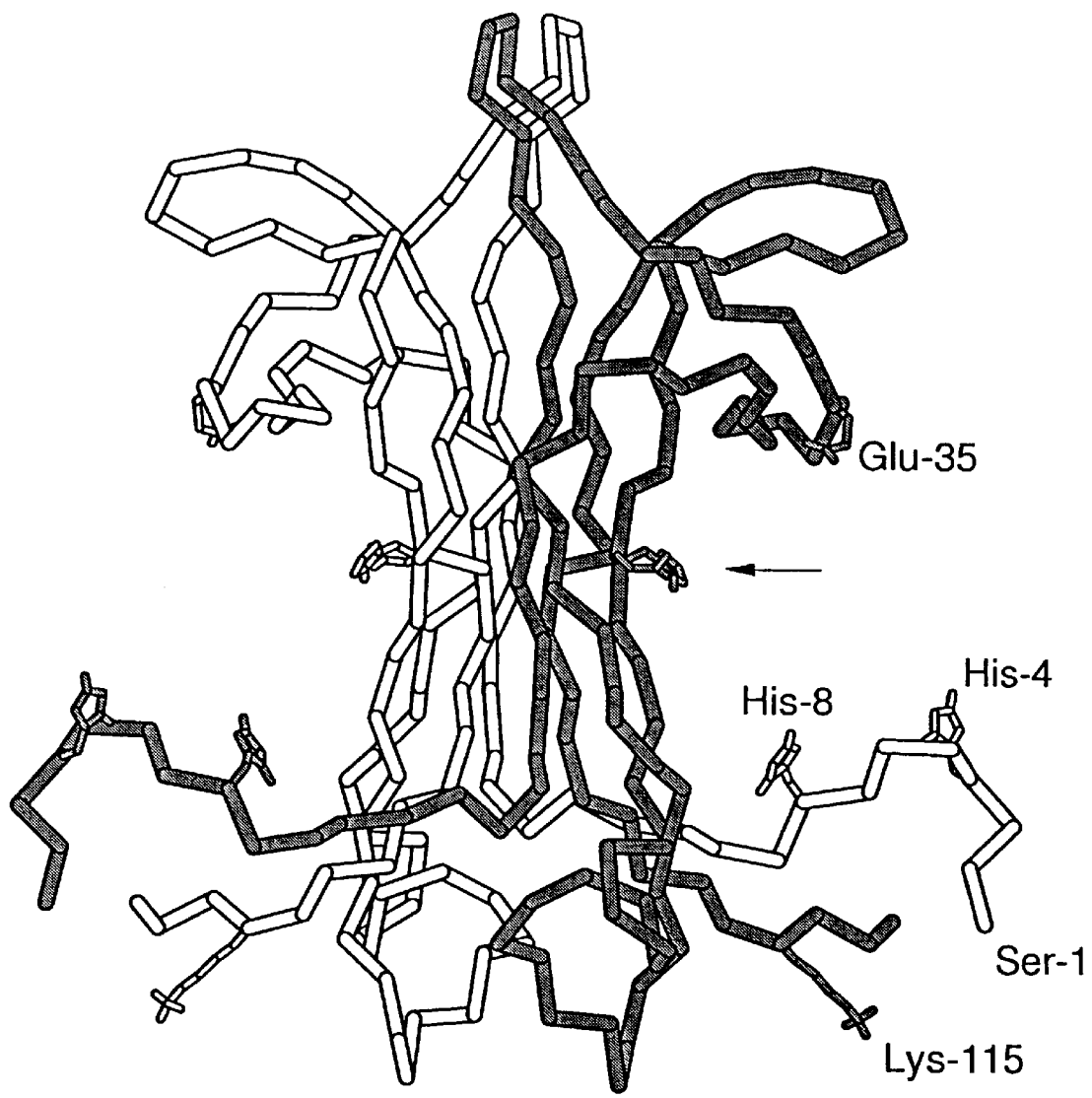
FIGS. 12A–B shows the most stable conformations of NGF (a) and $Zn^{2+}$-NGF (b) as determined by molecular modelling. Each monomer of NGF is illustrated as an αcarbon backbone trace with side chains included for residues referred to within the text. The two monomers (monomers white, monomer$_{[2]}$ gray) are identical, and complementary interactions are expected for $Zn^{2+}$ (black sphere) binding to both sides of the NGF molecule. The arrow indicates the $Zn^{2+}$ binding site as revealed by X-ray crystallographic studies (Holland et al., *J. Mol. Biol.* 238: 38500 (1994)), and the location of the side chains of Asp-105$_{[2]}$ and His-84$_{[2]}$.
Figure 12B:
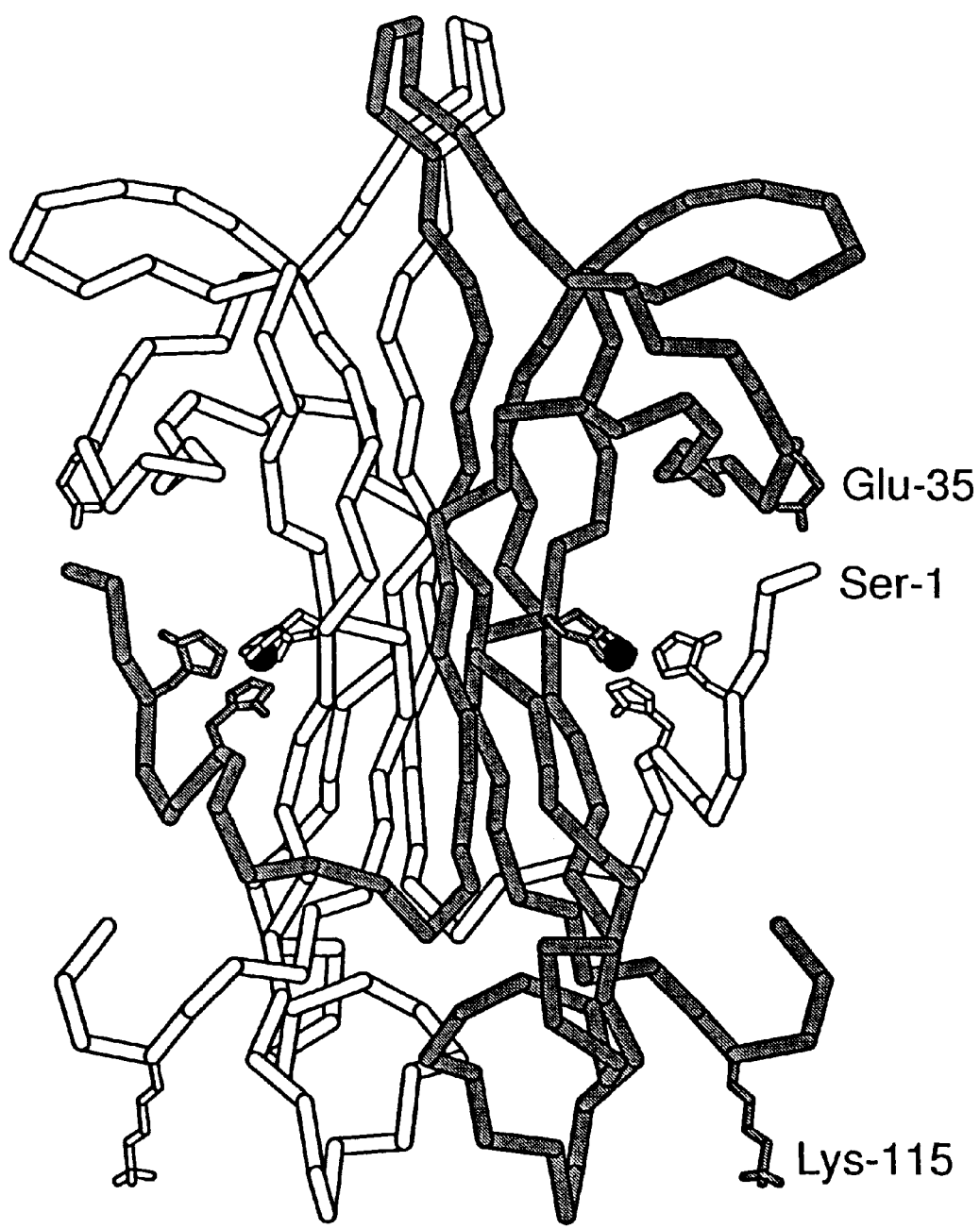
Figure 13:
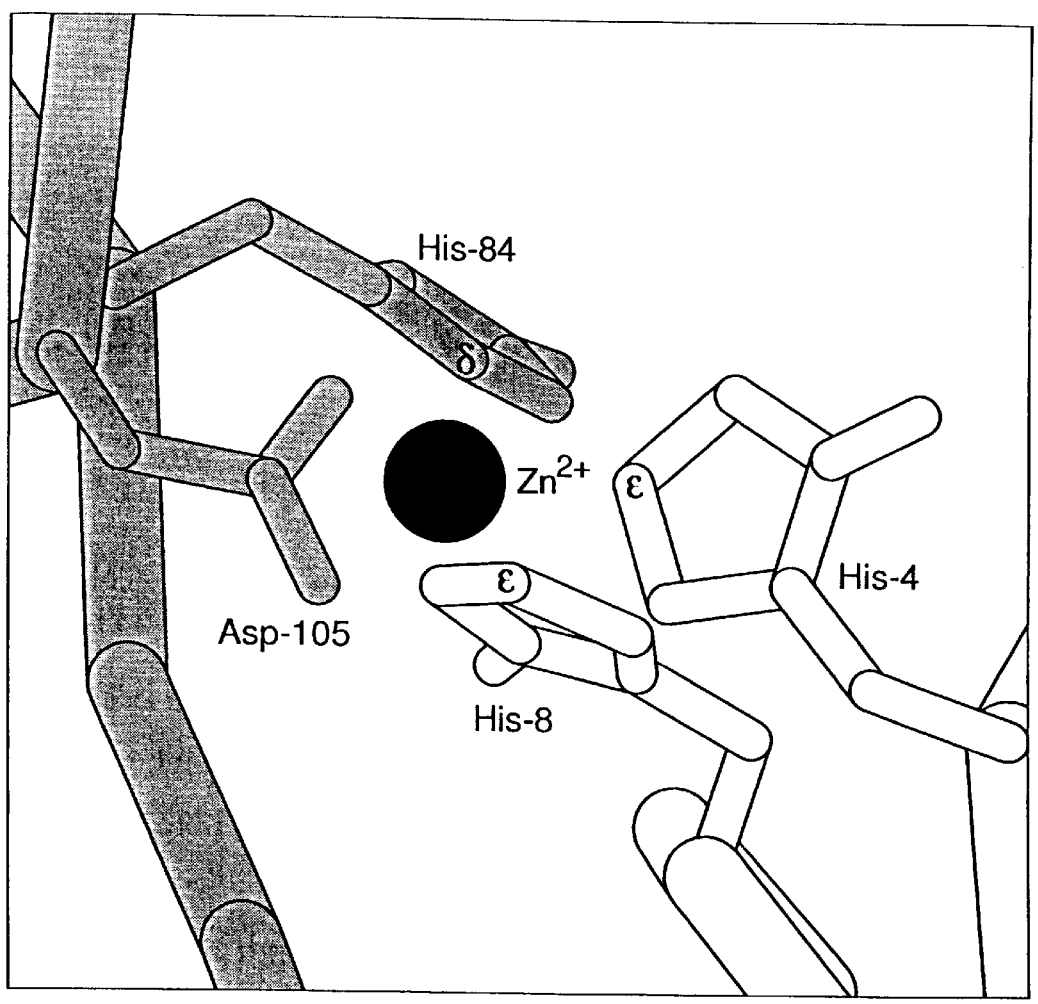
FIG. 13 is a detail of a putative $Zn^{2+}$ binding site in NGF. In this structure, $Zn^{2+}$ is liganded with side chains of three His ($4_{[1]}$, $8_{[1]}$ and $84_{[2]}$) and one Asp ($105_{[2]}$). Greek letters denote chelating imidazole nitrogen atoms. X-ray diffraction studies on atrolysin C (Zhang et al., Protein Data Bank, Brookhaven National Laboratory, Upton, N.Y., accession no. 1ATL), another $Zn^{2+}$ binding protein, revealed the same distorted square pyramidal coordination state in which $Zn^{2+}$ is chelated by three His imidazole nitrogens and two carboxy oxygens. The interatomic distances between $Zn^{2+}$ and chelating nitrogens and oxygens in the $Zn^{2+}$-NGF complex are 2.16±0.08 and 1.99±0.01 Å, respectively, whereas in atrolysin C, they are 2.04±0.04 and 2.17±0.02 Å, respectively. Similar to the $Zn^{2+}$ coordination environment in atrolysin C, both carboxyl oxygens and liganding imidazole nitrogens of His-$8_{[1]}$ and His-$84_{[2]}$ lie within a plane, whereas Nε of His-$4_{[1]}$ is above by 2.20 Å, displacing the $Zn^{2+}$ cation by 0.16 Å above the plane.

In the most stable structure of the $Zn^{2+}$-NGF complex obtained by molecular modelling (FIG. 12b), $Zn^{2+}$ is chelated by a total of four residues from the two monomers, and forms a distorted square pyramidal coordination state with donor atoms N$\epsilon$ of His-$4_{[1]}$, N$\epsilon$ of His-$8_{[1]}$, N$\delta$ of His-$84_{[2]}$ and both $\delta$-oxygens of Asp-$105_{[2]}$ as detailed in FIG. 13. As a result of this chelation, conformation of the amino terminus of NGF is considerably changed (compare FIG. 12 a and b). In the presence of $Zn^{2+}$ the Ser-$1_{[1]}$ $\alpha$-amine is detached from the carboxyl terminus and forms an ionic hydrogen bond (salt bridge) with the Glu-$35_{[2]}$ side-chain, which further stabilizes the structures. As a consequence of the predicted conformational changes, the distance between primary amines of Lys-$115_{[2]}$ and the Ser-$1_{[1]}$ amino terminus (a putative crosslinker site) is no longer within the spanning distance of bis[sulfosuccinimidyl]-suberate ($BS^3$) (FIG. 12b).

Figure 14A:
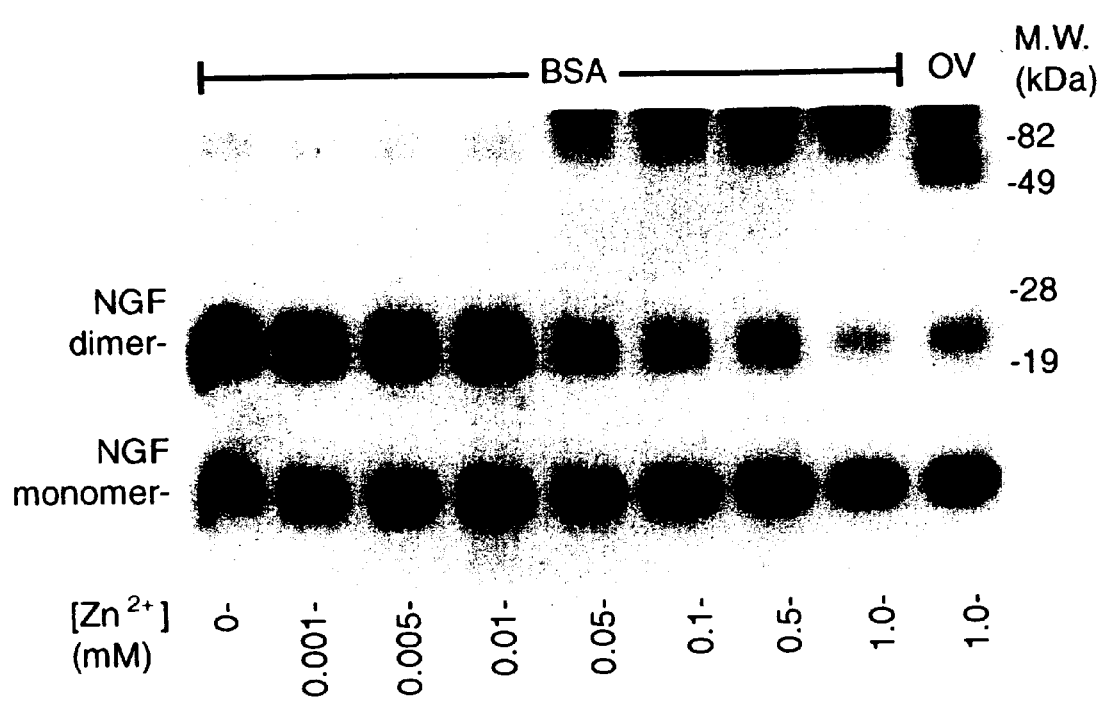
FIGS. 14A–D illustrates that $Zn^{2+}$ alters the conformation of NGF. (a) Changes in the conformation of NGF as demonstrated by reduced ability of $BS^3$ to covalently crosslink NGF monomers in the presence of $Zn^{2+}$. The crosslinked NGF dimer (26 kDa) is not dissociated under reducing conditions; NGF monomer (13 kDa) arises from NGF dimer which is not covalently crosslinked due to reaction efficiency. The reduced ability of NGF monomers to be crosslinked in the presence of $Zn^{2+}$ is accompanied by enhanced crosslinking to other proteins in the buffer (BSA or ovalbumin; OV) as indicated. (b) Alterations in NGF conformation in the presence of $Zn^{2+}$ were evident by CD spectroscopy. A significant decrease in the mean molar elasticity (e) was detected in the presence of $Zn^{2+}$, representing an increase in peptide asymmetry. (c) The effect of $Zn^{2+}$ on stability of the NGF dimer was evaluated using non-reducing conditions as described (Woo et al., *J. Biol. Chem.* 271: 24433–24441 (1996)), results indicate the mean±SD from 2–4 independent experiments (d) Chemical modification of His residues altered protomer crosslinking efficiency. The effect of $Zn^{2+}$ on crosslinking of intact NGF (A), was abolished when His residues were chemically modified by DEPC (B).
Figure 14B:
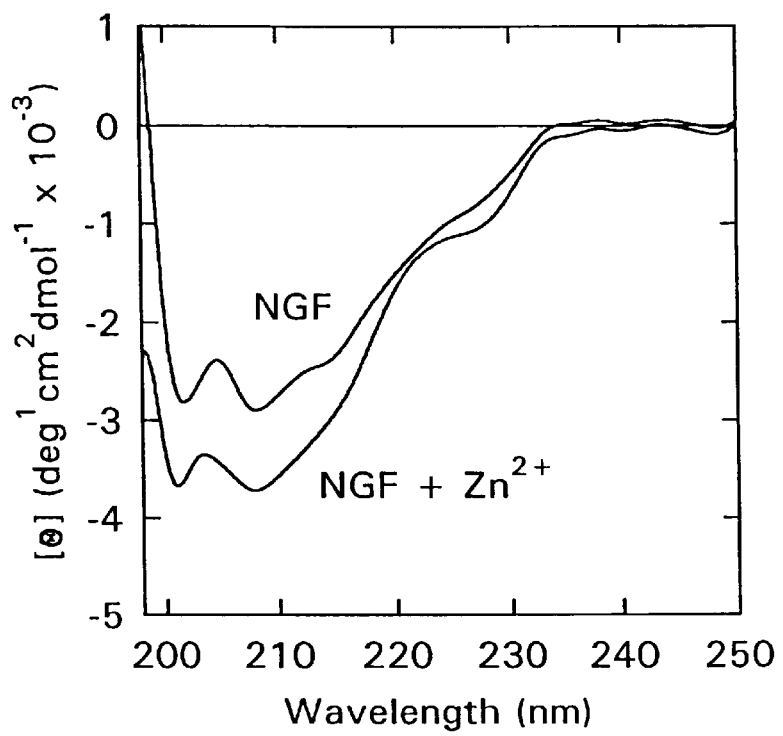
Figure 14C:
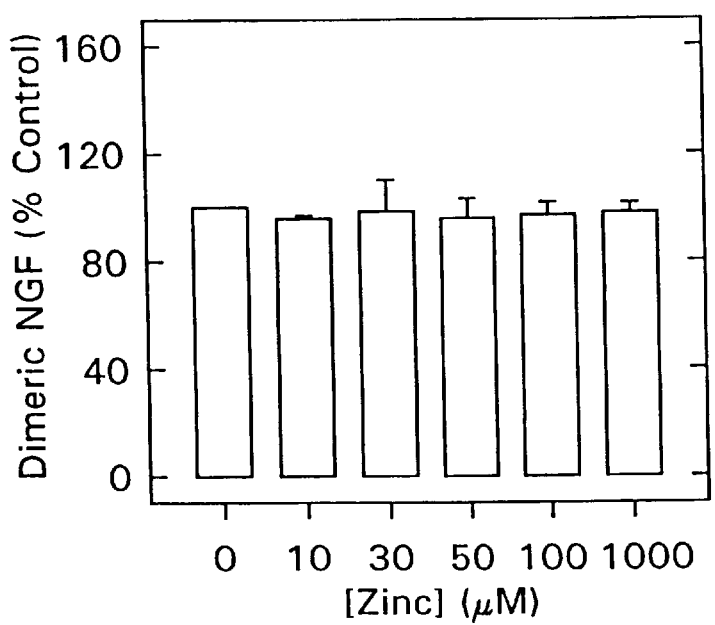

To examine NGF conformation, the ability of $BS^3$ to covalently crosslink NGF monomers was determined NGF monomer crosslinking was inhibited in the presence of $Zn^{2+}$ (FIG. 14a), and importantly, crosslinking of $^{125}$I-NGF to larger complexes was promoted, demonstrating that the effects of $Zn^{2+}$ on protomer crosslinking were not a result of altered cross-linker efficiency. The higher molecular weight crosslinked complexes observed in the presence of $Zn^{2+}$ were complexes of NGF and carrier proteins present in the buffer (i.e. BSA or ovalbumin) as demonstrated by substituting these proteins. The ions $Ca^{2+}$ and $Mg^{2+}$ had no effect on crosslinking efficiency and CaEDTA prevented the $Zn^{2+}$ effects. Alterations in NGF conformation in the presence of $Zn^{2+}$ were further confirmed using circular dichroism (CD; FIG. 14b). Changes in the molar residue ellipticity ($\Theta$) of NGF in the presence of $Zn^{2+}$ were observed, consistent with an increased peptide bond asymmetry and altered conformation upon interaction with the ion. The ability of $Zn^{2+}$ to alter conformation suggests either alterations within NGF monomers and/or a decrease in dimer stability. To test the latter possibility, non-reducing gel electrophoresis of $^{125}$I-NGF was performed in order to assess the dimer stability in the presence of $Zn^{2+}$ (Woo, S. B. & Neet, K. E. Characterization of histidine residues essential for receptor binding and activity of nerve growth factor. *J. Biol. Chem.* 271, 24433–24441 (1996)). No change in the percentage of NGF migrating as a dimer in non-reducing gel electrophoresis conditions was detected, indicating that $Zn^{2+}$ does not alter the stability of the NGF dimer (FIG. 14c).

Figure 14D:
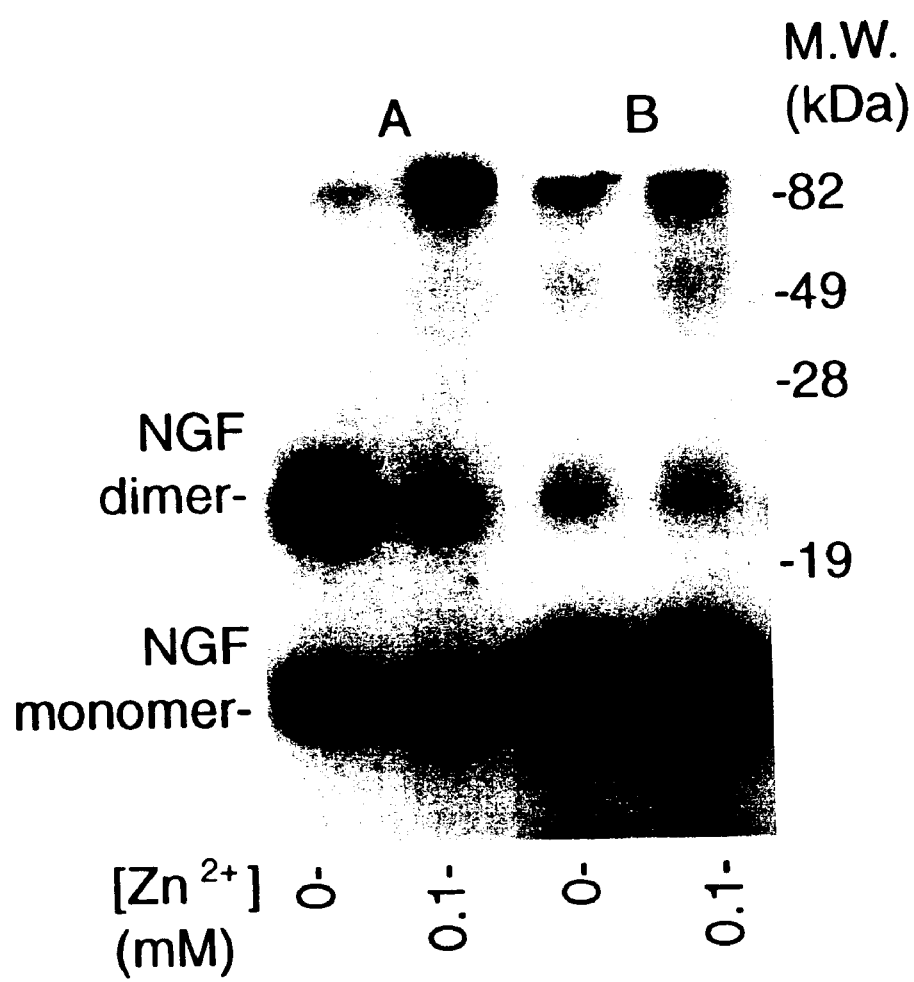

As changes in NGF conformation in the presence of $Zn^{2+}$ were predicted to be mediated by His residues, the effects of $Zn^{2+}$ on NGF with chemically altered His residues were investigated (FIG. 14d). When His residues were modified with diethyl-pyrocarbonate (DEPC), several changes in NGF function were observed including a loss in receptor binding activity as previously described (Woo, S. B. & Neet, K. E. Characterization of histidine residues essential for receptor binding and activity of nerve growth actor. *J. Biol. Chem.* 271, 24433–24441 (1996)) and a reduction in protomer crosslinking efficiency. The loss in crosslinking efficiency is consistent with structural alterations in the NGF amino terminus, the conformation of which is determined in part by His residues (Shamovsky, I. L., Ross, G. M., Riopelle, R. J. & Weaver, D. F. Theoretical studies on the bioactive conformation of nerve growth factor using VBMC-A novel variable basis Monte Carlo simulated annealing algorithm for peptides. *J. Am. Chem. Soc.* 118, 9743–9749 (1996)). While the efficiency of protomer crosslinking was reduced upon DEPC modification, significant crosslinking was maintained. The crosslinking of NGF promoters after His modification was not affected by $Zn^{2+}$, consistent with the requirement of intact His residues for a $Z^{2+}$ effect The ability of $Z^{2+}$ to alter the conformation of NGF prompted us to examine the effect of $Zn^{2+}$ on NGF mediated activities, since the predicted conformational changes involve NGF binding domains essential for both $p75^{NTR}$ (residues 28–36; Van der Zee, C. E. E. M., Ross, G. M., Riopelle, R. J. & Hagg, T. Survival of cholinergic forebrain neurons in developing $p75^{NGFR}$ deficient mice. *Science* 274, 1729–1732 (1996) and Bradshaw, R. A. et al. Nerve growth factor. Structure/function relationships. *Protein Science* 3, 1901–1913 (1994)) and TrkA (amino and carboxyl termini; Shamovsky, I. L., Ross, G. M., Riopelle, R. J. & Weaver, D. F. Theoretical studies on the bioactive conformation of nerve growth factor using VBMC-A novel variable basis Monte Carlo simulated annealing algorithm for peptides. *J. Am. Chem. Soc.* 118, 9743–9749 (1996) and references therein) receptor recognition. The cell line PC12 (Greene, L. A & Tischler, A. S. Establishment of a noradrenergic clonal cell line of rat pheochromocytoma cells which respond to nerve growth factor. *Proc. Natl. Acad. Sci. USA* 73, 2424–2432 (1976)) was used for binding studies as these cells express both NGF receptor types, with $p75^{NTR}$ representing approximately 90% and TrkA approximately 10% of the NGF binding sites. The effects of $Zn^{2+}$ on total specific binding ($p75^{NTR}$+TrkA) as well as TrkA binding (determined by blocking binding to $p75^{NTR}$ with BDNF) are shown in Table 1 below.

TABLE 1

Zinc inhibits $^{125}$I-NGF binding to p75$^{NTR}$ and TrkA receptors

| [Zn$^{2+}$] (μM) | Control Ions (μM) | Receptors | % Control ± SEM (n) |
|---|---|---|---|
| \multicolumn{4}{l}{Inhibition of steady-state specific binding of $^{125}$I-NGF (0.5 nM) to p75$^{NTR}$ and TrkA} | | | |
| 0 | | p75$^{NTR}$, TrkA | 100 (9) |
| 10 | | p75$^{NTR}$, TrkA | 88 ± 13 (9) |
| 30 | | p75$^{NTR}$, TrkA | 82 ± 10 (7) |
| 50 | | p75$^{NTR}$, TrkA | 44 ± 13 (9)* |
| 100 | | p75$^{NTR}$, TrkA | 19 ± 9 (9)* |
| 0 | 100 Ca$^{2+}$ | p75$^{NTR}$, TrkA | 91 ± 7 (7) |
| 0 | 100 Mg$^{2+}$ | p75$^{NTR}$, TrkA | 88 ± 13 (7) |
| 100 | 100 CaEDTA | p75$^{NTR}$, TrkA | 78 ± 19 (7) |
| \multicolumn{4}{l}{Inhibition of steady-state specific binding of $^{125}$I-NGF (0.5 nM) to TrkA[a]} | | | |
| 0 | | TrkA | 100 (7) |
| 100 | | TrkA | 19 ± 15 (7)* |
| 100 | 100 CaEDTA | TrkA | 87 ± 13 (3) |

*significantly less than control; $p \leq 0.05$
[a] determined in the presence of 40 nM BDNF Zn$^{2+}$ significantly inhibited (>50%) $^{125}$I-NGF binding to both p75$^{NTR}$ and TrkA at concentrations of 50 μM and effectively blocked binding at 100 μM. Concentrations above 100 μM could not be tested as Zn$^{2+}$ altered nonspecific binding at higher concentrations. The effects observed with Zn$^{2+}$ were specific, as neither Ca$^{2+}$ nor Mg$^{2+}$ displayed significant inhibition of $^{125}$I-NGF binding. Inhibitory effects of Zn$^{2+}$ could also be prevented by including CaEDTA in the incubation buffer to chelate the Zn$^{2+}$ cation (Koh, J.-Y. et al. The role of zinc in selective neuronal death after global cerebral ischemia. Science 272, 1013–1016 (1996)).

Figure 15A:
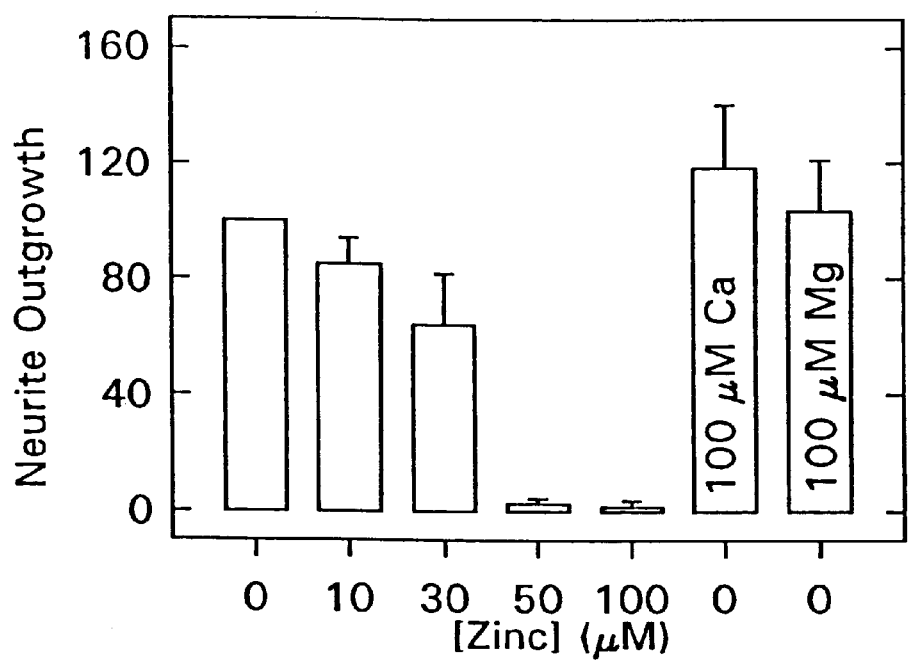
FIGS. 15A–D illustrates the effects of $Zn^{2+}$ on neurite growth, survival and toxicity. (a) The ability of $Zn^{2+}$ to inhibit NGF-induced neurite outgrowth in DRG neurons was evaluated in the presence of varying concentrations of $Zn^{2+}$. $Zn^{2+}$ concentrations of 50 and 100 $\mu M$ inhibited neurite extension, whereas $Ca^{2+}$ and $Mg^{2+}$ had no effect at 100$\mu M$. (b) $Zn^{2+}$ was effective in preventing NGF-mediated survival of PC12 cells in serum-free conditions, while $Ca^{2+}$ and $Mg^{2+}$ had no effect The effects of $Zn^{2+}$ on NGF mediated survival were reversed using the selective chelating agent CaEDTA (also at 100 $\mu M$). (C) While $Zn^{2+}$ prevents the ability of NGF to maintain survival of PC12 cells in serum-free conditions, $Zn^{2+}$ (or $Ca^{2+}$, $Mg^{2+}$) was not toxic to PC12 cells in the presence of serum. (d) Effects of $Zn^{2+}$ on TrkA phosphorylation The ability of $Zn^{2+}$ to prevent NGF-induced phosphorylation of the TrkA receptor was evaluated by anti-phosphotyrosine Western blotting of the TrkA receptor isolated by immunoprecipitation. $Zn^{2+}$ had no effect on basal TrkA phosphorylation (–NGF control) but prevented phosphorylation observed in the presence of 40 $\mu M$ NGF (+NGF control). Neither $Ca^{2+}$, $Mg^{2+}$ nor CaEDTA had a significant effect on NGF dependent phosphorylation, but the inhibition observed in the presence of $Zn^{2+}$ was reversed by CaEDTA (all at 100 $\mu M$).

Effects of Zn$^{2+}$ on NGF mediated neurite outgrowth of dorsal root ganglia (DRG) neurons were also quantitated. At concentrations of Zn$^{2+}$ which showed inhibition in $^{125}$I-NGF binding, a significant inhibition of neurite extension was observed (FIG. 15a). The ions Ca$^{2+}$ and Mg$^{2+}$ had no effect on neurite outgrowth at this concentration.

Figure 15B:
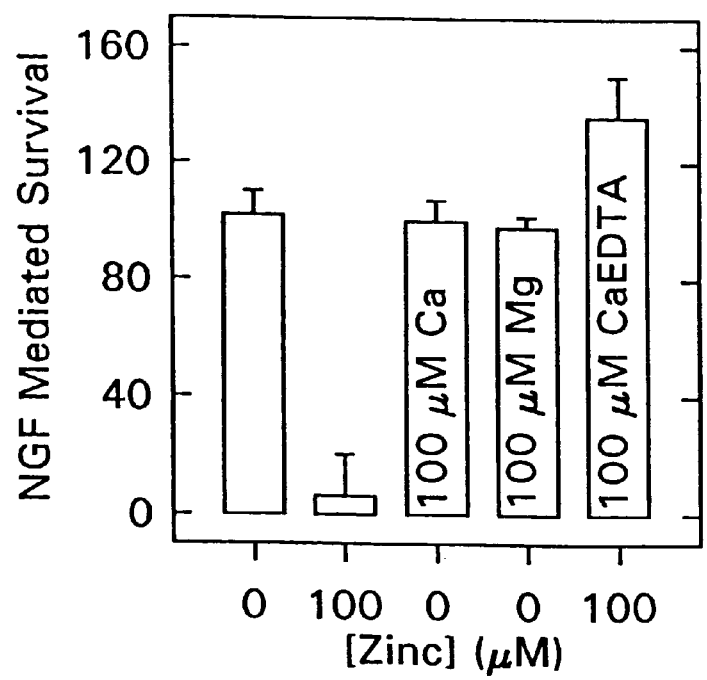
Figure 15C:
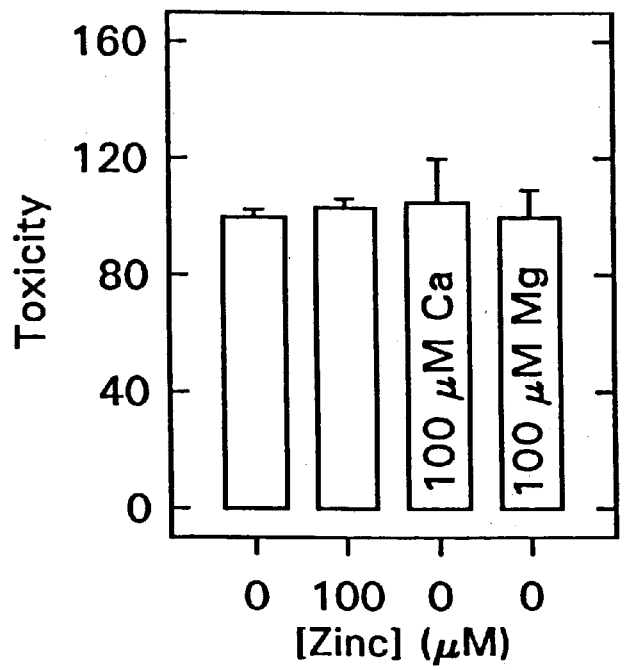

NGF rescues PC12 cells from death induced by serum deprivation. At 100 μM Zn$^{2+}$, the ability of NGF to promote PC12 cell survival in the absence of serum was reduced signifcantly, while no effect of Ca$^{2+}$, Mg$^{2+}$ or CaEDTA with Zn$^{2+}$ could be detected (FIG. 15b). To ensure that the inhibition of NGF mediated survival of PC12 cells in the absence of serum was not due to a toxic effect of Z$^{2+}$, the effect of this ion on cells in the presence of serum was monitored. A concentrations of Zn$^{2+}$ up to 100 μM, no loss in cell viability was observed at times comparable to those used in assessing NGF-dependent survival (FIG. 15c).

Figure 15D:
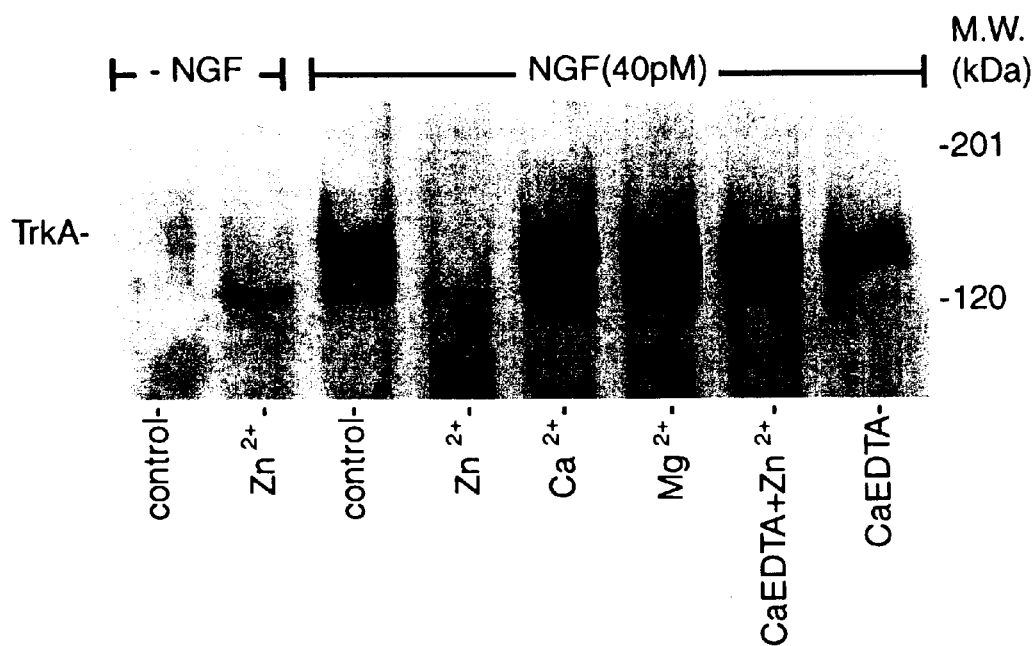

NGF induces a rapid increase in phosphorylation of tyrosine residues within the TrkA receptor as part of a signal transduction cascade (Kaplan, D. R, Matin-Zanca, D. & Parada, L. F. Tyrosine phosphorylation and tyrosine kinase activity of the trk proto-oncogene product induced by NGF. Nature 360, 158–160 (1991) and Kaplan, D. R., Hempstead, B. L., Martin-Zanca, D., Chao, M. V. & Parada, L. F. The trk proto-oncogene product: a signal transducing receptor for nerve growth factor. Science 252, 554–558 (1991)). Using conditions where a rapid increase in TrkA phosphorylation is induced by NGF, Zn$^{2+}$ (100 μM) prevented phosphorylation of this receptor. A similar inhibition of TrkA phosphorylation was not detected with Ca$^{2+}$ or Mg$^{2+}$ and a reduction in Zn$^{2+}$ mediated inhibition was observed in the presence of CaEDTA (FIG. 15d).

The ability of Zn$^{2+}$ to interact with other neurotrophins, while not previously suggested, would be expected. Other neurotrophins share features of NGF predicted to mediate Zn$^{2+}$ interactions, including the presence of residues His, Asp and Glu in their amino termini and a conserved acidic residue Asp-105 capable of ligationing Zn$^{2+}$. We have examined the ability of Zn$^{2+}$ to modulate BDNF and NT-3 functions in representive assay systems. An alteration of BDNF and NT-3 conformation and function in the presence of Zn$^{2+}$ (as measured by neurotrophin protomer crosslinking, p75$^{NTR}$ binding and neurotrophin-dependent neurite outgrowth) was observed, see Table 2 below.

TABLE 2

Zn$^{2+}$ Inhibits BDNF and NT-3 Function

| Neurotrophin | [Zn$^{2+}$] (μM) | |
|---|---|---|
| \multicolumn{3}{l}{% Maximum p75$^{NTR}$ binding} | | |
| \multicolumn{3}{l}{% Maximum binding (n = 3)} | | |
| $^{125}$I-BDNF | 0 | 100 |
| | 100 | 10.0 ± 4.5 |
| $^{125}$I-NT-3 | 0 | 100 |
| | 100 | 13.3 ± 9.5 |
| \multicolumn{3}{l}{Conformation by BS$^3$ crosslinking} | | |
| \multicolumn{3}{l}{% Maximum crosslinked dimer (n = 3)} | | |
| $^{125}$I-BDNF | 0 | 100 |
| | 100 | 75.9 ± 16.1 |
| $^{125}$I-NT-3 | 0 | 100 |
| | 100 | 56.5 ± 10.7 |
| \multicolumn{3}{l}{Neurite Outgrowth} | | |
| \multicolumn{3}{l}{% Maximum process bearing neurons (n = 8)} | | |
| BDNF (8.0 nM) | 0 | 100 |
| | 30 | 30.0 ± 13.3 |
| | 50 | 1.4 ± 1.4 |
| NT-3 (4.0 nM) | 0 | 100 |
| | 30 | 79.9 ± 13.8 |
| | 50 | 18.4 ± 9.6 |

Discussion

A detailed molecular dynamics simulation of the conformation of NGF bound to Zn$^{2+}$ revealed a structure significantly altered from NGF in the absence of Zn$^{2+}$. The major stabilizing factor of the oomph is pentagonal Zn$^{2+}$ chelation by four NGF residues (FIGS. 12b and 13). Attractive electrostatic interaction of Ser-1$_{[1]}$ with Glu-35$_{[2]}$ compensates equivalent energy loss associated with the separation of amino and carboxyl termini (FIG. 12a). The geometry of the Zn$^{2+}$ coordination state agrees well with published observations (Zhang, D. et al. Atrolysin C. Protein Data Bank (Brookhaven National Laboratory, Upton, N.Y.), accession code 1ATL; Sarkar, B. Peptide models for the metal-binding sites of proteins and enzymes. J. Indian Chem. Soc. 59, 1403–1411 (1982); Vedani, A, Huhta, D. W. & Jacober, S. P. Metal coordination, H-bond network formation, and protein-solvent interactions in native and complexed human carbonic anhydrase I: A molecular mechanics study. J. Am. Chem. Soc. 111, 4075–4081 (1989); Argos, P., Garavito, R. M., Eventoff, W. & Rossmann, M. G. Similarities in active center geometries of zinc-containing enzymes, proteases and dehydrogenases. J. Mol. Biol. 126, 141–158 (1978)). Moreover, predicted structural features of the Zn$^{2+}$ binding site in NGF follow general rules observed in other Zn$^{2+}$-bound proteins. Spacing between residues His-4 and His-8 (three residues) is consistent with characteristic "short spacers" between ligationing residues in Zn$^{2+}$-bound proteins (Sarkar, B. Peptide models for the metal-binding sites of proteins and enzymes. J. Indian Chem. Soc. 59, 1403–1411 (1982); Kochoyan, M., Keutmann, H. T. & Weiss, M. A.

Alternating zinc fingers in the human male-associated protein ZFY: $HX_3H$ and $HX_4H$ motifs encode a local structural switch. *Biochemistry* 30, 9396–9402 (1991); Green, L. M. & Berg, J. M. A retroviral Cys-Xaa$_2$-Cys-Xaa$_4$-His-Xaa$_4$-Cys peptide binds metal ions: Spectroscopic studies and a proposed three dimensional structure. *Proc. Natl. Acad. Sci. USA* 86, 4047–4051 (1989); Bertini, I., Luchinat C. & Scozzafava, A. Carbonic anhydrase: An insight into the zinc binding site and into the active cavity through metal substitution. *In: Structure and Bonding.* Springer-Verlag: Berlin-Heidelberg, v.48, 1982, pp 45–92; Tainer, J. A, Getzoff, E. D., Beem, K. M., Richardson, J. S. & Richardson, D. C. Determination and analysis of the 2 Å structure of copper, zinc superoxide dismutase. *J. Mol. Biol.* 160, 181–217 (1982); Vallee, B. L. & Auld, D. S. Active-site zinc ligands and activated $H_2O$ of zinc enzymes. *Proc. Natl. Acad. Sci. USA* 87, 220–224 (1990)). The split of the $Zn^{2+}$ binding site in NGF into two domains, each containing two coordinating residues, is typical for $Zn^{2+}$ bound proteins (Sheridan, R. P. & Allen, L. C. The active site electrostatic potential of human carbonic anhydrase. *J. Am. Chem. Soc.* 103, 1544–1550 (1981)) and $Zn^{2+}$-mediated protein complexes (Cunningham, B. C., Mulkerrin, M. G. & Wells, J. A. Dimerization of human growth hormone by zinc. *Science* 253, 545–548 (1991); Somers, W., Ulsch, M., De Vos, A. M. & Kossiakoff, A. A. The X-ray structure of a growth hormone-prolactin receptor complex *Nature* 372, 478–481 (1994); Matthews, D. J. & Wells, J. A. Engineering an interfacial zinc site to increase hormone-receptor affinity. *Chemistry & Biology* 1, 25–30 (1994)).

Experiments demonstrating an altered ability of $BS^3$ to covalently crosslink NGF monomers in the presence of $Zn^{2+}$, suggested changes in NGF conformation induced by this ion. The observation that NGF dimer crosslinking was inhibited while the crosslinking to other proteins within the buffer system was promoted eliminates the possibility that $Zn^{2+}$ prevents dimer crosslinking by a non-specific (e.g. crosslinker scavenging) mechanism and provides H evidence for altered NGF conformation. An alteration in the CD spectra in the presence of $Zn^{2+}$ also confirms changes in NGF conformation. Non-reducing gel electrophoresis studies(Woo, S. B. & Neet, K. E. Characterization of histidine residues essential for receptor binding and activity of nerve growth factor. *J. Biol. Chem.* 271, 24433–24441 (1996)) which demonstrate no change in the relative amount of NGF existing as a dimer in the presence of $Zn^{2+}$ indicate that such conformational change occurs within an intact dimer structure.

While chemical crosslinking of NGF monomers could occur at multiple sites, one of the most likely events would be the bridging of juxdapositioned primary amines of Lys115$_{[2]}$ and Ser-1$_{[1]}$ (FIG. 12). In accord with observations, the predicted $Zn^{2+}$-induced conformational transition would place the side-chain of Lys-115 at a much greater distance from the amino terminus, making this crosslinking event highly unlikely. Although other functional groups of NGF could provide the required inter-monomer covalent modification (e.g. Lys-74$_{[1]}$ and Lys-74$_{[2]}$), they are located in rigid domains of NGF, unlikely to be affected by $Zn^{2+}$ binding.

Five NGF residues potentially participate in the formation of the $Zn^{2+}$ binding site: His-4$_{[1]}$, is His-8$_{[1]}$, His-84$_{[2]}$, Asp-105$_{[2]}$ and Glu-35$_{[2]}$. These residues are conserved in NGF from all species except snake, suggesting a predisposition of NGF for $Zn^{2+}$-mediated inactivation. The experimental results obtained are all consistent with the model of a $Z^{2+}$-induced conformational transition of NGF. Although the possibility of $Zn^{2+}$-mediated oligomerization cannot be excluded, such a mechanism is unlikely because of the low concentrations of neurotrophin (sub-nanomolar) used in this study.

The requirement of amino and carboxyl terminal residues in the activation of TrkA by NGF has been well documented (Bradshaw, R. A. et al. Nerve growth factor: Structure/function relationships. *Protein Science* 3, 1901–1913(1994), Ibáñez, C. F. Neurotrophic factors: From structure/function studies to designing elective therapeutics. *Trends Biotech.* 13, 217–227 (1995), Shih, A., Laramee, G. R., Schmeizer, C. H., Burton, L. E. & Winslow, J. W. Mutagenesis identifies amino-terminal residues of nerve growth factor necessary for trk receptor binding and biological activity. *J. Biol. Chem.* 269, 27679–27686 (1994), and Shamovsky, I. L., Ross, G. M., Riopelle, R. J. & Weaver, D. F. Theoretical studies on the bioactive conformation of nerve growth factor using VBMC-A novel variable basis Monte Carlo simulated annealing algorithm for peptides. *J. Am. Chem. Soc.* 118, 9743–9749 (1996)). The geometric features of the NGF amino and carboxyl termini which are stereochemically compatible with a TrkA binding site (e.g. the exposed β-strand motif) are lost within be $Zn^{2+}$ bound complex. Further, since residue Glu-35 of NGF directly participates in the interaction with p75$^{NTR}$ (Ibáñez, C. F., et al. Disruption of the low affinity receptor-binding site in NGF allows neuronal survival and differentiation by binding to the trk gene product. *Cell* 69, 329–341 (1992)), the steric hindrance caused by the amino terminus in this region is consistent with a loss of NGF interaction with p75$^{NTR}$.

Without implying that effects of $Zn^{2+}$ are restricted to influences on NGF only, the observation that $Zn^{2+}$ inhibits binding of $^{125}$I-NGF to both the p75$^{NTR}$ and TrkA receptor suggests that this ion may play an important role in a the modulation of NGF signalling. Furthermore, at concentrations of $Zn^{2+}$ expected under certain pathological conditions, the binding of $^{125}$I-NGF to TrkA and p75$^{NTR}$ is effectively abolished, suggesting the capacity for $Zn^{2+}$ to negate the actions of increased levels of NGF on responsive cell populations following insult.

Consistent with the ability of $Zn^{2+}$ to inhibit binding of NGF to its receptor sites is the demonstration that $Zn^{2+}$ inhibited the best in culture (Dostaler, S. M. et al. Characterization of a distinctive motif of the low molecular weight neurotrophin receptor that modulates NGF-mediated neurite growth. *Eur. J. Neurosci.* 8, 870–879 (1996)). Accompanying characterized in vitro NGF effects on biological outcome, namely NGF-induced neurite outgrowth of DRG neurons and NGF-dependent survival of PC12 cells the loss in NGF binding and biological function is the inhibition of TrkA phosphorylation induced by NGF, a key initial event in the signal transduction pathway mediated by this receptor. The specificity of these effects are highlighted by the inability of the ions $Ca^{2+}$ and $Mg^{2+}$ to induce similar results and the ability of CaEDTA to prevent the $Zn^{2+}$ induced inhibition of NGF function. Importantly, the selectivity of $Zn^{2+}$ effects on the actions of NGF were illustrated by the lack of a toxic effect of $Zn^{2+}$ on these cells under conditions where NGF is not required for survival.

Since BDNF and NT3 share Asp-105 with NGF, and taking into account that their amino termini also contain residues able to chelate $Zn^{2+}$ (His, Asp, and Glu), similar $Zn^{2+}$-induced alterations are also expected to take place in these neurotrophins. BDNF and NT3 were also tested in assay systems sensitive to neurotrophin conformation and both proteins displayed similar changes in the presence of $Zn^{2+}$ with respect to conformation. binding to p75$^{NTR}$ and neurite outgrowth of cultured DRG neurons.

To the extent that $Zn^{2+}$ and neurotrophins have been implicated in the pathogenesis of neurological disease states (e.g. stroke, Alzheimer's disease, epilepsy), the present studies provide one mechanism to suggest that a $Zn^{2+}$-neurotrophin in interaction may be deleterious. Alternatively, under specific conditions, $Zn^{2+}$ inactivation of neurotrophins may mitigate neural cell death via a p75$^{NTR}$ mediated signal. The recognition that aberrant $Zn^{2+}$ regulation may induce neuronal damage by a specific interaction with a neurotrophin will provide additional strategies for therapeutic intervention. Further, in cases where activity appears to have detrimental effects (pain, inflammation (Lewin, G. R. & Mendell, L. M. Nerve growth factor and nociception. *Trends Neurosci.* 16, 353–359 (1993), Woolf, C. J. & Doubell, T. A. The patophysiology of chronic pain—increased sensitivity to low threshold Aβ-fiber inputs. *Curr. Opin. Neurobiol.* 4, 525–534 (1994), and McMahon, S. B., Bennett, D. L. H., Priestley, J. V. & Shelton, D. L. The biological effects of endogenous nerve growth factor on adult sensory neurons revealed by a trkA-IgG fusion molecule. *Nature Med.* 1, 774–780 (1994)), cell death (Frade, J. M., Rodriguez-Tébar, A. & Barde, Y.-A. Induction of cell death by endogenous nerve growth factor through its p75 receptor. *Nature* 383, 166–168 (1996), Casaccia-Bonnefil, P., Carter, B. D., Dobrowsky, R. T. & Chao, M. V. Death of oligodendrocytes mediated by the interaction of nerve growth factor with its receptor p75. *Nature* 383, 716–719 (1996)). Inhibition of neurotrophin activity using similar approaches are contemplated to have therapeutic utility.

2) Other Transition Metals

To explore the ability of other transition metals to influence the biological activities of NGF, a series of cations known to mimic in certain respects the binding of zinc to proteins were tested. Of the metals tested, $Cd^{2+}$, $Co^{2+}$ and $Hg^{2+}$ (indicated in bold in Table 3 below) were toxic to PC12 cells in serum4ee conditions. For this reason these ions were not tested in NGF- dependant growth phenomena. The remaining metals which did not possess significant toxic profiles were tested in NGF-dependant cell survival assay (PC12 in the presence of serum). Of these, $Au^{3+}$, $Cu^{2+}$, $Ni^{2+}$, $Pt^{2+}$ in addition to $Zn^{2+}$ had an ability to antagonize the NGF-dependant survival of these cells in either high (1 nM) or low (50 pM) NGF environment (indicated by italics). Several of the metals had the ability to prevent binding of $^{125}$I-NGF to PC12 cells ($Cu^{2+}$, $Pd^{2+}$), however some ions which were effective in the biological assay system ($Au^{3+}$, $Ni^{2+}$), did not show appreciable inhibition of $^{125}$I-NGF binding to PC12 cells. Further, when these metals were tested in the NGF protomer crosslinking assay system, $Ni^{2+}$ did not appear to have an effect on the conformation of the NGF protein, while appearing to be an effective antagonist in the survival assay. As these studies appeared to indicate potentially complex results upon metal ions binding to NGF, a receptor crosslinking system where specific receptor types could be identified was utilized. Using this assay system, $Au^{3+}$ and $Ni^{2+}$ were seen to be selective for blocking the binding of NGF to TrkA but did not prevent the binding of NGF to p75$^{NTR}$. The ions $Cu^{2+}$, $Pd^{2+}$, $Pt^{2+}$ and $Zn^{2+}$ blocked binding to both receptors, while $Fe^{2+}$, $Fe^{3+}$ and $Mn^{2+}$ did not have a significant effect on the crosslinking of $^{125}$I-NGF to either receptor type.

The effects of binding transition metal ions to NGF and resultant changes in conformation, receptor binding, and subsequent biological effects of this protein are complex Ions which altered biological activity of NGF without affecting p75$^{NTR}$ binding (eg. $Au^{3+}$, $Ni^{2+}$) were identified, as was an ion which did not appear to after protomer conformation by examining protomer crosslinking yet did block binding to TrkA and NGF-dependant biological outcomes ($Ni^{2+}$). The reasons for this complex range of activities in the various assay systems likely results from differences in valence, co-ordination geometry and number, atomic size and other significant differences between the transition elements.

These studies have shown directly that certain metal species have a selective inhibitory effect of one of the neurotrophin receptors. Such selective receptor inhibition is observed for both $Ni^{2+}$ and $Au^{3+}$ acting preferentially at the TrkA receptor This observation would likely be mimicked by other metal ions which share atomic features with these ions. Such an observation also enables the development of unique strategies to develop other selective neurotrophin antagonism, either with metal ions themselves or alternately by designing molecules which will induce the predicted metal ion-induced alterations in NGF conformation.

TABLE 3

Effects of transition metals an PC12 cell viability, NGF-mediated cell survival, NGF-receptor interactions and NGF conformation.

| Transition Element [100 μM] | Toxicity (% control) | Survival @ 50 pM NGF (% control) | Survival @ 1 nM NGF (% control) | Total Binding to PC12 cells (% control) | NGF Protomer Conformation (active/inactive) | Receptor Selectivity (p75$^{NTR}$/TrkA) |
|---|---|---|---|---|---|---|
| $Au^{3+}$ | 102 ± 13 | 0.1 ± 9 | −8 ± 5 | 107 ± 4 | active | TrkA only |
| $Cd^{2+}$ | 63 ± 10 | | | | | |
| $Co^{2+}$ | 52 ± 14 | | | | | |
| $Cu^{2+}$ | 74 ± 10 | −2 ± 19 | −6 ± 8 | −16 ± 7 | active | both |
| $Fe^{2+}$ | 87 ± 8 | 77 ± 24 | 74 ± 20 | 59 ± 4 | inactive | — |
| $Fe^{3+}$ | 91 ± 13 | 75 ± 17 | 75 ± 18 | 48 ± 6 | inactive | — |
| $Hg^{2+}$ | 3 ± 0.8 | | | | | |
| $Mn^{2+}$ | 82 ± 4 | 91 ± 5 | 59 ± 24 | 95 ± 24 | inactive | — |
| $Ni^{2+}$ | 100 ± 19 | 15 ± 13 | 23 ± 10 | 69 ± 18 | inactive | TrkA only |
| $Pd^{2+}$ | 75 ± 6 | 82 ± 9 | 125 ± 48 | −5 ± 1 | active | both |
| $Pt^{2+}$ | 93 ± 6 | 74 ± 21 | 92 ± 35 | 68 ± 11 | active | both |
| $Zn^{2+}$ | 97 ± 11 | 67 ± 19 | 84 ± 39 | 21 ± 5 | active | both |

NGF is a homodimeric protein having a structure wherein the N-terminus of the first protomer is associated with the C-terminus of the second protomer, and the N-terminus of the second protomer is associated with the C-terminus of the first protomer. The inventors have shown that the TrkA receptor tyrosine kinase interacts with the associated N- and C-termini. The p75$^{NTR}$ receptor interacts with a different region of NGF.

Figure 16:
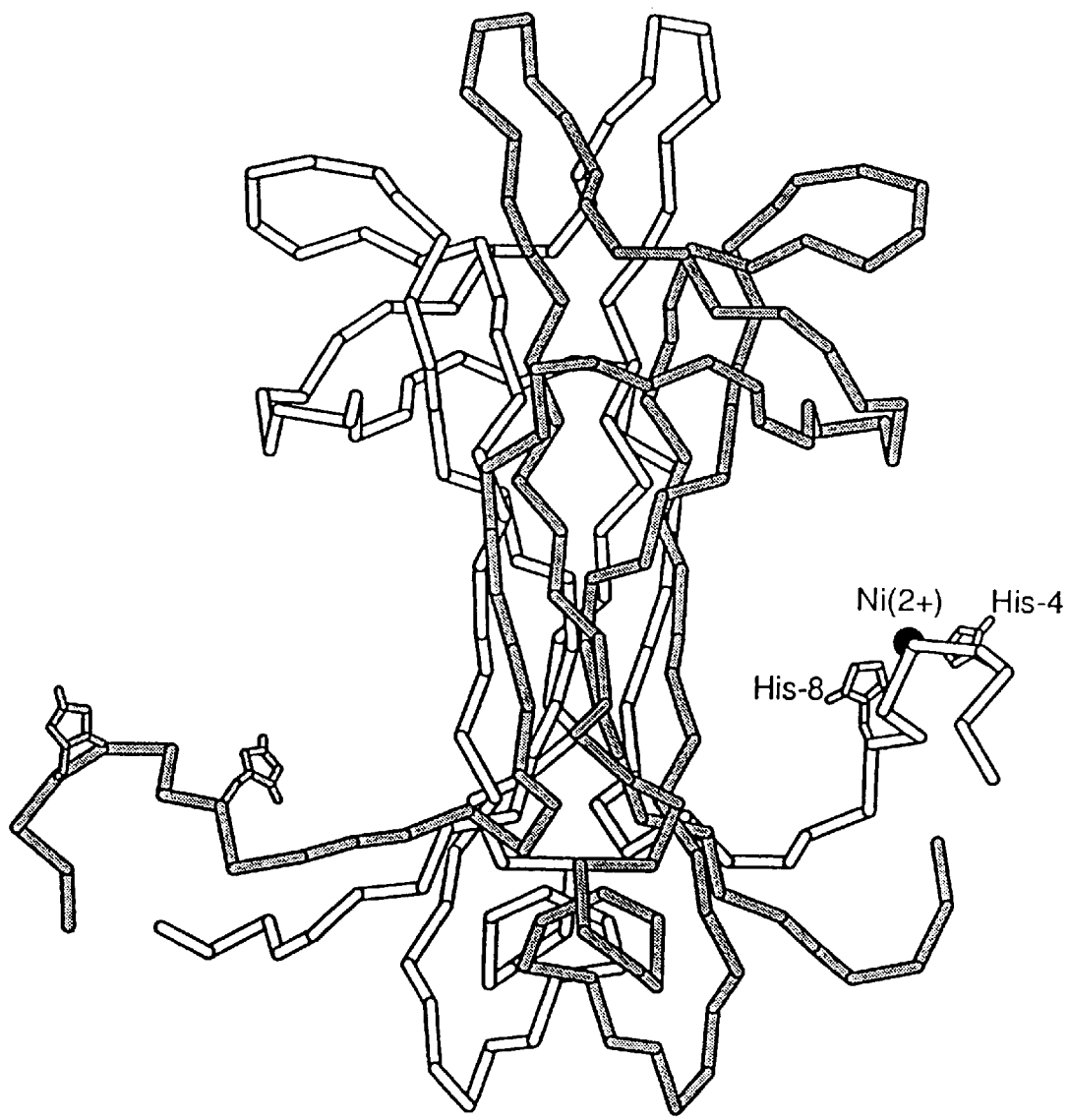
FIG. 16 shows calculated minimal energy conformation of $Ni^{2+}$ bound to NGF. The location of $Ni^{2+}$ binding to the N-terminus of NGF is shown for one protomer only. A similar $Ni^{2+}$ complex is also expected for the second N-terminus In the structure depicted, $Ni^{2+}$ coordinates with two His residues in the N-terminus only and does not coordinate to either His 84 or Asp 105 as predicted for $Zn^{2+}$. Within the $Ni^{2+}$ bound complex, the N-terminal $\alpha$-amino group is within $BS^3$ spanning distance of Lys 115, consistent with the ability of $BS^3$ to crosslink NGF prtomers in the presence of $Ni^{2+}$. Further, the $Ni^{2+}$-bound N-terminus does not sterically interact with Loop 1 (residues 28–36), allowing the $Ni^{2+}$-NGF complex to bind $p75^{NTR}$. In contrast, the conformation of the domain comprising the N-terminus of the first protomer and the C-terminus of the second protomer, known to mediate TrkA binding, is altered considerably. This result is consistent with a loss of NGF binding to TrkA in the presence of $Ni^{2+}$.
Figure 17:
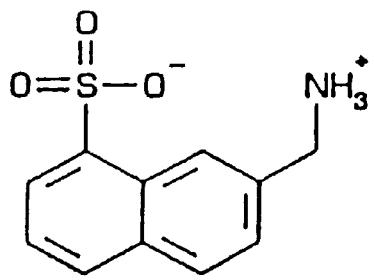
FIG. 17 shows the structures of two prophetic molecules expected to bind to NGF at two of the four residues predicted to bind $Zn^{2+}$. The two molecules, each with an anionic group ($SO_3^-$) and a cationic group ($NH_3^+$), are spaced appropriately to allow bridging of His 84 and Asp 105. Binding of the indicated molecules to NGF would be expected to reduce the ability of $Zn^{2+}$ to bind to NGF by competing for same binding site, and thus would alter the effects of $Zn^{2+}$ on NGF.
Figure 17:
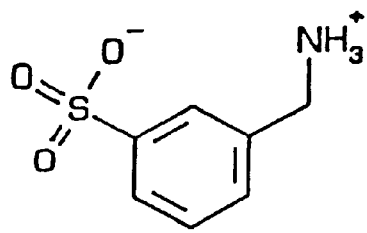
Figure 18:
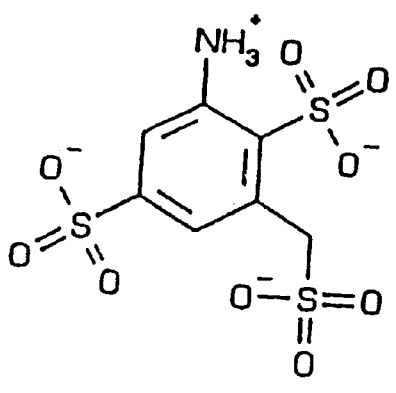
FIG. 18 shows the structures of two prophetic molecules expected to bind to NGF at the four amino acid residues (Asp 105, His 84, His 4, His 8) predicted to participate in binding of several metal ions to NGF. These two molecules have charge and steric features which would mimic the interaction of $Zn^{2+}$ and similar metals with NGF.
Figure 18:
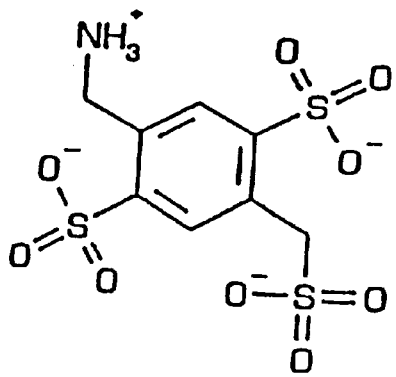
Figure 19:
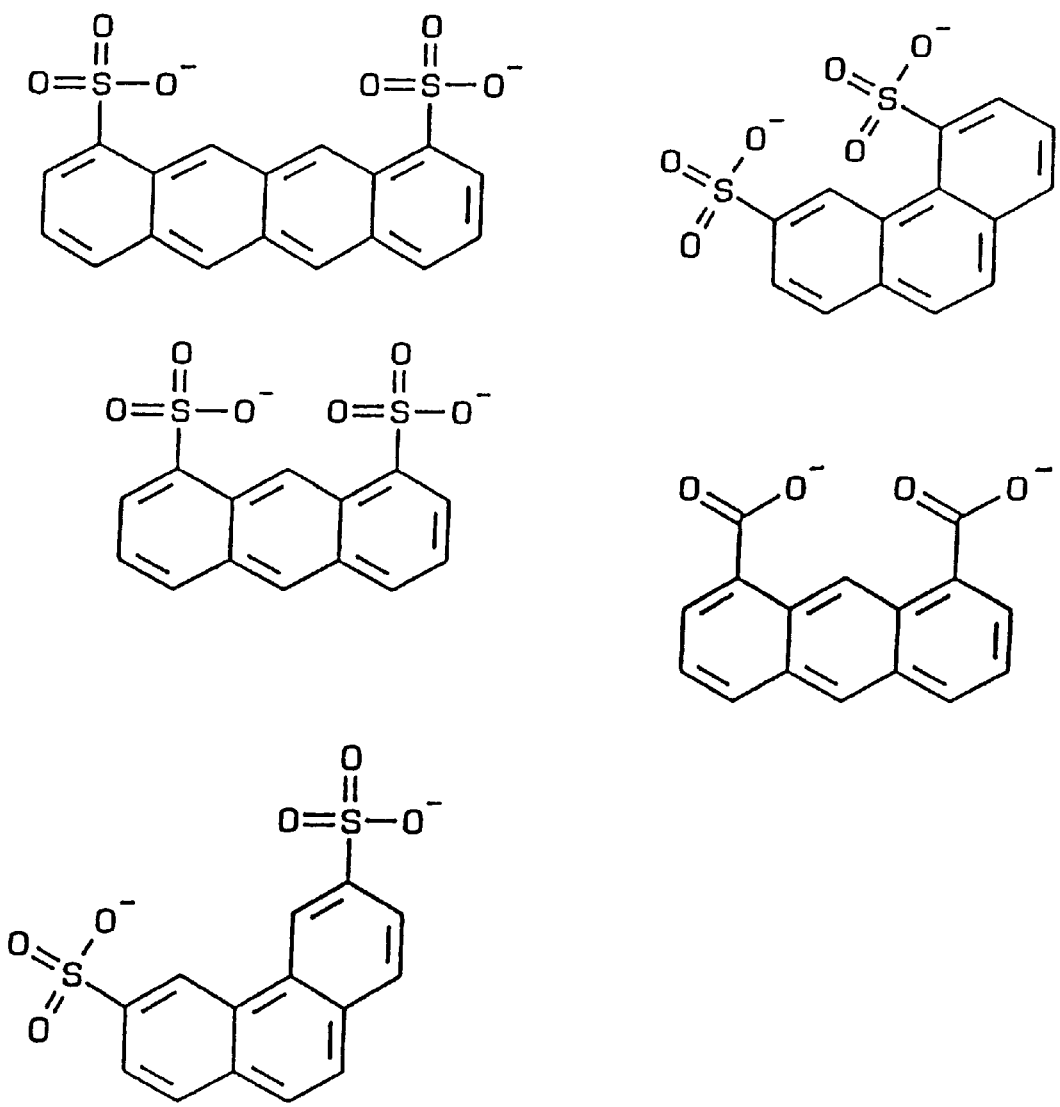
FIG. 19 shows the structures of five prophetic molecules expected to bind to NGF at the two His residues (His 4 and His 8) in the N-terminal region. The spacing of anionic groups ($SO_3^-$or $O_2^-$) in these molecules is predicted to allow binding to the two His residues and alter conformation of the N-terminus in a manner similar to $Ni^{2+}$ and related metals. Mimicking $Ni^{2+}$, such factors should be selective for TrkA, i.e., not alter binding to $p75^{NTR}$.

According to the present model, when divalent zinc ($Zn^{2+}$) associates with the N-terminus of a protomer, the N-terminus "bends away", to another region of the protein, dissociating from the C-terminus of the other protomer, and forming a coordination complex wherein the zinc is coordinated by four amino acid residues, two histidine (His) residues near the N-terminus and a histidine and an aspartic acid (Asp) located elsewhere in the protein On the other hand, divalent nickel ($Ni^{2+}$) only requires coordination at two points. According to the model, nickel binds to the N-terminal region of a protomer at two points (the same two histidine mentioned above), making a "kink", and thereby dissociating from the C-terminus of the other protomer FIG. 16 shows calculated minimal energy conformation of $Ni^{2+}$ bound to NGF. The location of $Ni^{2+}$ binding to the N-terminus of NGF is shown for one protomer only. A similar $Ni^{2+}$ complex is also expected for the second N-terminus. In the structure depicted, $Ni^{2+}$ coordinates with two His residues in the N-terminus only and does not coordinate to either His 84 or Asp 105 as predicted for $Zn^{2+}$. Within the $Ni^{2+}$ bound complex, the N-terminal α-amino group is within $BS^3$ spanning distance of Lys 115, consistent with the ability of $BS^3$ to crosslink NGF promoters in the presence of $Ni^{2+}$. Further, the $Ni^{2+}$-bound N-terminus does not sterically interact with Loop 1 (residues 28–36), allowing the $Ni^{2+}$-NGF complex to bind $p75^{NTR}$. In contrast, the conformation of the domain comprising the N-terminus of the first protomer and the C-terminus of the second protomer, known to mediate TrkA binding, is altered considerably This result is consistent with a loss of NGF binding to TrkA in the presence of $Ni^{2+}$.

For both zinc and nickel, disruption of the interaction of the N-terminus of the first protomer with the C-terminus of the second protomer inhibits or eliminates interaction of NGF with TrkA. However, in addition, the inventors have discovered that zinc disrupts the Interaction of NGF with p75, but nickel does not. According to the model, this is because the two-way coordination complex ("kink") of nickel does rot affect the p75 binding domain, whereas the four-way coordination complex with zinc is produces more dramatic conformational change and disrupts the p75 binding site. Specifically, the inventors believe that the amino group of the N-terminal amino acid interacts with a glutamate in loop 1 of the p75 binding domain, causing a salt bridge to form. Thus, not only is the Trk binding site disrupted, but the p75 binding site is disrupted as well.

The interactions on the molecular level that just described are consistent with known facts with respect to stroke. It is known that zinc is released in large quantities in stroke and it is known that a lot of cellular damage is caused by stroke. According to the inventors' model, the release of zinc during stroke could be disrupting the interaction of the promoters of neurotrophins, thereby interfering with neurotrophin-receptor binding, that is, binding both to Trk and to $p75^{NTR}$. This is consistent with the data that cell damage in stroke does not occur immediately, but rather after about 24 hours. That is, the quantities of zinc released in stroke are sucked up by the neurotrophins and the cell damage is actually caused as a consequence of neurotrophin effects being inhibited or eliminated.

The inventors postulate a therapeutic compound which blocks at least a portion of the binding site of zinc, that is, it most likely disrupts the interaction of zinc with the His and Asp residues with which nickel does not interact. If a compound could be targeted to bind with these residues and block zinc binding to the neurotrophin or lower the affinity of zinc for the neurotrophin (preferably NGF), the compound could potentially be useful in preventing cellular damage after stroke.

FIG. 17 shows the structures of two prophetic molecules expected to bind to NGF at two of the four residues predicted to bind $Zn^{2+}$. The two molecules, each with an anionic group ($SO_{3-}$) and a cationic group ($NH_3^+$), are spaced appropriately to allow bridging of His 84 and Asp 105. Binding of the indicated molecules to NGF would be expected to reduce the ability of $Zn^{2+}$ to bind to NGF by competing for same binding site, and thus would alter the effects of $Zn^{2+}$ on NGF.

Referring to FIG. 18 there are shown the structures of two prophetic molecules expected to bind to NGF at the four amino acid residues (Asp 105, His 84, His 4, His 8) predicted to participate in binding of several metal ions to NGF. These two molecules have charge and steric features which would mimic the interaction of $Zn^{2+}$ and similar metals with NGF.

FIG. 19 shows the structures of five prophetic molecules expected to bind to NGF at the two His residues (His 4 and His 8) in the N-terminal region. The spacing of anionic groups ($SO_3^-$ or $O_2^-$) in these molecules is predicted to allow binding to the two His residues and alter conformation of the N-terminus in a manner similar to $Ni^{2+}$ and related metals. Mimicking $Ni^{2+}$, such factors should be selective for TrkA, i.e., not alter binding to $p75^{NTR}$. It will be understood by those skilled in the art that functional equivalents of these compounds can be produced based on these steric principles.

The foregoing description of the methods and compounds of the method of the present invention have been presented to illustrate the principles of the invention and not to limit the invention to the particular embodiment illustrated. It is intended that the scope of the invention be defined by all of the embodiments encompassed within the following claims and their functional equivalents.

Therefore what is claimed is:

1. A method of screening for a factor that disrupts the conformation of a homodimeric neurotrophin such that a biological activity of the neurotrophin is affected, comprising the steps of:

mixing a homodimeric neurotrophin having a conformation with a candidate factor, determining if said conformation of said homodimeric neurotrophin has been perturbed in the presence of said candidate factor, assaying a biological activity of the homodimeric neurotrophin in the presence of said candidate factor, and identifying a factor that perturbs said conformation such that said biological activity of the homodimeric neurotrophin is reduced.

2. The method according to claim 1, wherein said step of determining if said conformation has been perturbed includes probing said mixture using at least one of nuclear magnetic resonance spectroscopy, x-ray diffraction, fluorescence spectroscopy, and circular dichroism.

3. The method of screening according to claim 1, wherein the step of determining if said conformation has been perturbed includes separating different species of the neurotrophin, wherein the species are distinguished from each other by having different numbers of promoters, and the step of identifying includes identifying a factor that reduces the amount of a dimeric species of the neurotrophin in favor of a monomeric species.

4. The method according to claim 1, wherein the step of determining if said conformation has been perturbed includes determining if cross-linking efficiency between said promoters differs in the presence and absence of said candidate factor.

5. The method according to claim 1, wherein said factor that perturbs said conformation such that said biological activity of the neurotrophin is reduced interacts with a portion of the first protomer that, in the absence of said factor, associates with a portion of the second protomer.

6. The method according to claim 1, wherein said factor that perturbs said conformation such that sold biological activity of the neurotrophin is reduced mimics a portion of an interface between the first protomer and the second protomer of the neurotrophin.

7. The method according to claim 1, wherein the neurotrophin is selected from the group consisting of NGF, BDNF, NT-3, NT-4/5 and NT-6.

8. The method according to claim 1, wherein the so-identified factor is a peptide.

9. The method according to claim 1, wherein the so-identified factor is a peptidomimetic.

10. The method according to claim 1, wherein the so-identified factor is a divalent cation.

11. A method of screening for a factor that disrupts the association of promoters of a homodimeric neurotrophin such that a biological activity of the homodimeric neurotrophin is affected, comprising the steps of:

mixing a candidate factor with a homodimeric neurotrophin, separating different species of the neurotrophin present in the mixture, wherein the species are distinguished from each other by having different numbers of identical promoters, assaying a biological activity of the homodimeric neurotrophin in the presence of said candidate factor, and, identifying a factor that reduces the amount of a dimeric species of the neurotrophin in favor of a monomeric species such that said biological activity of the homodimeric neurotrophin is reduced.

12. The method according to claim 11, wherein the mixture is subjected to non-reducing gel electrophoresis and assayed for a change in relative amount of neurotrophin migrating as a dimer.

13. A method of screening for a factor that disrupts the association of promoters of a homodimeric neurotrophin such that a biological activity of the homodimeric neurotrophin is affected, comprising the steps of:

mixing a candidate factor that mimics a portion of an interface between promoters of a homodimeric neurotrophin with a homodimeric neurotrophin, separating different species of the neurotrophin present in the mixture, wherein the species are distinguished from each other by having different numbers of identical promoters, assaying a biological activity of the homodimeric neurotrophin in the presence of said candidate factor, and identifying a factor that reduces the amount of a dimeric species of the neurotrophin in favor of a monomeric species such that said biological activity of the homodimeric neurotrophin is reduced.

14. The method according to claim 13, wherein the mixture is subjected to non-reducing gel electrophoresis and assayed for a change in relative amount of neurotrophin migrating as a dimer.

15. The method according to claim 11, wherein the neurotrophin is selected from the group consisting of NGF, BDNF, NT-3, NT-4/5 and NT-6.

16. The method according to claim 11, wherein the s-identified factor is a peptide.

17. The method according to claim 11, wherein the so-identified factor is a peptidomimetic.

18. The method according to claim 11, wherein the so-identified factor is a divalent cation.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 1:

Cys Gly Ser Glu Val Pro Asn Ser Ala Arg Cys Cys Val Cys
1               5                   10

(2) INFORMATION FOR SEQ ID NO: 2:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Cys Gly Ser Asp Val Pro Asn Pro Asp Arg Cys Cys Val Cys
1               5                   10

(2) INFORMATION FOR SEQ ID NO: 3:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Cys Gly Glu Lys Thr Tyr Cys Met Pro Asn Cys Cys Val Cys
1               5                   10

(2) INFORMATION FOR SEQ ID NO: 4:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Cys Gly Glu Lys Thr Tyr Gly Met Pro Asn Cys Cys Val Cys
1               5                   10

(2) INFORMATION FOR SEQ ID NO: 5:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Cys Gly Asn Lys Val Pro Arg Ala Glu Lys Cys Cys Val Cys
1               5                   10

(2) INFORMATION FOR SEQ ID NO: 6:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide

```
    (ix) FEATURE:
         (A) NAME/KEY: Peptide
         (B) LOCATION: 1
         (D) OTHER INFORMATION: /note="Xaa is Cys, decarboxylated Cys
             or C-blocked Cys"

(ix) FEATURE:
         (A) NAME/KEY: Peptide
         (B) LOCATION: 4
         (D) OTHER INFORMATION: /note="Xaa is Glu or Asp"

(ix) FEATURE:
         (A) NAME/KEY: Peptide
         (B) LOCATION: 8
         (D) OTHER INFORMATION: /note="Xaa is Pro or Ser"

(ix) FEATURE:
         (A) NAME/KEY: Peptide
         (B) LOCATION: 9
         (D) OTHER INFORMATION: /note="Xaa is Asp or Ala"

(ix) FEATURE:
         (A) NAME/KEY: Peptide
         (B) LOCATION: 14
         (D) OTHER INFORMATION: /note="Xaa is Cys, desamino cys or
             N-blocked Cys"

(xi) SEQUENCE DESCRIPTION: SEQ ID NO: 6:

Xaa Gly Ser Xaa Val Pro Asn Xaa Xaa Arg Cys Cys Val Xaa
1               5                   10

(2) INFORMATION FOR SEQ ID NO: 7:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 7:

Cys Arg Ala Ser Asn Pro Val Glu Ser Gly Cys Cys Val Cys
1               5                   10

(2) INFORMATION FOR SEQ ID NO: 8:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 8:

Cys Val Cys Cys Arg Ala Ser Asn Pro Val Glu Ser Gly Cys
1               5                   10

(2) INFORMATION FOR SEQ ID NO: 9:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 9:

Cys Xaa Xaa Xaa Xaa Xaa Xaa Cys Cys Val Cys
1               5                   10
```

-continued (2) INFORMATION FOR SEQ ID NO: 10:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Cys Cys Val Cys Xaa Xaa Xaa Xaa Xaa Xaa Cys
1               5                       10
```

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

```
Cys Xaa Xaa Xaa Xaa Xaa Cys Cys Val Cys
1               5                   10
```